(12) United States Patent
Lepifre et al.

(10) Patent No.: US 9,381,191 B2
(45) Date of Patent: Jul. 5, 2016

(54) IMIDAZOPYRIDINE DERIVATIVES USEFUL IN TREATING DIABETES

(71) Applicant: METABRAIN RESEARCH, Chilly Mazarin (FR)

(72) Inventors: Franck F. Lepifre, Saclay (FR); Gersande R. Lena, Julienas (FR); Valerie Autier, Gif sur Yvette (FR); Micheline R. Kergoat, Bures sur Yvette (FR); Christine G. Charon, Gometz le Chatel (FR); Sophie N. Raynal, Paris (FR); Annick M. Audet, Leudeville (FR)

(73) Assignee: METABRAIN RESEARCH, Chilly Mazarin (FR)

(*) Notice: Subject to any disclaimer, the term of this patent is extended or adjusted under 35 U.S.C. 154(b) by 0 days.

(21) Appl. No.: 14/415,985

(22) PCT Filed: Jul. 16, 2013

(86) PCT No.: PCT/FR2013/051703
§ 371 (c)(1),
(2) Date: Jan. 20, 2015

(87) PCT Pub. No.: WO2014/013182
PCT Pub. Date: Jan. 23, 2014

(65) Prior Publication Data
US 2015/0182507 A1  Jul. 2, 2015

(30) Foreign Application Priority Data
Jul. 20, 2012  (FR) ...................... 12 57082

(51) Int. Cl.
| | | |
|---|---|---|
| C07D 471/02 | (2006.01) |
| A61K 31/437 | (2006.01) |
| C07D 471/04 | (2006.01) |
| A61K 31/155 | (2006.01) |
| A61K 31/444 | (2006.01) |
| A61K 31/5377 | (2006.01) |

(52) U.S. Cl.
CPC ............ *A61K 31/437* (2013.01); *A61K 31/155* (2013.01); *A61K 31/444* (2013.01); *A61K 31/5377* (2013.01); *C07D 471/04* (2013.01)

(58) Field of Classification Search
None
See application file for complete search history.

(56) References Cited

FOREIGN PATENT DOCUMENTS

| EP | 2072516 | 6/2009 |
|---|---|---|
| EP | 2168965 | 3/2010 |
| WO | 2009023179 | 2/2009 |
| WO | 2009080291 | 7/2009 |
| WO | 2010034500 | 4/2010 |
| WO | 2010070008 | 6/2010 |
| WO | 2010089292 | 8/2010 |

OTHER PUBLICATIONS

Asfari et al.: "Establishment of 2-Mercaptoethanol-Dependent Differentiated Insulin-Secreting Cell Lines"; The Endocrine Society, 1992, vol. 130, pp. 167-178.
International search report for International application No. PCT/FR2013/051703, dated Aug. 29, 2013 (3 pages).
Enguehard-Gueiffier et al.: "Convenient Synthesis of Alkenyl-, Alkynyl-, and Allenyl-Substituted Imidazo[1,2-a] pyridines via Palladium-Catalyzed Cross-Coupling Reactions"; Helvetica Chimica Acta, 2007, vol. 90, pp. 2349-2367.
Kazzouli et al.: "Solution and Solid Phase Functionalization of Imidazo[1,2-a]pyridines"; Letters in Organic Chemistry, 2005, vol. 2, pp. 184-187.
Portha et al.: "Diabetogenic Effect of Streptozotocin in the Rat During the Perinatal Period"; Diabetes, 1974, vol. 23, pp. 889-895.
Giroix et al.: "Glocuse Insensitivity and Amino-acid Hypersensitivity of Insulin Release in Rats with Non-insulin-dependent Diabetes"; Diabetes, 1983, vol. 32, pp. 445-451.
Assan et al.: "Diphasic Glucagon Release Induced by Arginine in the Perfused Rat Pancreas"; Nature New Biology, 1972, vol. 239, pp. 125-126.
Sussman et al.: "An in Vitro Method for Studying Insulin Secretion in the Perfused Isolated Rat Pancreas"; Diabetes, 1966, vol. 15, pp. 466-472.
Goto et al.: "Spontaneous Diabetes Produced by Selective Breeding of Normal Wistar Rats"; Proc. Japan Acad., 1975, vol. 51, pp. 80-85.
Portha et al.: "The GK rat beta-cell: A prototype for the diseased human beta-cell in type 2 diabetes?"; Molecular and Cellular Endocrinology, 2009, vol. 297, pp. 73-85.

*Primary Examiner* — Heidi Reese
(74) *Attorney, Agent, or Firm* — Hamre, Schumann, Mueller & Larson, P.C.

(57) ABSTRACT

The present invention relates to imidazopyridine derivatives of the following general formula I:

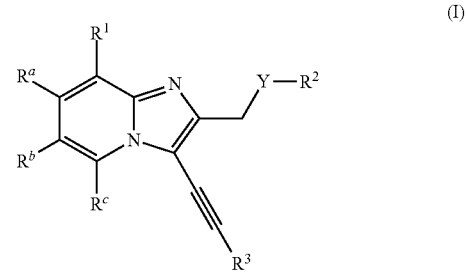

and to their use as a drug, in particular in treating and/or preventing diabetes, its complications and/or associated pathologies.

20 Claims, No Drawings

IMIDAZOPYRIDINE DERIVATIVES USEFUL IN TREATING DIABETES

DESCRIPTION OF THE INVENTION

The present invention relates to imidazopyridine derivatives useful in treating pathologies associated with the metabolic syndrome, in particular treating or preventing diabetes.

Diabetes mellitus represents a very heterogenous group of diseases all having in common a certain number of features: hyperglycemia, functional and quantitative abnormalities of pancreatic beta cells, tissue insulin-resistance and an increased risk of developing complications, in particular cardiovascular complications, in the long term.

Diabetes of type II has become a major problem of public health. Its prevalence is sharply increasing in most industrialized countries but even more in countries with a fully expanding economy. Today, this can be referred to as an epidemic for this disease which causes substantial complications which may become very invaliding or even lethal inter alia because of kidney failure, myocardial infarction or cardiovascular strokes.

A few figures on diabetes (WHO data):

More than 220 million persons are diabetic worldwide.

Diabetes multiplies by 3 the risks of stroke.

Diabetes is the first cause of blindness and of kidney failure in the western world.

According to estimations, diabetes has killed 1.1 million persons in 2005.

According to projections from the WHO, the number of deaths by diabetes will double between 2005 and 2030.

In France, care and treatment of diabetics is a great burden on the budget of State Health Insurance. Considering the alarming figures of the number of diabetic patients in the world from now to 2030, many pharmaceutical and biotechnological companies intensely invest in R&D in the field of metabolism and more particularly in that of diabetes type II in order to put on the market novel drug alternatives.

At the present time, no treatment of diabetes type II is capable of re-establishing normal glycemic equilibrium over 24 hours and is not without secondary effects. None of them take into account the complete pathology of the disease and only aim at correcting one or the other deficiency. Antidiabetics which have been put on the market quite recently have not shown any greater improvement in glycemic control than the one observed with pre-existing treatments and have caused undesirable secondary effects, which leaves room for novel potential treatments.

Therefore there exists a need for novel molecules useful in treating or preventing diabetes, or its complications and/or associated pathologies, advantageously diabetes of type II.

The inventors have surprisingly discovered that certain imidazopyridine derivatives have an inhibitory activity on liver production of glucose and an activity for secreting insulin in response to glucose and in particular which may be used as products for pharmaceutical use in patients which are in need thereof, notably for preventing and/or treating diabetes and its complications and/or associated pathologies (obesity, hypertension, etc. . . . ), advantageously diabetes of type II.

DETAILED DESCRIPTION OF THE INVENTION

The present invention therefore relates to imidazopyridine derivatives of the following general formula I:

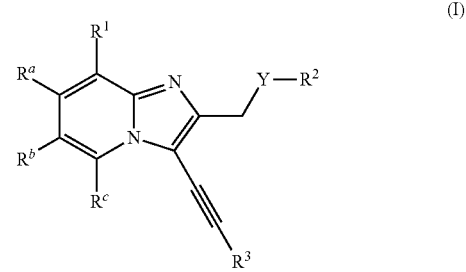

(I)

wherein:

Y represents an oxygen or sulfur atom, the group SO, $SO_2$ or —$NR^{19}$, wherein $R^{19}$ represents a hydrogen atom or a $C_1$-$C_6$ alkyl group, advantageously methyl (Me); advantageously Y represents an oxygen, sulfur atom or a group —$NR^{19}$, in particular an oxygen atom or a group —$NR^{19}$.

$R^1$, $R^a$, $R^b$ and $R^c$ represent independently of each other a hydrogen atom; a halogen atom, advantageously Cl; a $C_1$-$C_6$ alkyl group, advantageously methyl, optionally substituted with an —OH group; an —OH group; an —O($C_1$-$C_6$ alkyl) group such as -OMe, a —O($C_1$-$C_6$ alkyl)O($C_1$-$C_6$ alkyl) group; a —CN group; a group —$NR^4R^5$ wherein $R^4$ and $R^5$ represent independently of each other a hydrogen atom or a $C_1$-$C_6$ alkyl group; or a group —($C_1$-$C_6$ alkyl)$NR^6R^7$ wherein $R^6$ and $R^7$ represent independently of each other a hydrogen atom or a $C_1$-$C_6$ alkyl group;

$R^2$ represents a hydrogen atom;

a $C_1$-$C_6$ alkyl group substituted with an —OH group, in particular —$(CH_2)_2$OH;

a group —($C_1$-$C_6$ alkyl)$COOR^8$, advantageously —$CH_2COOR^8$, wherein $R^8$ represents a hydrogen atom or a $C_1$-$C_6$ alkyl group, in particular methyl (Me), ethyl (Et) or isopropyl (iPr), the alkyl group may be substituted with an —$NH_2$ or —OH group (advantageously, the alkyl group is not substituted), examples of —($C_1$-$C_6$ alkyl)$COOR^8$ groups are —$CH_2$COOH, —$CH_2$COOMe, —$CH_2$COOEt, —$CH_2$CH($NH_2$)COOEt and —$CH_2$COOiPr;

a group —($C_1$-$C_6$ alkyl)$CONHR^9$, advantageously —$CH_2CONHR^9$, wherein $R^9$ represents an —OH group; a $C_1$-$C_6$ alkyl group, advantageously an ethyl; an —O($C_1$-$C_6$ alkyl) group, advantageously -OEt; an aryl group, advantageously a phenyl; a heteroaryl group, advantageously a pyridyl; a group —(C=NH)NHCOO($C_1$-$C_6$ alkyl), advantageously —(C=NH)NHCOOt-butyl; a group —(C=NH)$NH_2$; or a —($C_1$-$C_6$ alkyl)$NR^{10}R^{11}$ group, advantageously —$(CH_2)_2NR^{10}R^{11}$, wherein $R^{10}$ and $R^{11}$ represent independently of each other, a $C_1$-$C_6$ alkyl group, advantageously a methyl; examples of —($C_1$-$C_6$ alkyl)$CONHR^9$ groups are —$CH_2$CONHOH, —$CH_2$CONHOEt and —$CH_2CONH(CH_2)_2NMe_2$;

a —($C_1$-$C_6$ alkyl)CO morpholine group, advantageously —$CH_2$CO morpholine;

a group —C(=O)$R^{12}$ wherein $R^{12}$ represents a —O($C_1$-$C_6$ alkyl) group, advantageously -Oisobutyl (OiBu); a $C_1$-$C_6$ alkyl group, advantageously an ethyl or isopropyl, optionally substituted with an —OH group, such as —(CH$_2$)$_2$OH; a morpholine group; a NH-aryl group, advantageously —NHphenyl, wherein the aryl group is optionally substituted with a group —COOH or —COO (C$_1$-C$_6$ alkyl), advantageously —COOMe; or a group —NR$^{13}$R$^{14}$ wherein R$^{13}$ and R$^{14}$ represent independently of each other a C$_1$-C$_6$ alkyl group, advantageously an ethyl; examples of groups —C(=O)R$'^2$ are —C(=O)OiBu, —C(=O)(CH$_2$)$_2$OH, —C(=O)NEt$_2$, —C(=O)Morpholine, —C(=O)iPr, —C(=O)NH-3-HO$_2$C-Ph and —C(=O)NH-3-MeO$_2$C-Ph;

a (C$_1$-C$_6$ alkyl)aryl group, advantageously a benzyl, wherein the aryl group is optionally substituted with a group —CN, —COOH or —COO(C$_1$-C$_6$ alkyl); an example of a substituted (C$_1$-C$_6$ alkyl)aryl group is —CH$_2$-3-NC-Ph;

a (C$_1$-C$_6$ alkyl)heteroaryl group, advantageously (C$_1$-C$_6$ alkyl)thiophene, in particular a methylthiophene group;

an aryl group, advantageously a phenyl, wherein the aryl group is optionally substituted with one or more groups selected from —COOH, —COO(C$_1$-C$_6$ alkyl), advantageously —COOMe, C$_1$-C$_6$ alkyl substituted with an —OH group, advantageously —CH$_2$OH, —CN, —CONHOH, —NHSO$_2$(C$_1$-C$_6$ alkyl), advantageously —NHSO$_2$Me or —CONH—(C$_1$-C$_6$ alkyl)NR$^{15}$R$^{16}$, advantageously —CONH-(ethyl)NR$^{15}$R$^{16}$, wherein R$^{15}$ and R$^{16}$ represent independently of each other a C$_1$-C$_6$ alkyl group, advantageously a methyl; examples of optionally substituted aryl groups are -Ph; -2-MeO$_2$C-Ph, -2-HO$_2$C-Ph, -3-MeO$_2$C-Ph, -3-HO$_2$C-Ph, -4-MeO$_2$C-Ph, -4-HO$_2$C-Ph; -2-HO$_2$HC-Ph, -3-MeSO$_2$HN-Ph, -3-NC-Ph, -2-HONHOC-Ph, and -2-Me$_2$N(CH$_2$)$_2$HNOC-Ph;

a heteroaryl group, advantageously a pyridyl;

a heterocyclic group, advantageously tetrahydrofurane, in particular including one or two heteroatoms, advantageously selected from N, S and O, the heterocyclic group may optionally include an unsaturation, such as thiazoline;

a lactone group with 3 to 6 members, in particular tetrahydrofuranone, optionally substituted with one or more C$_1$-C$_6$ alkyl groups, in particular with two groups such as two methyl groups;

or an —SO$_2$(C$_1$-C$_6$ alkyl) group, advantageously —SO$_2$(isopropyl);

R$^3$ represents an aryl group, advantageously a phenyl, or a heteroaryl group, advantageously a pyridyl or thienyl, wherein the aryl group is optionally substituted with one or more groups selected from —(C$_1$-C$_6$ alkyl), advantageously methyl, wherein the alkyl group is optionally substituted with one or more halogen atoms, advantageously F, such as for example —CF$_3$, or by a —CN group, such as for example —CH$_2$CN; a halogen atom, advantageously F, —O(C$_1$-C$_6$ alkyl), advantageously -OMe, wherein the alkyl group is optionally substituted with one or more halogen atoms, advantageously F, such as for example —OCF$_3$ or —OCH$_2$F; —CN; —OH; —NO$_2$; —COOH; —NR$^{17}$R$^{18}$ wherein R$^{17}$ and R$^{18}$ represent independently of each other a C$_1$-C$_6$ alkyl group, advantageously methyl; or —NHCO—(C$_1$-C$_6$ alkyl), advantageously —NHCOMe; examples of optionally substituted aryl groups are -Ph, -2-F$_3$C-Ph, -3-F$_3$C-Ph, -4-F$_3$C-Ph, -2-F-Ph, -3-F-Ph, -4-F-Ph, -3,4-(F)$_2$-Ph, -3-F-4-F$_3$CO-Ph, -3-F$_3$CO-Ph, -4-F$_3$CO-Ph, -3-F$_2$HCO-Ph, -3-NC-Ph, -3-HO-Ph, -2-MeO-Ph, -3-MeO-Ph, -4-MeO-Ph, -3,4-(MeO)$_2$-Ph, -4-Me-Ph, -4-Me$_2$N-Ph, -4-O$_2$N-Ph, -3-HO$_2$C-Ph, -3-MeCOHN-Ph and -4-NCH$_2$-Ph;

or an enantiomer, diastereoisomer, hydrate, solvate, tautomer, racemic mixture or a pharmaceutically acceptable salt of the latter.

In a particular embodiment of the present invention, Y represents an oxygen atom or the group —NH or -NMe, advantageously an oxygen atom.

In another particular embodiment of the present invention, R$^1$, R$^a$, R$^b$ and R$^c$ represent independently of each other a hydrogen atom, a halogen atom, in particular Cl or an —O(C$_1$-C$_6$ alkyl) group such as OMe, in particular a hydrogen atom or a halogen atom. Advantageously three among R$^1$, R$^a$, R$^b$ and R$^c$ represent a hydrogen atom and the fourth of them represents a hydrogen atom, a halogen atom, in particular Cl or a —O(C$_1$-C$_6$ alkyl) group such as OMe, advantageously a hydrogen atom or a halogen atom. More advantageously, R$^1$, R$^a$, R$^b$ and R$^c$ represent a hydrogen atom.

In still another particular embodiment of the present invention, R$^2$ represents a (C$_1$-C$_6$ alkyl)COOR$^8$ group, advantageously —CH$_2$COOR$^8$, wherein R$^8$ represents a hydrogen atom or a C$_1$-C$_6$ alkyl group in particular methyl (Me), ethyl (Et) or isopropyl (iPr), examples of —(C$_1$-C$_6$ alkyl)COOR$^8$ groups are —CH$_2$COOH, —CH$_2$COOMe, —CH$_2$COOEt and —CH$_2$COOiPr;

a (C$_1$-C$_6$ alkyl)CONHR$^9$ group, advantageously —CH$_2$CONHR$^9$, wherein R$^9$ represent an —OH group; an —O(C$_1$-C$_6$ alkyl) group, advantageously -OEt, or a —(C$_1$-C$_6$ alkyl)NR$^{10}$R$^{11}$ group wherein R$^{10}$ and R$^{11}$ represent independently of each other a C$_1$-C$_6$ alkyl group, advantageously methyl; examples of —(C$_1$-C$_6$ alkyl)CONHR$^9$ groups are —CH$_2$CONHOH, —CH$_2$CONHOEt and —CH$_2$CONH(CH$_2$)$_2$NMe$_2$;

an aryl group, advantageously a phenyl, wherein the aryl group is optionally substituted with one or more groups selected from —COOH, —COO(C$_1$-C$_6$ alkyl), advantageously —COOMe, —CONHOH, or —CONH—(C$_1$-C$_6$ alkyl)NR$^{15}$R$^{16}$, advantageously —CONH-(ethyl)NR$^{15}$R$^{16}$, wherein R$^{15}$ and R$^{16}$ represent independently of each other a C$_1$-C$_6$ alkyl group, advantageously a methyl; examples of optionally substituted aryl groups are -Ph; -2-MeO$_2$C-Ph, -2-HO$_2$C-Ph, -3-MeO$_2$C-Ph, -3-HO$_2$C-Ph, -4-MeO$_2$C-Ph, -4-HO$_2$C-Ph; -2-HONHOC-Ph, and -2-Me$_2$N(CH$_2$)$_2$HNOC-Ph; or a —CONH aryl group, advantageously —CONHphenyl, optionally substituted with a group —COOH or —COO (C$_1$-C$_6$ alkyl) advantageously —COOMe.

Advantageously, R$^2$ represents a —(C$_1$-C$_6$ alkyl)COOR$^8$ group wherein R$^8$ represents a hydrogen atom or a C$_1$-C$_6$ alkyl group, in particular methyl (Me), ethyl (Et) or isopropyl (iPr), or an aryl group, advantageously phenyl wherein the aryl group is optionally substituted with one or more groups, in particular a group, selected from —COOH, —COO(C$_1$-C$_6$ alkyl), advantageously —COOMe. More advantageously, R$^2$ represents a group —(C$_1$-C$_6$ alkyl)COOH, advantageously —CH$_2$COOH.

In still another particular embodiment of the present invention, R$^3$ represents an aryl group, advantageously a phenyl, optionally substituted with one or more groups selected from —(C$_1$-C$_6$ alkyl), advantageously methyl, wherein the alkyl group is optionally substituted with one or more halogen atoms, advantageously F, such as for example —CF$_3$; a halogen atom advantageously F, —O(C$_1$-C$_6$ alkyl), advantageously -OMe, wherein the alkyl group is optionally substituted with one or more halogen atoms, advantageously F, such as for example —OCF$_3$ or —OCH$_2$F; —CN; or —NO$_2$; examples of optionally substituted aryl groups are -Ph, -2-F$_3$C-Ph, -3-F$_3$C-Ph, -4-F$_3$C-Ph, -2-F-Ph, -3-F-Ph, -4-F-

Ph, -3,4-(F)$_2$-Ph, -3-F-4-F$_3$CO-Ph, -3-F$_3$CO-Ph, -4-F$_3$CO-Ph, -3-F$_2$HCO-Ph, -3-NC-Ph, -2-MeO-Ph, -3-MeO-Ph, -4-MeO-Ph, -3,4-(MeO)$_2$-Ph, -4-Me-Ph and -4-O$_2$N-Ph;

Advantageously, R$^3$ represents a phenyl group substituted with one or more groups selected from —(C$_1$-C$_6$ alkyl), advantageously methyl, substituted with one or more halogen atoms, advantageously F, such as for example —CF$_3$; a halogen atom, advantageously F, —O(C$_1$-C$_6$ alkyl), advantageously -OMe, wherein the alkyl group is substituted with one or more halogen atoms, advantageously F, such as for example —OCF$_3$; or —CN.

Within the scope of the present invention, by "aryl group", is meant an aromatic ring having 5 to 8 carbon atoms or several fused aromatic rings having 5 to 14 carbon atoms. In particular, the aryl groups may be monocyclic or bicyclic groups, preferably phenyl or naphthyl. Advantageously this is a phenyl group (Ph).

Within the scope of the present invention, by "heteroaryl group" is meant any hydrocarbon aromatic group with 3 to 9 atoms containing one or more heteroatoms, such as for example sulfur, nitrogen or oxygen atoms. The heteroaryl according to present invention may be formed with one or more fused rings. Examples of heteroaryl groups are furyl, isoxazyl, pyridyl, thiazolyl, pyrimidyl, benzimidazole, benzoxazole, thienyl, thiophenyl, benzothiazole groups. Advantageously, the heteroaryl group is selected from furyl, pyridyl, thiazolyl, thiophenyl and thienyl groups, advantageously this is the pyridyl, thiophenyl and thienyl group.

Within the scope of the present invention, by "heterocyclic group", is meant any saturated cyclic hydrocarbon group with 3 to 9 atoms containing one or more heteroatoms, such as for example sulfur, nitrogen or oxygen atoms. The heterocyclic group according to the present invention may be formed by one or more fused rings. Examples of heterocyclic groups are the tetrahydrofurane, pyrrolidyl, piperidyl, thiolane, oxirane, oxane, thiane, thiazolidine, morpholine groups. Advantageously, the heterocyclic group is selected from tetrahydrofurane, thiazolidine and morpholine groups.

Within the scope of the present invention, by "halogen atom" is meant any halogen atom, advantageously selected from Cl, Br, I or F, in particular selected from F, Cl or Br, in particular Cl or F.

Within the scope of the present invention, by "C$_1$-C$_6$ alkyl group" is meant any alkyl group with 1 to 6 carbon atoms, either linear or branched, in particular, the methyl, ethyl, n-propyl, iso-propyl, n-butyl, iso-butyl, sec-butyl, t-butyl, n-pentyl, n-hexyl groups. Advantageously, this is a methyl, ethyl, iso-butyl or iso-propyl group, in particular a methyl or ethyl group, more particularly a methyl group.

Within the scope of the present invention by "(C$_1$-C$_6$ alkyl) aryl group" is meant any aryl group as defined above, bound via a C$_1$-C$_6$ alkyl group as defined above. In particular an example of a (C$_1$-C$_6$ alkyl)aryl group is a benzyl group.

Within the scope of the present invention, by «(C$_1$-C$_6$ alkyl)heteroaryl group», is meant any heteroaryl group as defined above, bound via a C$_1$-C$_6$ alkyl group as defined above. In particular an example of a (C$_1$-C$_6$ alkyl)heteroaryl group is a methylthiophene group.

Within the scope of the present invention, by "pharmaceutically acceptable" is meant what is useful in the preparation of a pharmaceutical composition which is generally safe, non-toxic and neither undesirable biologically or otherwise and which is acceptable for veterinary use as well as in human pharmaceutics.

Within the scope of the present invention, by "pharmaceutically acceptable salts of a compound" are meant salts which are pharmaceutically acceptable, as defined here, and which have the desired pharmacological activity of the parent compound. Such salts comprise:

(1) acid addition salts formed with mineral acids such as hydrochloric acid, hydrobromic acid, sulfuric acid, nitric acid, phosphoric acid and the like; or formed with organic acids such as acetic acid, benzene-sulfonic acid, benzoic acid, camphor sulfonic acid, citric acid, ethane-sulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like; or (2) the salts formed when an acid proton present in the parent compound is either replaced with a metal ion, for example an alkaline metal ion, an earth alkaline metal ion or an aluminium ion; or is coordinated with an organic or inorganic base. The acceptable organic bases comprise diethanolamine, ethanolamine, N-methylglucamine, triethanolamine, tromethamine and the like. The acceptable inorganic bases comprise aluminium hydroxide, calcium hydroxide, potassium hydroxide, sodium carbonate and sodium hydroxide.

Within the scope of the present invention by "solvate of a compound", is meant any compound obtained by adding an inert solvent molecule onto the compound according to the invention, the solvate forming because of their mutual attraction force. Solvates are for example alcoholates of the compound. A hydrate is a solvate in which the inert solvent used is water. It may be a mono-, di- or tri-hydrate.

Within the scope of the present invention, by "tautomer" is meant any isomer for making up the compounds according to the present invention which are interconvertible by the reversible chemical reaction called tautomerisation. In most cases, the reaction occurs by migration of a hydrogen atom accompanied by a change in localisation of a double bond. In a solution of a compound capable of tautomerisation, an equilibrium between 2 tautomers is generated. The ratio between tautomers is then dependent on the solvent, on the temperature and on the pH. Tautomery is therefore the transformation of a functional group into another, most often by concomitant displacement of a hydrogen atom and of a n bond (double or triple bond). Common tautomers are for example the aldehyde/ketones-alcohols or more specifically enols pairs; amides -imidic acids; lactams-lactims; imines-enamines; enamines-enamines pairs. In particular, it may include a cycle-chain tautomery which occurs when the movement of the proton is accompanied by the transformation of an open structure to one ring.

In a particularly interesting embodiment of the present invention, the imidazopyridine derivatives are selected from the compounds of formulae 1 to 138 as indicated in table 1 hereafter.

In another still more interesting embodiment, the imidazopyridine derivatives are selected from the 84 compounds numbered as 1-3, 5, 7, 10-12, 14, 17, 18, 20, 23, 25-27, 29, 30, 32, 35, 38-40, 42, 44, 45, 46, 47, 48, 51, 54, 55, 57-59, 68, 72-79, 81, 83, 87-90, 92, 93, 95, 96, 101-126, 129-131 and 135 indicated in table 1 hereafter.

Still more advantageously, these are the compounds 3, 7, 14, 25, 26, 29, 44, 51, 54, 58, 59, 72, 76-79, 81, 87-90, 92, 93, 101, 102, 104, 110-112, 114-120 and 135 indicated in table 1 hereafter.

The present invention further relates to a pharmaceutical composition comprising a imidazopyridine derivative according to the present invention and a pharmaceutically acceptable excipient.

These compositions may be formulated for administration to mammals, including humans. The dosage varies according to the treatment and according to the relevant disease. These pharmaceutical compositions are adapted for administration via any suitable route, for example orally (including the buccal and sublingual routes), via a rectal, nasal, topical (including transdermal), vaginal, intraocular or parenteral (including subcutaneous, intramuscular or intravenous) route. Advantageously, the pharmaceutical compositions are adapted for oral administration. These formulations may be prepared by using all the methods known to one skilled in the art combining the active ingredients with suitable pharmaceutically acceptable excipients The suitable dosage unit forms orally comprise tablets, gelatin capsules, powders, granules and oral solutions or suspensions in aqueous or non-aqueous liquids, edible or food foams, or water-in-oil or oil-in-water liquid emulsions. When a solid composition is prepared as a tablet, the main active ingredient is advantageously mixed as a powder, with a suitable pharmaceutical excipient such as gelatin, starch, lactose, magnesium stearate, talcum, gum arabic or the like. It is possible to coat the tablets with saccharose or with other suitable materials or further they may be treated so that they have a prolonged or delayed activity and they release continuously a predetermined amount of active ingredient.

A preparation of gelatin capsules is obtained by mixing the active ingredient, advantageously as a powder, with a diluent and by pouring the obtained mixture in soft or hard gelatin capsules, in particular gelatin capsules. Lubricants such as for example talc, magnesium stearate, calcium stearate or polyethylene glycol in solid form may be added into the composition before its placing in gelatin capsules. A disintegrating agent or a solubiliser such as for example calcium carbonate or sodium carbonate may also be added in order to improve the availability of the drug after taking the gelatin capsule.

Further, if necessary, it is possible to add into the mixture, binders, lubricants and suitable disintegrating agents as well as colouring agents. The suitable binders may for example be starch, gelatin, natural sugars such as glucose or beta-lactose, sweetening agents made from maize, synthetic or natural rubber such as for example acacia or sodium alginate, carboxymethylcellulose, polyethylene glycol, waxes and the like. The lubricants which may be used in these dosage forms include sodium oleate, sodium stearate, magnesium stearate, sodium benzoate, sodium acetate, sodium chloride and the like. The disintegrating agents include starch, methylcellulose, agar, bentonite, xanthan gum and the like. The tablets are formulated for example by preparing a powder mixture, by granulation or dry pressing of the mixture, adding a lubricant and a disintegrating agent and pressing the mixture in order to obtain the tablets. A mixture of powder is prepared by mixing the active ingredient suitably added with a diluent or a base and optionally with a binder such as for example carboxymethylcellulose, alginate, gelatin or polyvinylpyrrolidone, a dissolution retardant such as for example paraffin, an absorption accelerating agent such as for example a quaternary salt and/or an absorbent such as for example bentonite, kaolin or dicalcium phosphate. The mixtures of powders may be granulated by wetting with a binder such as for example a syrup, a starch paste, acacia mucilage or cellulose solutions or polymeric materials and pressing through a sieve. The granules may be lubricated by adding a stearic acid, a stearate salt, talc or a mineral oil so as to avoid their adhering to the moulds allowing the manufacturing of the tablets. The lubricated mixture is then pressed in order to obtain the tablets. An opaque or transparent protective layer consisting in a shellac layer, a sugar layer or of polymeric materials is optionally present. Colouring agents may be added to these coatings so as to differentiate them from the other tablets.

A preparation as a syrup or elixir may contain the active ingredient together with a sweetener, an antiseptic, as well as an agent giving taste and a suitable colouring agent. Generally, the syrup preparations are obtained by dissolving the compound in an aqueous solution with an agent giving a suitable taste while elixirs are prepared by using a non-toxic alcohol carrier.

The powders or granules dispersible in water may contain the active ingredient mixed with dispersion agents or wetting agents, or suspension agents, such as for example ethoxylated isostearyl alcohols and polyoxyethylene sorbitol ethers, and also with taste correcting agents or sweeteners.

For rectal administration, one resorts to suppositories which are prepared with binders melting at the rectal temperature, for example cocoa butter or polyethylene glycols.

For parenteral, intranasal or intraocular administration, aqueous suspensions, isotonic saline solutions or sterile and injectable solutions are used which contain dispersion agents and/or pharmacologically compatible wetting agents.

The active ingredient may also be formulated as microcapsules, optionally with one or more additive supports.

The pharmaceutical compositions suitable for administration via a topical route may be formulated as a cream, an ointment, a suspension, a lotion, a powder, a solution, a paste, a gel, a spray, aerosols or oils.

Pharmaceutical compositions suitable for administration via a nasal route in which the supporting excipient is in the solid state comprise powders having particle sizes for example in the range from 20 to 500 microns, administered by inhalation from a container containing the powder placed near the nose.

The pharmaceutical formulations adapted to administration via a vaginal route may rather be administered as a buffer, a cream, a gel, pastes, a foam or spray.

In an advantageous embodiment, the pharmaceutical composition according to the present invention further comprises another active agent, advantageously having a complementary or synergistic effect. In particular, this active agent is another antidiabetic agent, advantageously selected from insulin, sulfonylureas, glinides, biguanides, thiazolidinediones, GLP-1R agonists, DPP-IV inhibitors, SGLT-2 inhibitors, advantageously selected from insulin, glibenclamide, gliclazide, glipizide, glimepiride, repaglinide, nateglinide, metformin, troglitazone, rosiglitazone, pioglitazone, exenatide, liraglutide, sitagliptin, vildagliptin, saxagliptin, alogliptin, dapagliflozin. More particularly, this is metformin. This second active agent may be administered in the same pharmaceutical composition as the imidazopyridine derivative of the present invention. It may also be administered separately, i.e. at the same moment or in a way spread out in time. Advantageously, this second active agent is administered orally.

The present invention further relates to an imidazopyridine derivative according to present invention for use as a drug.

The present invention also relates to the use of a imidazopyridine derivative according to present invention for preparing a drug.

According to the present invention, the compounds of formula (I) have an antihyperglycemic activity. They may reduce the hyperglycemia, more particularly hyperglycemia of diabetes type II. Notably, the compounds of the invention have an antihyperglycemic activity and are therefore useful in treating and/or preventing diabetes, its complications and/or its associated pathologies, such as for example the pathologies associated with metabolic syndrome, advantageously diabetes of type II or hyperglycemia. These drugs are particularly active in elderly persons. By "elderly persons" are meant persons, men or women, 65 years old or more.

The term of "resistance to insulin" as used within the scope of the present invention, refers to a condition where a normal amount of insulin is unable to produce a physiological or normal molecular response.

The present invention therefore relates to a imidazopyridine derivative according to the invention for use as a drug intended for treating and/or preventing diabetes, its complications and/or associated pathologies, advantageously of diabetes type II and of hyperglycemia.

The inventors have discovered that the derivatives according to the present invention gave the possibility of stimulating insulin secretion by INS1 cells and of inhibiting liver production of glucose at isolated rat hepatocytes.

Advantageously, diabetes is selected from early, belated, pediatric diabetes, of elderly and gestational persons, in particular elderly persons. Advantageously, the deficiencies of diabetes and the complications and/or pathologies associated with diabetes are selected from hyperglycemia, functional and quantitative abnormalities of endocrine pancreatic cells, insulin resistance, diabetic neuropathy, diabetic nephropathy, diabetic retinopathy, inflammation, obesity, hypertension, cardiovascular, microvascular, neurological problems and wound healing problems. Advantageously, this is hyperglycemia, functional and quantitative abnormalities of endocrine pancreatic cells, insulin resistance and inflammation.

Advantageously, the treated patient has risk factors associated with diabetes, i.e. a disease rate directly or indirectly associated with the occurrence of diabetes. In particular, this comprises family history, gestational diabetes, weight excess, obesity, insufficient physical exercise, hypertension, a high level of triglycerides, inflammation and hyperlipidaemia.

The present invention further relates to the use of a imidazopyridine derivative according to the invention for making a drug intended for treating and/or preventing diabetes, its complications and/or associated pathologies, notably of diabetes of type II and of hyperglycemia.

Finally, it relates to a treatment and/or preventive and/or prophylactic treatment method and/or for retarding occurrence of diabetes, of its complications and/or associated pathologies, advantageously of diabetes of type II and hyperglycemia, comprising the administration of an efficient amount of a imidazopyridine derivative according to the invention to a patient in need thereof.

The effective amount will be adapted depending on the nature and the severity of the pathology to be treated, the administration route and also the weight and the age of the patient. Generally, the dose unit will vary between 0.5 mg and 2,000 mg daily, in one or more takings, advantageously between 1 and 1,000 mg.

The imidazopyridine derivatives according to the invention are manufactured by methods well known to one skilled in the art and partly by methods as described hereafter.

The invention will be better understood upon reading the description and the examples which follow which are given as a non-limiting indication.

Description of the Synthesis and General Schemes

The compounds of general formula (I) may be prepared by applying or adapting any method known per se of and/or within the reach of one skilled in the art, notably those described by Larock in Comprehensive Organic Transformations, VCH Pub., 1989, or by applying or adapting methods described in the procedures which follow.

The synthesis of the molecules of general formula (I) is close, sometimes identical with, what was described in documents [1] to [8] without this list of references being considered as exhaustive.

The different groups $R^1$ to $R^3$ and Y of schemes 1 to 4 refer to the definitions given earlier; "GP" means protective group; "Hal" refers to a halogen atom.

The derivatives of formula I may be prepared according to a known method starting with 2-aminopyridine which reacts in one step with 1,3-dichloropropan-2-one in order to form the heterocycle 1.2. The chlorine of derivatives of type 1.2 is particularly suitable for being involved in various O-, S- or N-Alkylation reactions conduced in a basic medium with alcoholates, phenates and secondary amines. Once the chain is introduced, a selective halogenation (preferably an iodation reaction) reaction gives the possibility of obtaining the derivatives of type 1.4 which are engaged in reactions of the Sonogashira type for obtaining the derivatives of type 1.5.

Scheme 1:

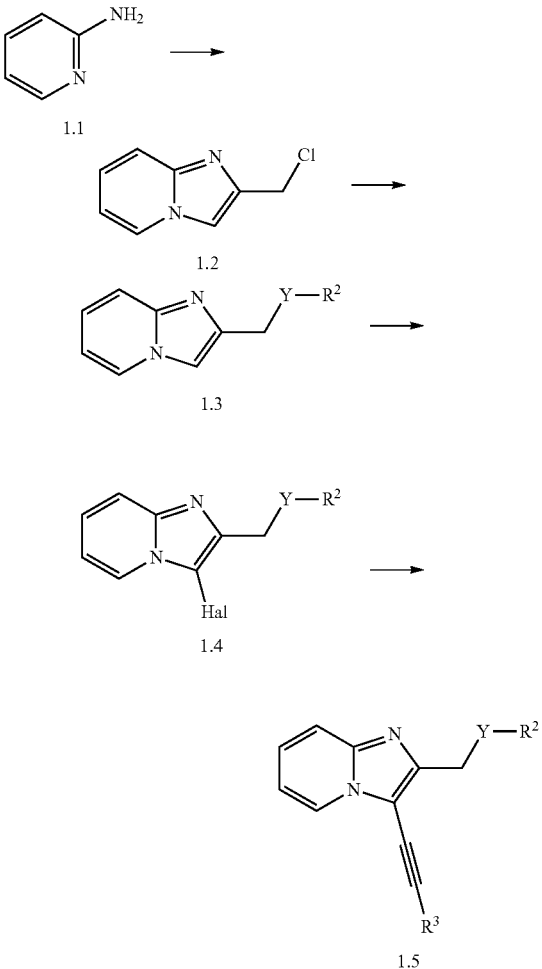

In the particular case when Y=NH, it is advantageous to use another approach for synthesising derivatives of formula I.

Scheme 2:

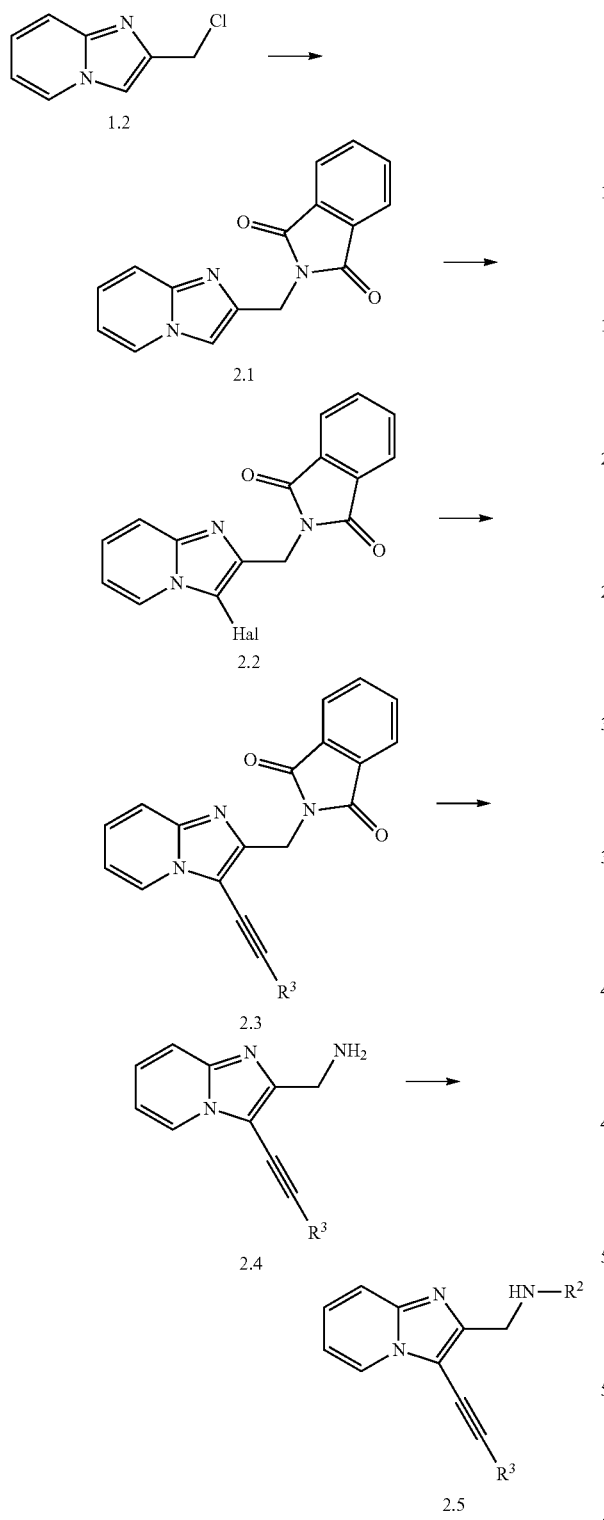

then be advantageously involved in reducing amination reactions, acylation reactions or further be put into the presence of isocyanates in order to obtain secondary amines, amides, carbamates or further ureas of the type 2.5.

An alternative method to the synthesis of derivatives of formula I for which Y=O was evaluated starting with imidazo[1,2-a]pyridin-2-ylmethanol 2.1 which may be protected by a suitable protective group (for example the triisopropylsilyl group) so as to be engaged in a halogenation (preferably an iodation reaction) reaction, followed by a reaction of the Sonogashira type. The protective group is cleaved subsequently to applying suitable conditions (tetrabutylammonium fluoride in the case of protection with a triisopropylsilyl group), the primary alcohol is then deprotonated with a base and engaged in alkylation reactions, or even acylation reactions, in order to obtain derivatives of type 3.6.

Scheme 3:

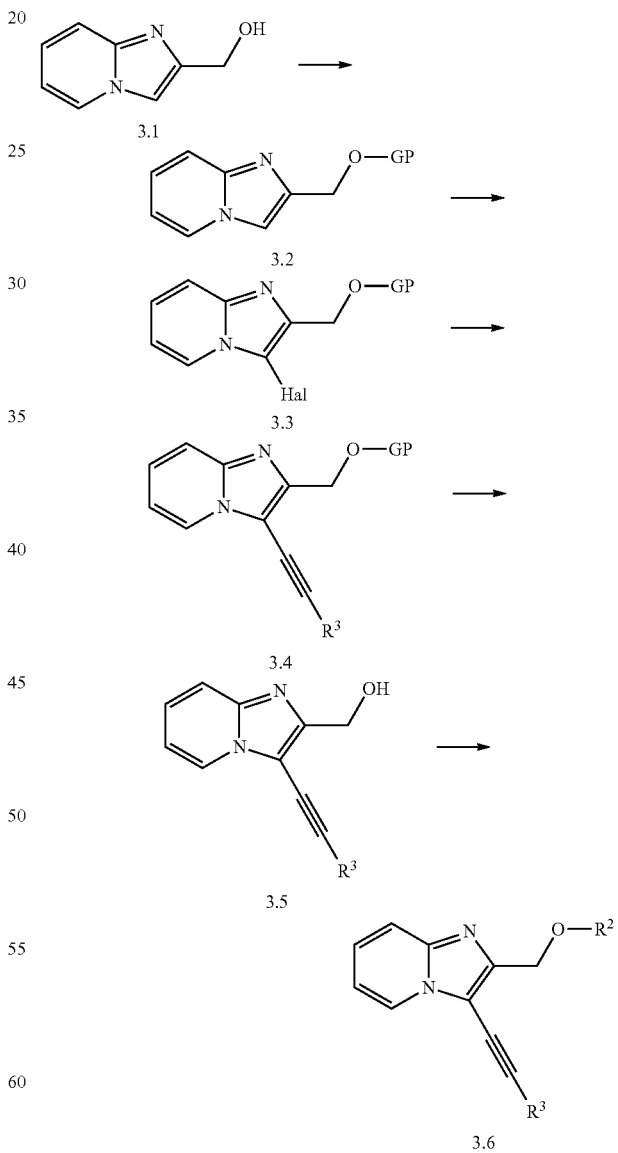

Starting with the chlorinated substance 1.2, an amine synthesis by the Gabriel method is carried out. The phthalimide derivative 2.1 is halogenated (preferably iodinated) so as to be then engaged into reactions of the Sonogashira type in order to obtain the derivatives of type 2.3, the primary amine is released under basic conditions. Derivatives of type 2.4 may A second method alternative to the synthesis of the derivatives of formula I for which Y=O was evaluated. This approach resorts to an initial different strategy for constructing the heterocycle since 2-aminopyridine is put into the presence of ethyl bromo pyruvate in order to form the ester derivative 4.1 which is then engaged into a halogenation reaction (preferably an iodation reaction), followed by a reaction of the Sonogashira type. The ester function is reduced to an alcohol by standard methods (reaction with a aluminium hydride) in order to engage the derivatives of type 3.5 into alkylation, or even acylation reactions.

Scheme 4:

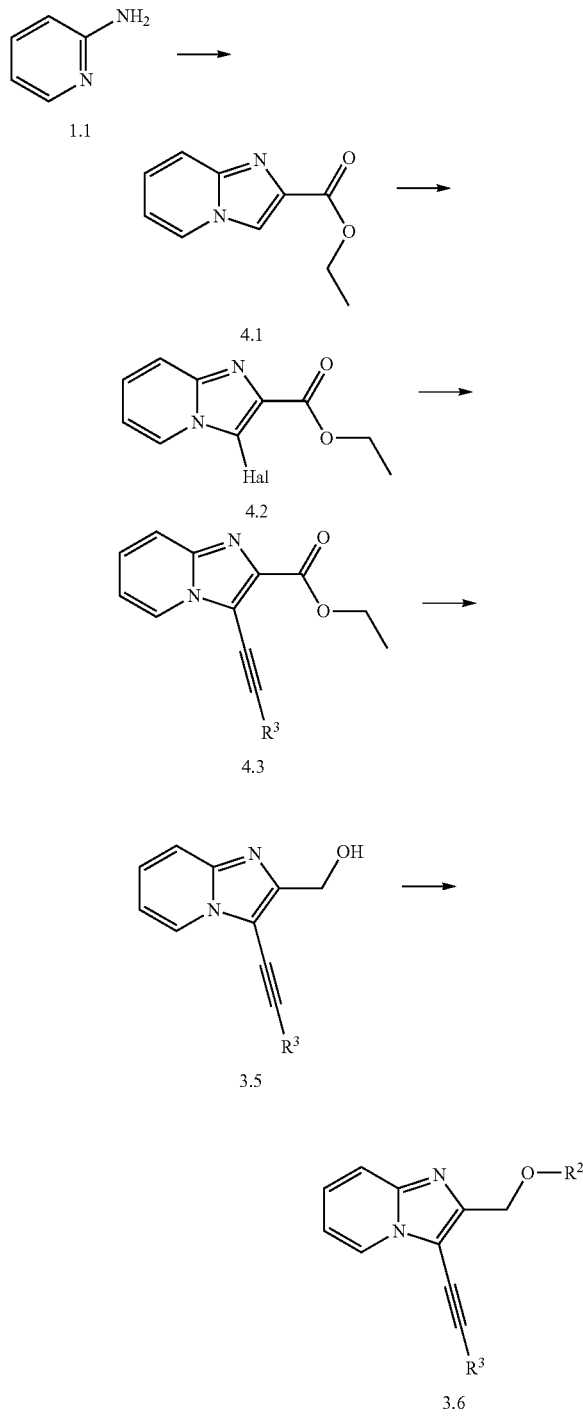

EXAMPLES

Equipment and Method

Nuclear Magnetic Resonance (NMR) spectra of the proton $^1$H are carried out on a Bruker Avance DPX300 apparatus (300.16 MHz). The chemical shifts (δ) are measured in parts per million (ppm). The spectra are calibrated on the chemical shift of the deuterated solvent used. The coupling constants (J) are expressed in Hertz (Hz) and multiplicity is illustrated in the following way, singlet (s), doublet (d), doublet of doublet (dd), triplet (t), triplet of doublet (td), quadruplet (q), multiplet (m). The mass spectra (SM) are achieved with a spectrometer from Agilent Technologies MSD, type G1946A, the samples are ionised with an "Atmospheric pressure chemical ionization" source (APCI).

ABBREVIATIONS

AIBN azoisobutyronitrile
dba dibenzylideneacetone
DIAD diisopropylazadicarboxylate
DME 1,2-dimethoxyethane
EDC N-(3-dimethylaminopropyl)-N-ethylcarbodiimide
HOBt 1-hydroxybenzotriazole
LAH lithium aluminium hydride
RED-Al sodium dihydrobis(2-methoxyethoxy) aluminate
TIPS triisopropylsilyl
CDCl$_3$ deuterated chloroform
DMSO deuterated dimethylsulfoxide
PyBOP (benzotriazol-1-yl-oxytripyrrolidinophosphonium hexafluorophosphate)
DMPU 1,3-dimethyl-3,4,5,6-tetrahydro-2(1H)-pyrimidinone
DMF dimethylformamide
Boc tert-butoxycarbonyl
mmol millimole(s)
µM micromolar
ml milliliter(s)
g gram(s)
M mol/liter
N normal
nm nanometer(s)
min minute(s)
h hour(s)
d days(s)
r.t. room temperature
UV ultra violet
ctrl control
HGP Hepatic Glucose Production The list of the examples above is used for illustrating the discussion of this invention and not for limiting the application field thereof.

TABLE 1

List of the molecules, the synthesis of which is exemplified

| No. | Chemical structure | Chemical name |
|-----|-------------------|---------------|
| 1 | 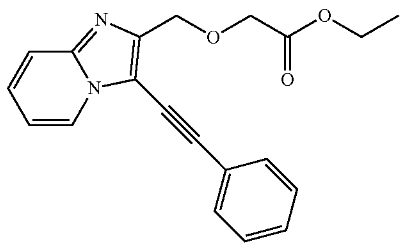 | ethyl 2-((3-(phenylethynyl)-imidazo[1,2-a]pyridin-2-yl)-methoxy)acetate |
| 2 | 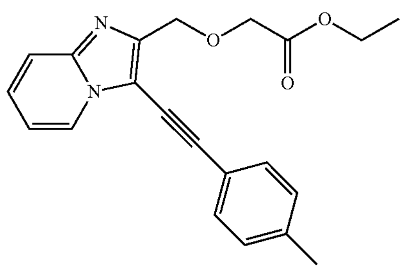 [SMILES: CCOC(=O)COCc1nc2ccccn2c1C#Cc1ccc(C)cc1] | ethyl 2-((3-(p-tolylethynyl)-imidazo[1,2-a]pyridin-2-yl)-methoxy)acetate |
| 3 | 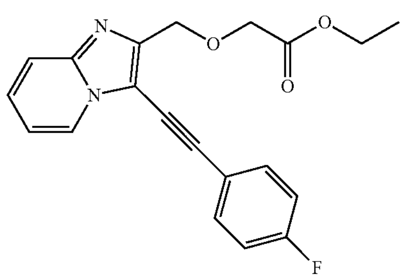 [SMILES: CCOC(=O)COCc1nc2ccccn2c1C#Cc1ccc(F)cc1] | ethyl 2-((3-((4-fluorophenyl)-ethynyl)imidazo[1,2-a]pyridin-2-yl)methoxy)acetate |
| 4 | 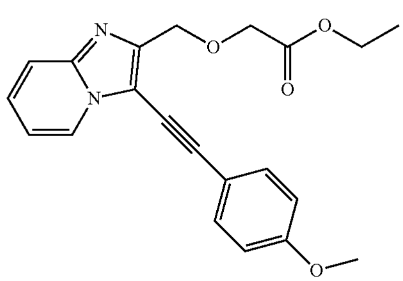 [SMILES: CCOC(=O)COCc1nc2ccccn2c1C#Cc1ccc(OC)cc1] | ethyl 2-((3-((4-methoxyphenyl)-ethynyl)-imidazo[1,2-a]pyridin-2-yl)-methoxy)acetate |
| 5 | 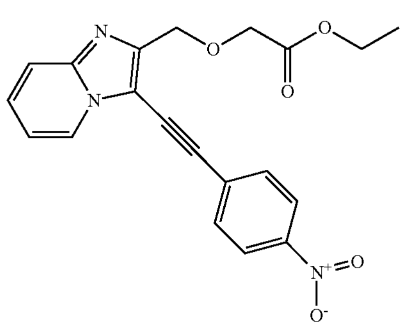 [SMILES: CCOC(=O)COCc1nc2ccccn2c1C#Cc1ccc([N+](=O)[O-])cc1] | ethyl 2-((3-((4-nitrophenyl)-ethynyl)imidazo[1,2-a]pyridin-2-yl)methoxy)acetate |

TABLE 1-continued

List of the molecules, the synthesis of which is exemplified

| No. | Chemical structure | Chemical name |
| --- | --- | --- |
| 6 | 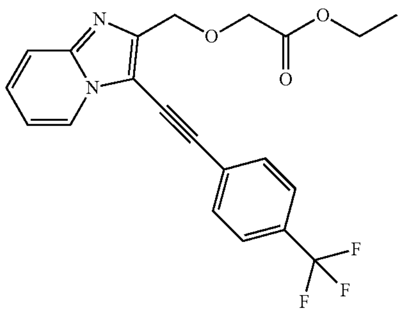 [SMILES: CCOC(=O)COCc1nc2ccccn2c1C#Cc1ccc(C(F)(F)F)cc1] | ethyl 2-((3-((4-(trifluoromethyl)-phenyl)ethynyl)imidazo[1,2-a]pyridin-2-yl)methoxy)acetate |
| 7 | 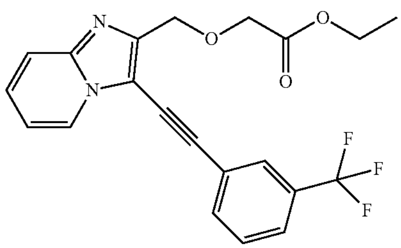 [SMILES: CCOC(=O)COCc1nc2ccccn2c1C#Cc1cccc(C(F)(F)F)c1] | ethyl 2-((3-((3-(trifluoromethyl)-phenyl)ethynyl)imidazo[1,2-a]pyridin-2-yl)methoxy)acetate |
| 8 | 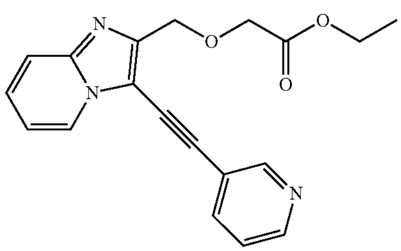 [SMILES: CCOC(=O)COCc1nc2ccccn2c1C#Cc1cccnc1] | ethyl 2-((3-(pyridin-3-ylethynyl)-imidazo[1,2-a]pyridin-2-yl)methoxy)acetate |
| 9 | 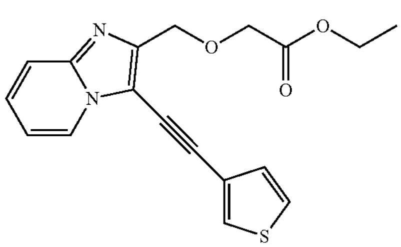 [SMILES: CCOC(=O)COCc1nc2ccccn2c1C#Cc1ccsc1] | ethyl 2-((3-(thiophen-3-ylethynyl)-imidazo[1,2-a]pyridin-2-yl)methoxy)acetate |
| 10 | 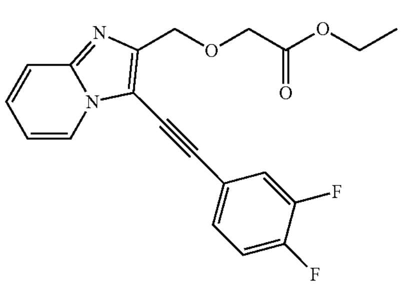 [SMILES: CCOC(=O)COCc1nc2ccccn2c1C#Cc1ccc(F)c(F)c1] | ethyl 2-((3-((3,4-difluorophenyl)-ethynyl)imidazo[1,2-a]pyridin-2-yl)methoxy)acetate |

TABLE 1-continued

List of the molecules, the synthesis of which is exemplified

| No. | Chemical structure | Chemical name |
|---|---|---|
| 11 | 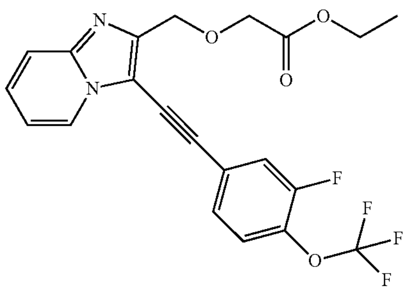 [SMILES: CCOC(=O)COCc1nc2ccccn2c1C#Cc1ccc(OC(F)(F)F)c(F)c1] | ethyl 2-((3-((3-fluoro-4-(trifluoromethoxy)phenyl)ethynyl)imidazo[1,2-a]pyridin-2-yl)methoxy)acetate |
| 12 | 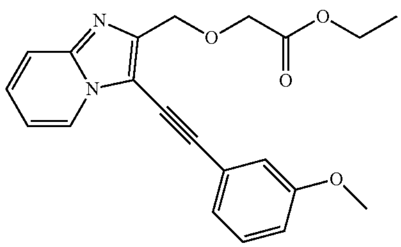 [SMILES: CCOC(=O)COCc1nc2ccccn2c1C#Cc1cccc(OC)c1] | ethyl 2-((3-((3-methoxyphenyl)ethynyl)imidazo[1,2-a]pyridin-2-yl)methoxy)acetate |
| 13 | 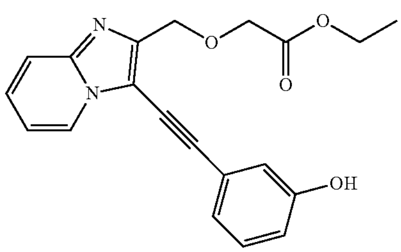 [SMILES: CCOC(=O)COCc1nc2ccccn2c1C#Cc1cccc(O)c1] | ethyl 2-((3-((3-hydroxyphenyl)ethynyl)imidazo[1,2-a]pyridin-2-yl)methoxy)acetate |
| 14 | 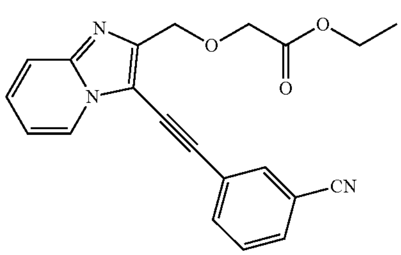 [SMILES: CCOC(=O)COCc1nc2ccccn2c1C#Cc1cccc(C#N)c1] | ethyl 2-((3-((3-cyanophenyl)ethynyl)imidazo[1,2-a]pyridin-2-yl)methoxy)acetate |
| 15 | 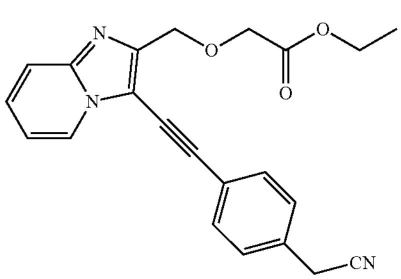 [SMILES: CCOC(=O)COCc1nc2ccccn2c1C#Cc1ccc(CC#N)cc1] | ethyl 2-((3-((4-(cyanomethyl)phenyl)ethynyl)imidazo[1,2-a]pyridin-2-yl)methoxy)acetate |

TABLE 1-continued

List of the molecules, the synthesis of which is exemplified

| No. | Chemical structure | Chemical name |
| --- | --- | --- |
| 16 | 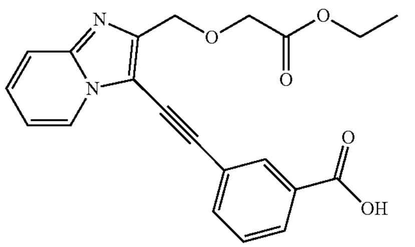 [SMILES: CCOC(=O)COCc1nc2ccccn2c1C#Cc1cccc(C(=O)O)c1] | 3-((2-((2-ethoxy-2-oxoethoxy)methyl)imidazo[1,2-a]pyridin-3-yl)ethynyl) benzoic acid |
| 17 | 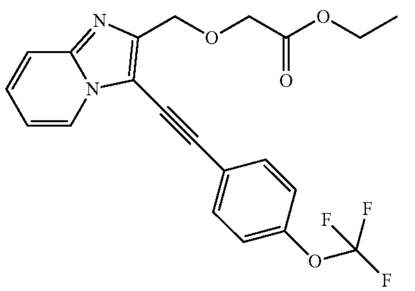 [SMILES: CCOC(=O)COCc1nc2ccccn2c1C#Cc1ccc(OC(F)(F)F)cc1] | ethyl 2-((3-((4-(trifluoromethoxy)-phenyl)ethynyl)imidazo[1,2-a]pyridin-2-yl)methoxy)acetate |
| 18 | 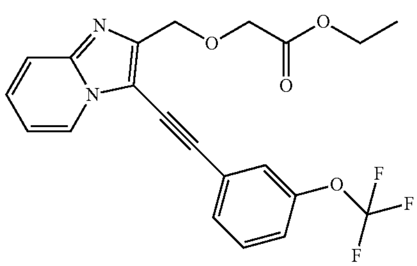 [SMILES: CCOC(=O)COCc1nc2ccccn2c1C#Cc1cccc(OC(F)(F)F)c1] | ethyl 2-((3-((3-(trifluoromethoxy)-phenyl)ethynyl)imidazo[1,2-a]pyridin-2-yl)methoxy)acetate |
| 19 | 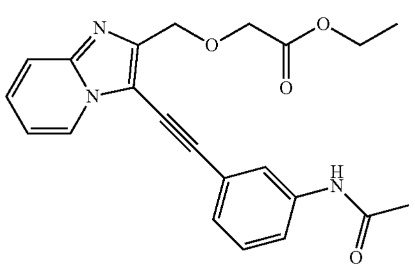 [SMILES: CCOC(=O)COCc1nc2ccccn2c1C#Cc1cccc(NC(C)=O)c1] | ethyl 2-((3-((3-acetamidophenyl)-ethynyl)imidazo[1,2-a]pyridin-2-yl)methoxy)acetate |
| 20 | 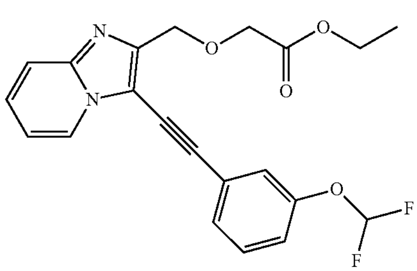 [SMILES: CCOC(=O)COCc1nc2ccccn2c1C#Cc1cccc(OC(F)F)c1] | ethyl 2-((3-((3-(difluoromethoxy)-phenyl)ethynyl)imidazo[1,2-a]pyridin-2-yl)methoxy)acetate |

TABLE 1-continued

List of the molecules, the synthesis of which is exemplified

| No. | Chemical structure | Chemical name |
|---|---|---|
| 21 | 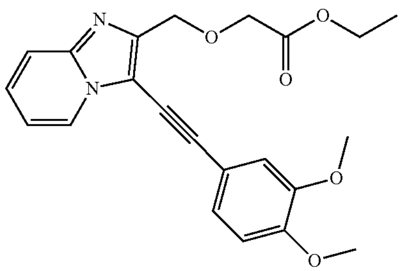 [SMILES: CCOC(=O)COCc1nc2ccccn2c1C#Cc1ccc(OC)c(OC)c1] | ethyl 2-((3-((3,4-dimethoxyphenyl)-ethynyl)imidazo[1,2-a]pyridin-2-yl)methoxy)acetate |
| 22 | 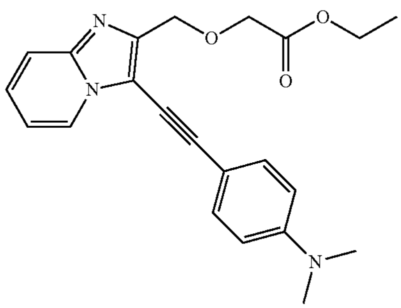 [SMILES: CCOC(=O)COCc1nc2ccccn2c1C#Cc1ccc(N(C)C)cc1] | ethyl 2-((3-((4-(dimethylamino)-phenyl)ethynyl)imidazo[1,2-a]pyridin-2-yl)methoxy)acetate |
| 23 | 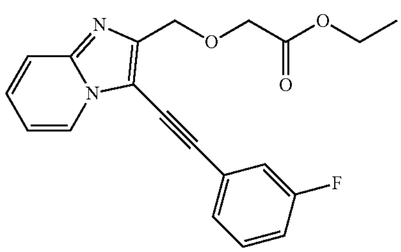 [SMILES: CCOC(=O)COCc1nc2ccccn2c1C#Cc1cccc(F)c1] | ethyl 2-((3-((3-fluorophenyl)-ethynyl)imidazo[1,2-a]pyridin-2-yl)methoxy)acetate |
| 24 | 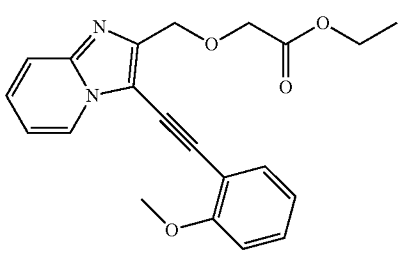 [SMILES: CCOC(=O)COCc1nc2ccccn2c1C#Cc1ccccc1OC] | ethyl 2-((3-((2-methoxyphenyl)-ethynyl)imidazo[1,2-a]pyridin-yl)methoxy)acetate |
| 25 | 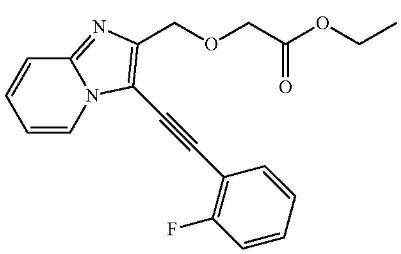 [SMILES: CCOC(=O)COCc1nc2ccccn2c1C#Cc1ccccc1F] | ethyl 2-((3-((2-fluorophenyl)-ethynyl)imidazo[1,2-a]pyridin-2-yl)methoxy)acetate |

TABLE 1-continued

List of the molecules, the synthesis of which is exemplified

| No. | Chemical structure | Chemical name |
|---|---|---|
| 26 | 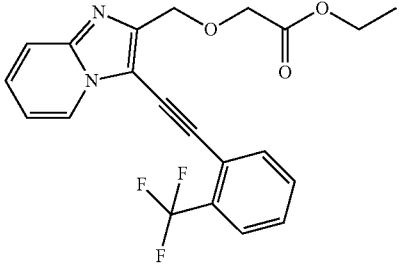 [SMILES: CCOC(=O)COCc1nc2ccccn2c1C#Cc1ccccc1C(F)(F)F] | ethyl 2-((3-((2-(trifluoromethyl)-phenyl)ethynyl)imidazo[1,2-a]pyridin-2-yl)methoxy)acetate |
| 27 | 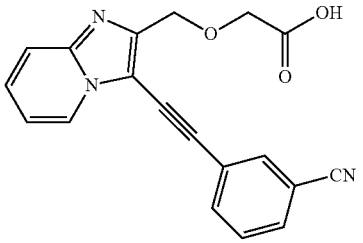 | 2-((3-((3-cyanophenyl)ethynyl)-imidazo[1,2-a]pyridin-2-yl)methoxy)acetic acid |
| 28 | 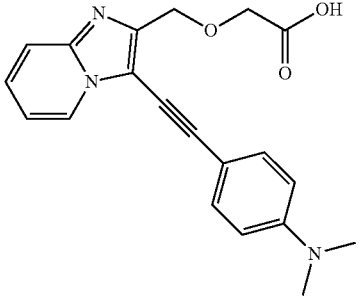 [SMILES: CN(C)c1ccc(C#Cc2c(COCC(=O)O)nc3ccccn23)cc1] | 2-((3-((4-(dimethylamino)phenyl)-ethynyl)imidazo[1,2-a]pyridin-2-yl)methoxy)acetic acid |
| 29 | 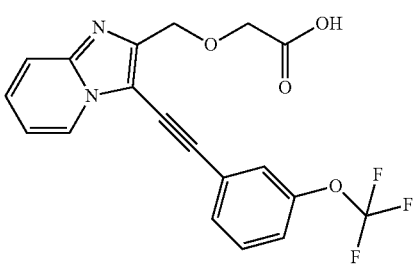 [SMILES: O=C(O)COCc1nc2ccccn2c1C#Cc1cccc(OC(F)(F)F)c1] | 2-((3-((3-(trifluoromethoxy)phenyl)-ethynyl)imidazo[1,2-a]pyridin-2-yl)methoxy)acetic acid |
| 30 | 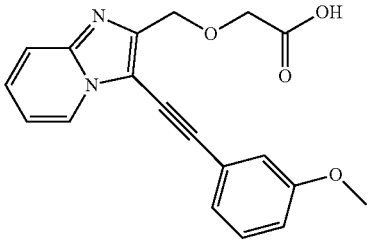 [SMILES: COc1cccc(C#Cc2c(COCC(=O)O)nc3ccccn23)c1] | 2-((3-((3-methoxyphenyl)ethynyl)-imidazo[1,2-a]pyridin-2-yl)methoxy)acetic acid |

TABLE 1-continued

List of the molecules, the synthesis of which is exemplified

| No. | Chemical structure | Chemical name |
|---|---|---|
| 31 | 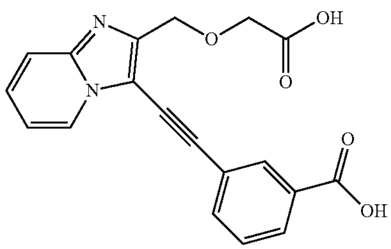 [SMILES: O=C(O)COCc1nc2ccccn2c1C#Cc1cccc(C(=O)O)c1] | 3-((2-((carboxymethoxy)methyl)-imidazo[1,2-a]pyridin-3-yl)ethynyl)benzoic acid |
| 32 | 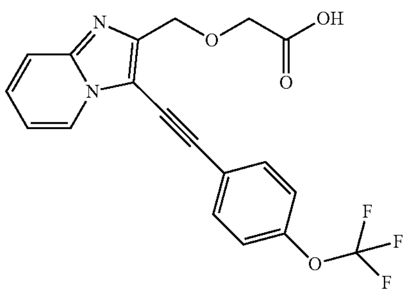 [SMILES: O=C(O)COCc1nc2ccccn2c1C#Cc1ccc(OC(F)(F)F)cc1] | 2-((3-((4-(trifluoromethoxy)phenyl)-ethynyl)imidazo[1,2-a]pyridin-2-yl)methoxy)acetic acid |
| 33 | 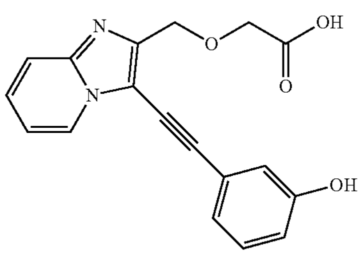 | 2-((3-((3-hydroxyphenyl)ethynyl)-imidazo[1,2-a]pyridin-2-yl)methoxy)acetic acid |
| 34 | 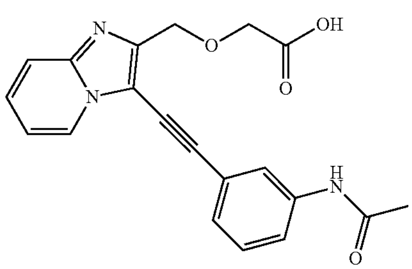 [SMILES: CC(=O)Nc1cccc(C#Cc2c(COCC(=O)O)nc3ccccn23)c1] | 2-((3-((3-acetamidophenyl)-ethynyl)imidazo[1,2-a]pyridin-2-yl)methoxy)acetic acid |
| 35 | 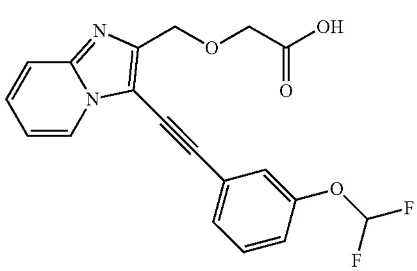 [SMILES: O=C(O)COCc1nc2ccccn2c1C#Cc1cccc(OC(F)F)c1] | 2-((3-((3-(difluoromethoxy)phenyl)-ethynyl)imidazo[1,2-a]pyridin-2-yl)methoxy)acetic acid |

TABLE 1-continued

List of the molecules, the synthesis of which is exemplified

| No. | Chemical structure | Chemical name |
|---|---|---|
| 36 | 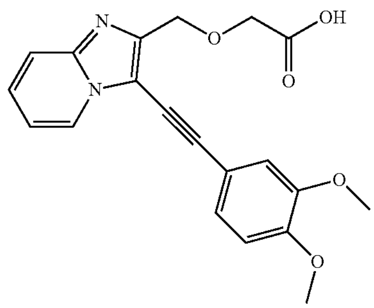 [SMILES: COc1ccc(C#Cc2c(COCC(=O)O)nc3ccccn23)cc1OC] | 2-((3-((3,4-dimethoxyphenyl)-ethynyl)imidazo[1,2-a]pyridin-2-yl)methoxy)acetic acid |
| 37 | 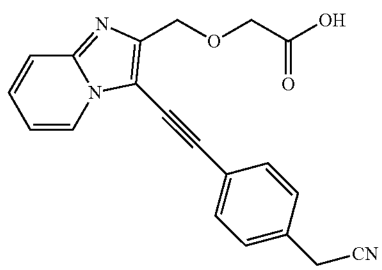 [SMILES: N#CCc1ccc(C#Cc2c(COCC(=O)O)nc3ccccn23)cc1] | 2-((3-((4-(cyanomethyl)phenyl)-ethynyl)imidazo[1,2-a]pyridin-2-yl)methoxy)acetic acid |
| 38 | 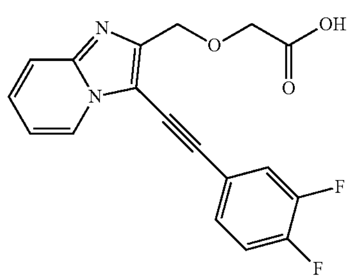 [SMILES: O=C(O)COCc1nc2ccccn2c1C#Cc1ccc(F)c(F)c1] | 2-((3-((3,4-difluorophenyl)ethynyl)-imidazo[1,2-a]pyridin-2-yl)methoxy)acetic acid |
| 39 | 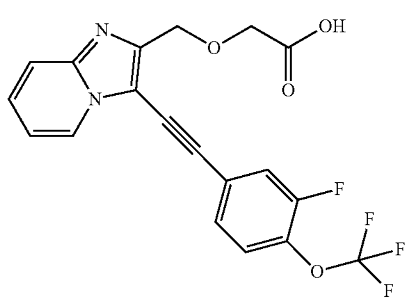 [SMILES: O=C(O)COCc1nc2ccccn2c1C#Cc1ccc(OC(F)(F)F)c(F)c1] | 2-((3-((3-fluoro-4-(trifluoro-methoxy)phenyl)ethynyl)imidazo[1,2-a]pyridin-2-yl)methoxy)acetic acid |
| 40 | 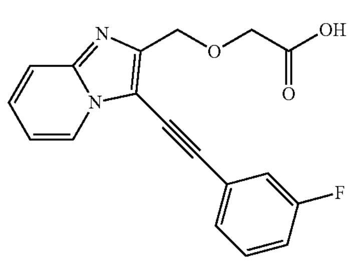 [SMILES: O=C(O)COCc1nc2ccccn2c1C#Cc1cccc(F)c1] | 2-((3-((3-fluorophenyl)ethynyl)-imidazo[1,2-a]pyridin-2-yl)methoxy)acetic acid |

TABLE 1-continued

List of the molecules, the synthesis of which is exemplified

| No. | Chemical structure | Chemical name |
|---|---|---|
| 41 | 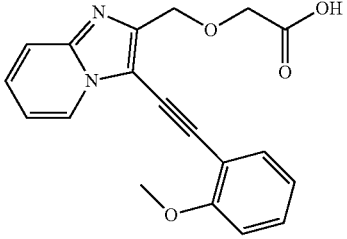 [SMILES: COc1ccccc1C#Cc1c(COCC(=O)O)nc2ccccn12] | 2-((3-((2-methoxyphenyl)ethynyl)-imidazo[1,2-a]pyridin-2-yl)methoxy)acetic acid |
| 42 | 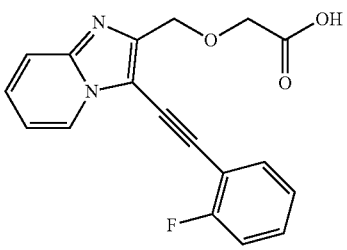 [SMILES: O=C(O)COCc1nc2ccccn2c1C#Cc1ccccc1F] | 2-((3-((2-fluorophenyl)ethynyl)-imidazo[1,2-a]pyridin-2-yl)methoxy)acetic acid |
| 43 | 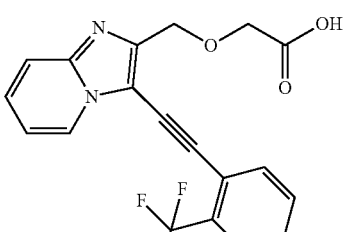 | 2-((3-((2-(trifluoromethyl)phenyl)-ethynyl)imidazo[1,2-a]pyridin-2-yl)methoxy)acetic acid |
| 44 | 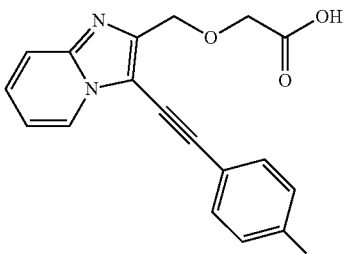 | 2-((3-((4-fluorophenyl)ethynyl)-imidazo[1,2-a]pyridin-2-yl)methoxy)acetic acid |
| 45 | 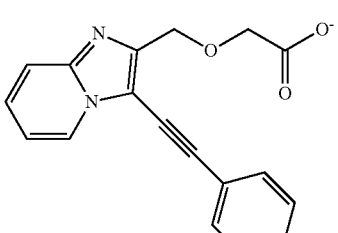 | sodium 2-((3-(phenylethynyl)-imidazo[1,2-a]pyridin-2-yl)methoxy)acetate |

TABLE 1-continued

List of the molecules, the synthesis of which is exemplified

| No. | Chemical structure | Chemical name |
|-----|--------------------|---------------|
| 46 | 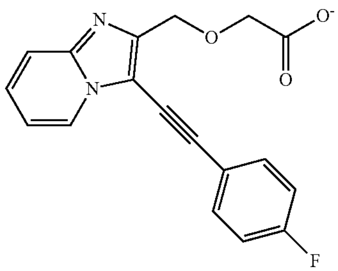 | sodium 2-((3-((4-fluorophenyl)-ethynyl)imidazo[1,2-a]pyridin-2-yl)methoxy)acetate |
| 47 | 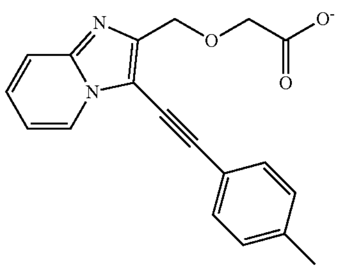 | sodium 2-((3-(p-tolylethynyl)imidazo-[1,2-a]pyridin-2-yl)methoxy)acetate |
| 48 | 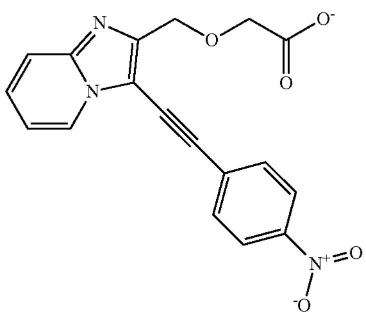 | sodium 2-((3-((4-nitrophenyl)-ethynyl)imidazo[1,2-a]pyridin-2-yl)methoxy)acetate |
| 49 | 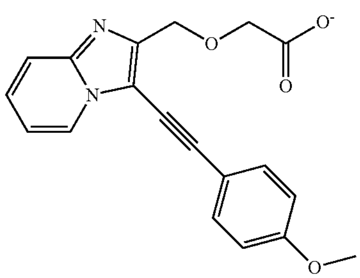 | Sodium 2-((3-((4-methoxyphenyl)-ethynyl)imidazo[1,2-a]pyridin-2-yl)methoxy)acetate |
| 50 | 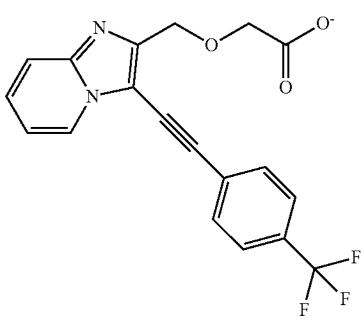 | sodium 2-((3-((4-(trifluoromethyl)-phenyl)ethynyl)imidazo[1,2-a]-pyridin-2-yl)methoxy)acetate |

TABLE 1-continued

List of the molecules, the synthesis of which is exemplified

| No. | Chemical structure | Chemical name |
|---|---|---|
| 51 | 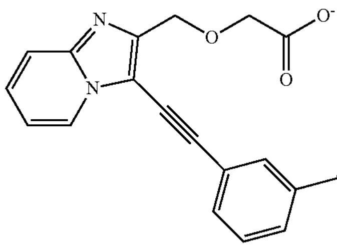 | sodium 2-((3-((3-(trifluoromethyl)-phenyl)ethynyl)imidazo[1,2-a]pyridin-2-yl)methoxy)acetate |
| 52 | 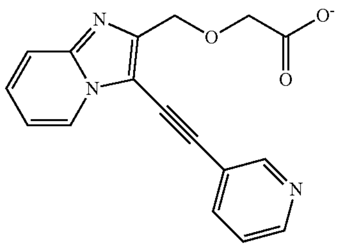 | sodium 2-((3-(pyridin-3-ylethynyl)-imidazo[1,2-a]pyridin-2-yl)methoxy)acetate |
| 53 | 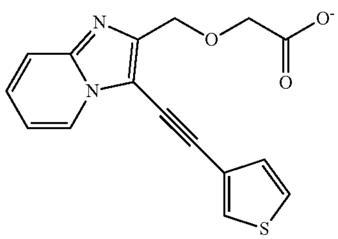 | sodium 2-((3-(thiophen-3-ylethynyl)-imidazo[1,2-a]pyridin-2-yl)methoxy)acetate |
| 54 | 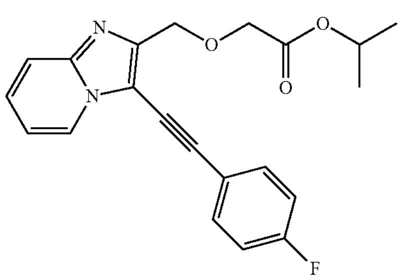 [SMILES: CC(C)OC(=O)COCc1nc2ccccn2c1C#Cc1ccc(F)cc1] | isopropyl 2-((3-((4-fluorophenyl)ethynyl)imidazo[1,2-a]pyridin-2-yl)methoxy)acetate |
| 55 | 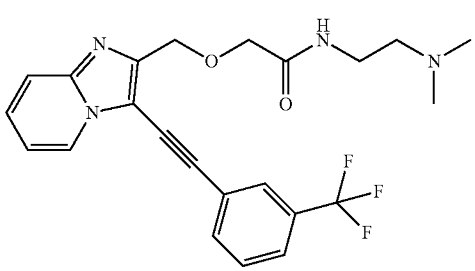 [SMILES: CN(C)CCNC(=O)COCc1nc2ccccn2c1C#Cc1cccc(C(F)(F)F)c1] | N-(2-(dimethylamino)ethyl)-2-((3-((3-(trifluoromethyl)-phenyl)ethynyl)imidazo[1,2-a]-pyridin-2-yl)methoxy)acetamide |

TABLE 1-continued

List of the molecules, the synthesis of which is exemplified

| No. | Chemical structure | Chemical name |
|---|---|---|
| 56 | 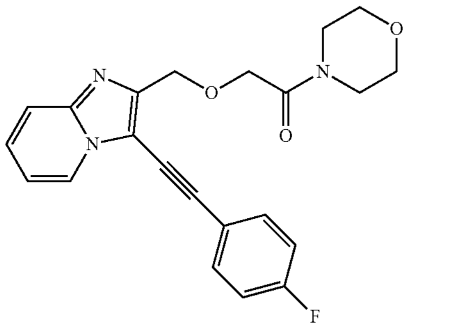 [SMILES: O=C(COCc1nc2ccccn2c1C#Cc1ccc(F)cc1)N1CCOCC1] | 2-((3-((4-fluorophenyl)ethynyl)-imidazo[1,2-a]pyridin-2-yl)methoxy)-1-morpholinoethanone |
| 57 | 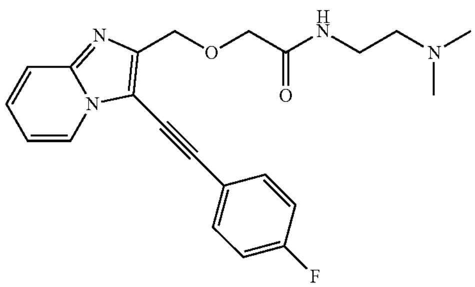 [SMILES: CN(C)CCNC(=O)COCc1nc2ccccn2c1C#Cc1ccc(F)cc1] | N-(2-(dimethylamino)ethyl)-2-((3-((4-fluorophenyl)ethynyl)-imidazo[1,2-a]pyridin-2-yl)methoxy)acetamide |
| 58 | 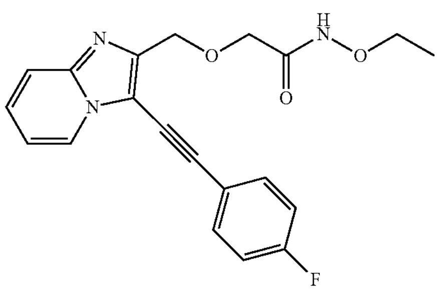 [SMILES: CCONC(=O)COCc1nc2ccccn2c1C#Cc1ccc(F)cc1] | N-ethoxy-2-((3-((4-fluorophenyl)ethynyl)imidazo[1,2-a]pyridin-2-yl)methoxy)acetamide |
| 59 | 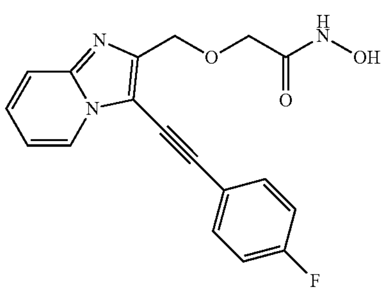 [SMILES: O=C(COCc1nc2ccccn2c1C#Cc1ccc(F)cc1)NO] | 2-((3-((4-fluorophenyl)ethynyl)-imidazo[1,2-a]pyridin-2-yl)methoxy)-N-hydroxyacetamide |
| 60 | 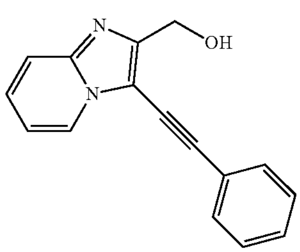 [SMILES: OCc1nc2ccccn2c1C#Cc1ccccc1] | (3-(phenylethynyl)imidazo[1,2-a]pyridin-2-yl)methanol |

TABLE 1-continued

List of the molecules, the synthesis of which is exemplified

| No. | Chemical structure | Chemical name |
|---|---|---|
| 61 | 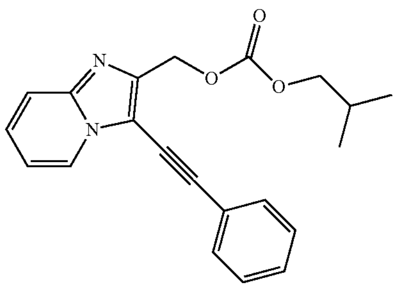 [SMILES: CC(C)COC(=O)OCc1nc2ccccn2c1C#Cc1ccccc1] | isobutyl ((3-(phenylethynyl)imidazo-[1,2-a]pyridin-2-yl)methyl) carbonate |
| 62 | 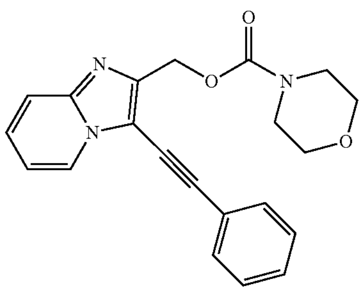 [SMILES: O=C(OCc1nc2ccccn2c1C#Cc1ccccc1)N1CCOCC1] | (3-(phenylethynyl)imidazo[1,2-a]pyridin-2-yl)methylmorpholine-4-carboxylate |
| 63 | 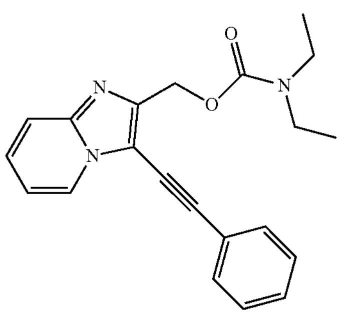 [SMILES: CCN(CC)C(=O)OCc1nc2ccccn2c1C#Cc1ccccc1] | (3-(phenylethynyl)imidazo[1,2-a]pyridin-2-yl)methyl diethylcarbamate |
| 64 | 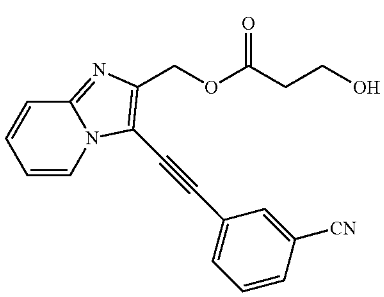 [SMILES: N#Cc1cccc(C#Cc2c(COC(=O)CCO)nc3ccccn23)c1] | (3-((3-cyanophenyl)ethynyl)imidazo[1,2-a]pyridin-2-yl)methyl 3-hydroxypropanoate |
| 65 | 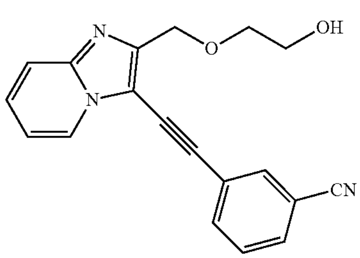 [SMILES: N#Cc1cccc(C#Cc2c(COCCO)nc3ccccn23)c1] | 3-((2-((2-hydroxyethoxy)methyl)imidazo[1,2-a]pyridin-3-yl)ethynyl)benzonitrile |

TABLE 1-continued

List of the molecules, the synthesis of which is exemplified

| No. | Chemical structure | Chemical name |
| --- | --- | --- |
| 66 | 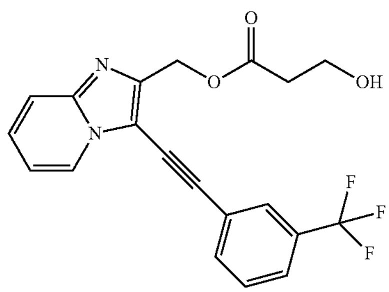 [SMILES: O=C(CCO)OCc1nc2ccccn2c1C#Cc1cccc(C(F)(F)F)c1] | (3-((3-(trifluoromethyl)phenyl)ethynyl)imidazo[1,2-a]pyridin-2-yl)methyl 3-hydroxypropanoate |
| 67 | 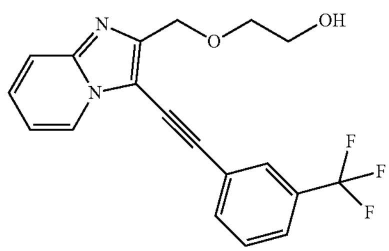 [SMILES: OCCOCc1nc2ccccn2c1C#Cc1cccc(C(F)(F)F)c1] | 2-((3-((3-(trifluoromethyl)phenyl)ethynyl)imidazo[1,2-a]pyridin-2-yl)methoxy)ethanol |
| 68 | 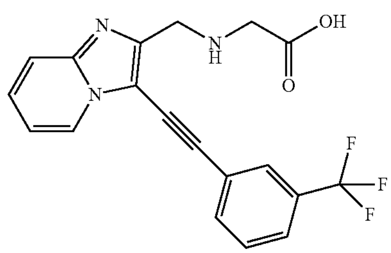 [SMILES: O=C(O)CNCc1nc2ccccn2c1C#Cc1cccc(C(F)(F)F)c1] | 2-(((3-((3-(trifluoromethyl)phenyl)ethynyl)imidazo[1,2-a]pyridin-2-yl)methyl)amino)acetic acid |
| 69 | 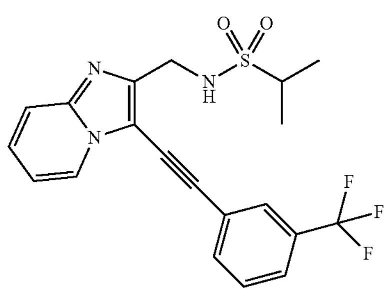 [SMILES: CC(C)S(=O)(=O)NCc1nc2ccccn2c1C#Cc1cccc(C(F)(F)F)c1] | N-((3-((3-(trifluoromethyl)phenyl)ethynyl)imidazo[1,2-a]pyridin-2-yl)methyl)propane-2-sulfonamide |
| 70 | 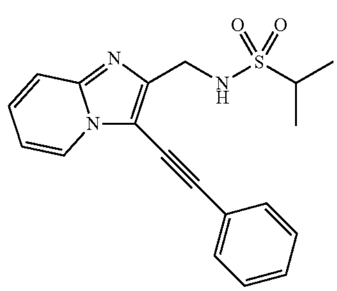 [SMILES: CC(C)S(=O)(=O)NCc1nc2ccccn2c1C#Cc1ccccc1] | N-((3-(phenylethynyl)imidazo[1,2-a]pyridin-2-yl)methyl)propane-2-sulfonamide |

TABLE 1-continued

List of the molecules, the synthesis of which is exemplified

| No. | Chemical structure | Chemical name |
|---|---|---|
| 71 | 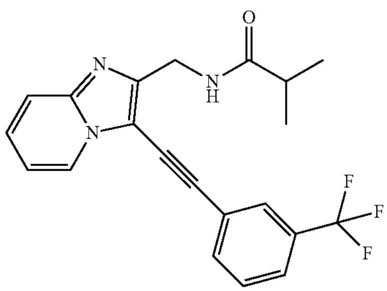 [SMILES: CC(C)C(=O)NCc1nc2ccccn2c1C#Cc1cccc(C(F)(F)F)c1] | N-((3-((3-(trifluoromethyl)phenyl)ethynyl)imidazo[1,2-a]pyridin-2-yl)methyl)isobutyramide |
| 72 | 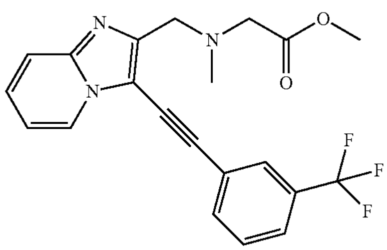 [SMILES: COC(=O)CN(C)Cc1nc2ccccn2c1C#Cc1cccc(C(F)(F)F)c1] | methyl 2-(methyl((3-((3-(trifluoromethyl)-phenyl)ethynyl)-imidazo[1,2-a]pyridin-2-yl)methyl)amino)acetate |
| 73 | 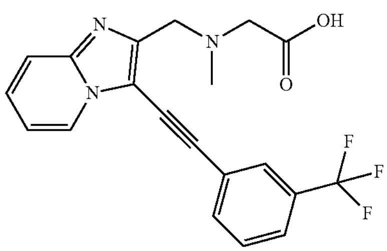 [SMILES: CN(CC(=O)O)Cc1nc2ccccn2c1C#Cc1cccc(C(F)(F)F)c1] | 2-(methyl((3-((3-(trifluoromethyl)phenyl)ethynyl)imidazo[1,2-a]pyridin-2-yl)methyl)amino)acetic acid |
| 74 | 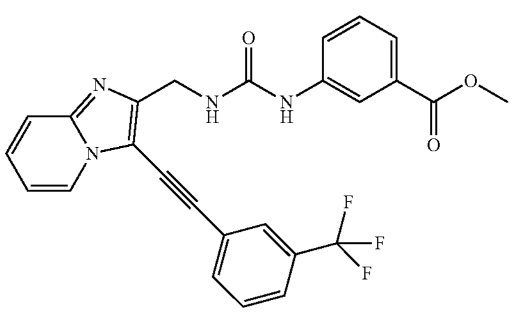 [SMILES: COC(=O)c1cccc(NC(=O)NCc2nc3ccccn3c2C#Cc2cccc(C(F)(F)F)c2)c1] | methyl 3-(3-((3-((3-(trifluoromethyl)phenyl)ethynyl)imidazo[1,2-a]pyridin-2-yl)methyl)ureido)-benzoate |
| 75 | 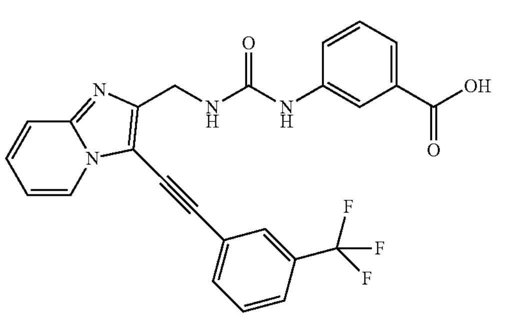 [SMILES: O=C(NCc1nc2ccccn2c1C#Cc1cccc(C(F)(F)F)c1)Nc1cccc(C(=O)O)c1] | 3-(3-((3-((3-(trifluoromethyl)-phenyl)ethynyl)imidazo[1,2-a]pyridin-2-yl)methyl)ureido)benzoic acid |

TABLE 1-continued

List of the molecules, the synthesis of which is exemplified

| No. | Chemical structure | Chemical name |
|---|---|---|
| 76 | 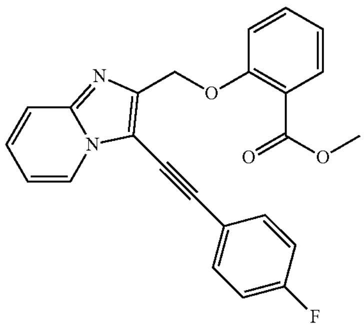 [SMILES: COC(=O)c1ccccc1OCc1nc2ccccn2c1C#Cc1ccc(F)cc1] | methyl 2-((3-((4-fluorophenyl)-ethynyl)imidazo[1,2-a]pyridin-2-yl)methoxy)benzoate |
| 77 | 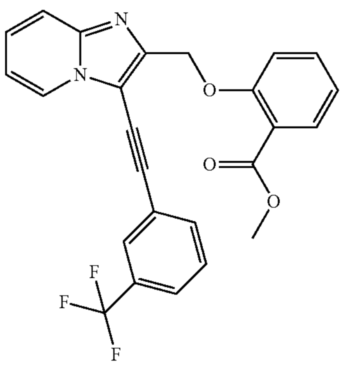 [SMILES: COC(=O)c1ccccc1OCc1nc2ccccn2c1C#Cc1cccc(C(F)(F)F)c1] | methyl 2-((3-((3-(trifluoromethyl)-phenyl)ethynyl)imidazo[1,2-a]pyridin-2-yl)methoxy)benzoate |
| 78 | 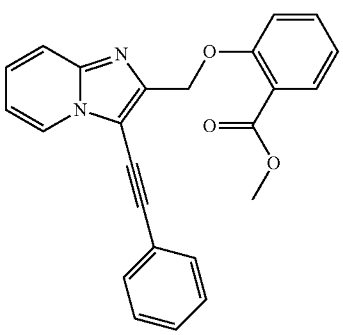 [SMILES: COC(=O)c1ccccc1OCc1nc2ccccn2c1C#Cc1ccccc1] | methyl 2-((3-(phenylethynyl)-imidazo[1,2-a]pyridin-2-yl)methoxy)benzoate |
| 79 | 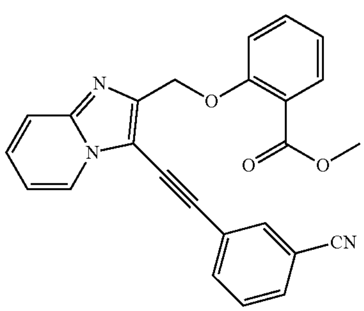 [SMILES: COC(=O)c1ccccc1OCc1nc2ccccn2c1C#Cc1cccc(C#N)c1] | methyl 2-((3-((3-cyanophenyl)-ethynyl)imidazo[1,2-a]pyridin-2-yl)methoxy)benzoate |

TABLE 1-continued

List of the molecules, the synthesis of which is exemplified

| No. | Chemical structure | Chemical name |
|---|---|---|
| 80 | 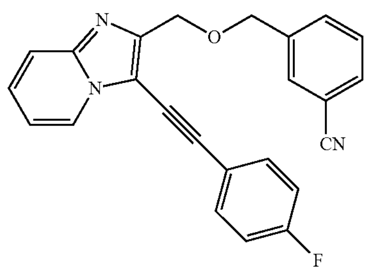 [SMILES: N#Cc1cccc(COCc2nc3ccccn3c2C#Cc2ccc(F)cc2)c1] | 3-(((3-((4-fluorophenyl)-ethynyl)imidazo[1,2-a]pyridin-2-yl)methoxy)methyl)benzonitrile |
| 81 | 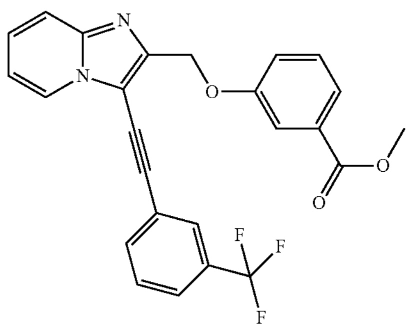 [SMILES: COC(=O)c1cccc(OCc2nc3ccccn3c2C#Cc2cccc(C(F)(F)F)c2)c1] | methyl 3-((3-((3-(trifluoromethyl)-phenyl)ethynyl)imidazo[1,2-a]pyridin-2-yl)methoxy)benzoate |
| 82 | 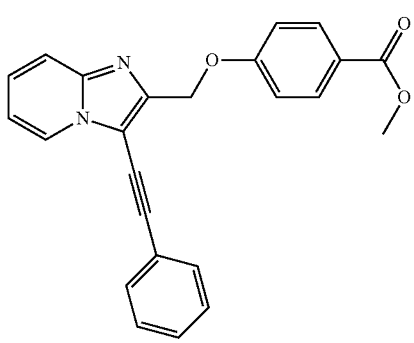 [SMILES: COC(=O)c1ccc(OCc2nc3ccccn3c2C#Cc2ccccc2)cc1] | methyl 4-((3-(phenylethynyl)-imidazo[1,2-a]pyridin-2-yl)methoxy)benzoate |
| 83 | 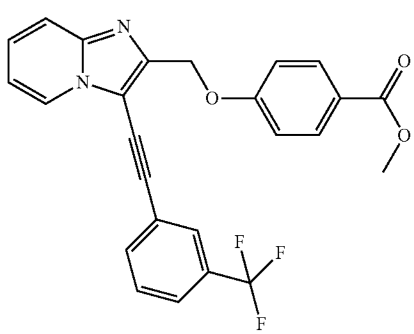 [SMILES: COC(=O)c1ccc(OCc2nc3ccccn3c2C#Cc2cccc(C(F)(F)F)c2)cc1] | methyl 4-((3-((3-(trifluoromethyl)-phenyl)ethynyl)imidazo[1,2-a]pyridin-2-yl)methoxy)benzoate |

TABLE 1-continued

List of the molecules, the synthesis of which is exemplified

| No. | Chemical structure | Chemical name |
|---|---|---|
| 84 | 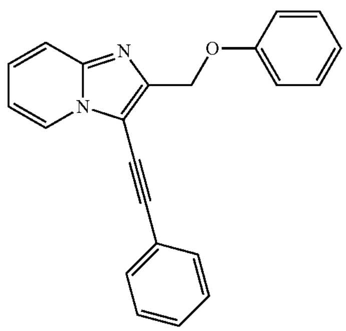 [SMILES: C(#Cc1c(COc2ccccc2)nc2ccccn12)c1ccccc1] | 2-(phenoxymethyl)-3-(phenylethynyl)imidazo[1,2-a]pyridine |
| 85 | 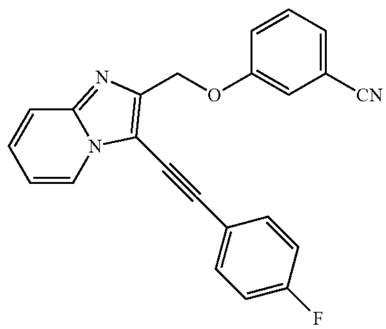 [SMILES: N#Cc1cccc(OCc2nc3ccccn3c2C#Cc2ccc(F)cc2)c1] | 3-((3-((4-fluorophenyl)-ethynyl)imidazo[1,2-a]pyridin-2-yl)methoxy)benzonitrile |
| 86 | 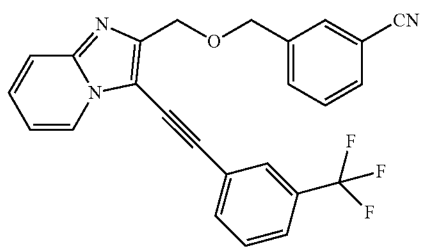 [SMILES: N#Cc1cccc(COCc2nc3ccccn3c2C#Cc2cccc(C(F)(F)F)c2)c1] | 3-(((3-((3-(trifluoromethyl)-phenyl)ethynyl)imidazo[1,2-a]pyridin-2-yl)methoxy)methyl)-benzonitrile |
| 87 | 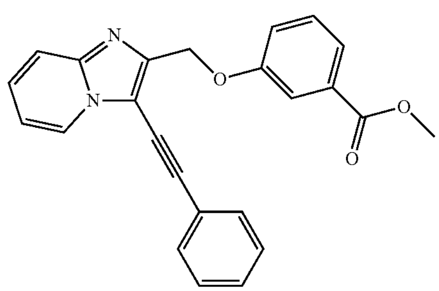 [SMILES: COC(=O)c1cccc(OCc2nc3ccccn3c2C#Cc2ccccc2)c1] | methyl 3-((3-(phenylethynyl)-imidazo[1,2-a]pyridin-2-yl)methoxy)benzoate |
| 88 | 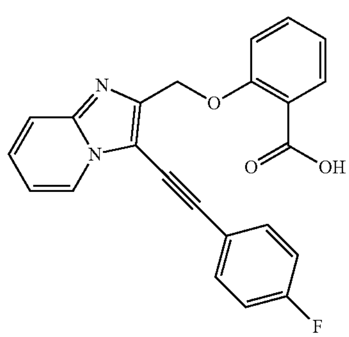 [SMILES: O=C(O)c1ccccc1OCc1nc2ccccn2c1C#Cc1ccc(F)cc1] | 2-((3-((4-fluorophenyl)ethynyl)-imidazo[1,2-a]pyridin-2-yl)methoxy)benzoic acid |

TABLE 1-continued

List of the molecules, the synthesis of which is exemplified

| No. | Chemical structure | Chemical name |
| --- | --- | --- |
| 89 | 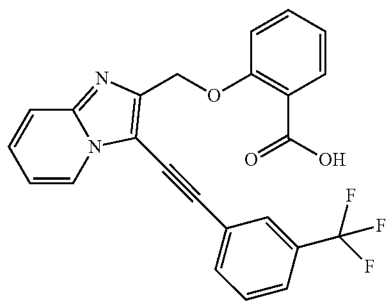 [SMILES: O=C(O)c1ccccc1OCc1nc2ccccn2c1C#Cc1cccc(C(F)(F)F)c1] | 2-((3-((3-(trifluoromethyl)phenyl)-ethynyl)imidazo[1,2-a]pyridin-2-yl)methoxy)benzoic acid |
| 90 | 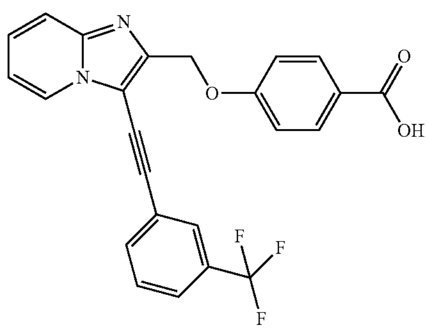 [SMILES: O=C(O)c1ccc(OCc2nc3ccccn3c2C#Cc2cccc(C(F)(F)F)c2)cc1] | 4-((3-((3-(trifluoromethyl)phenyl)-ethynyl)imidazo[1,2-a]pyridin-2-yl)methoxy)benzoic acid |
| 91 | 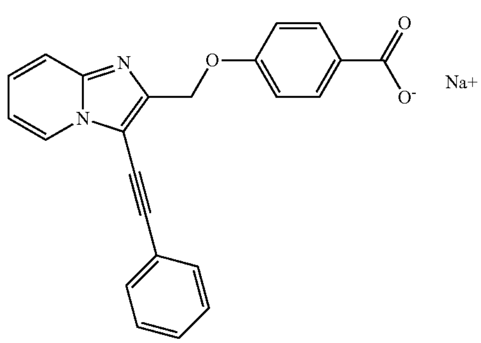 [SMILES: O=C([O-])c1ccc(OCc2nc3ccccn3c2C#Cc2ccccc2)cc1 ; [Na+]] | sodium 4-((3-(phenylethynyl)-imidazo[1,2-a]pyridin-2-yl)-methoxy)benzoate |
| 92 | 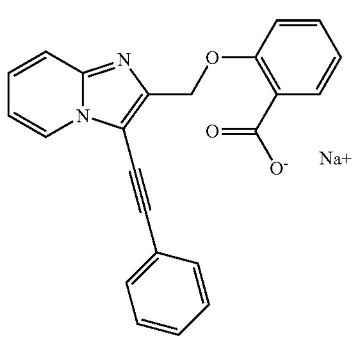 [SMILES: O=C([O-])c1ccccc1OCc1nc2ccccn2c1C#Cc1ccccc1 ; [Na+]] | sodium 2-((3-(phenylethynyl)imidazo-[1,2-a]pyridin-2-yl)methoxy)-benzoate |

TABLE 1-continued

List of the molecules, the synthesis of which is exemplified

| No. | Chemical structure | Chemical name |
|---|---|---|
| 93 | 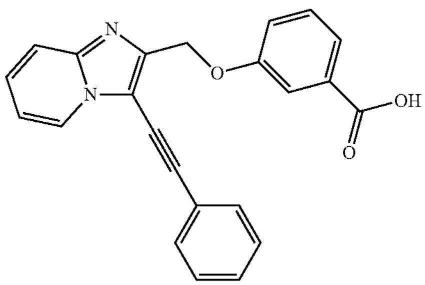 [SMILES: O=C(O)c1cccc(OCc2nc3ccccn3c2C#Cc2ccccc2)c1] | 3-((3-(phenylethynyl)imidazo[1,2-a]pyridin-2-yl)methoxy)benzoic acid |
| 94 | 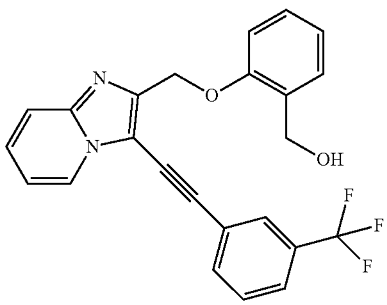 [SMILES: OCc1ccccc1OCc1nc2ccccn2c1C#Cc1cccc(C(F)(F)F)c1] | (2-((3-((3-(trifluoromethyl)-phenyl)ethynyl)imidazo[1,2-a]pyridin-2-yl)methoxy)-phenyl)methanol |
| 95 | 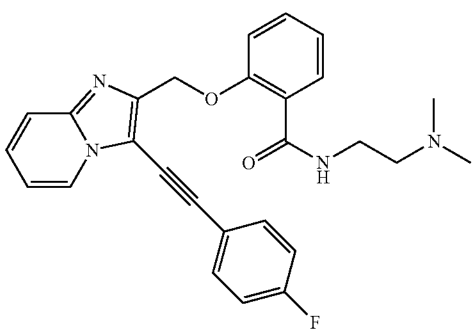 [SMILES: CN(C)CCNC(=O)c1ccccc1OCc1nc2ccccn2c1C#Cc1ccc(F)cc1] | N-(2-(dimethylamino)ethyl)-2-((3-((4-fluorophenyl)ethynyl)-imidazo[1,2-a]pyridin-2-yl)methoxy)benzamide |
| 96 | 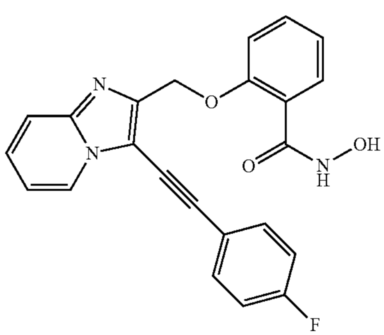 [SMILES: O=C(NO)c1ccccc1OCc1nc2ccccn2c1C#Cc1ccc(F)cc1] | 2-((3-((4-fluorophenyl)ethynyl)-imidazo[1,2-a]pyridin-2-yl)-methoxy)-N-hydroxybenzamide |

TABLE 1-continued

List of the molecules, the synthesis of which is exemplified

| No. | Chemical structure | Chemical name |
|---|---|---|
| 97 | 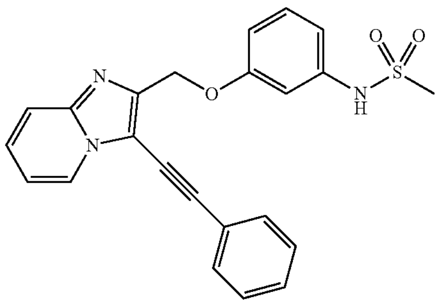 [SMILES: CS(=O)(=O)Nc1cccc(OCc2nc3ccccn3c2C#Cc2ccccc2)c1] | N-(3-((3-(phenylethynyl)imidazo[1,2-a]pyridin-2-yl)methoxy)-phenyl)methane-sulfonamide |
| 98 | 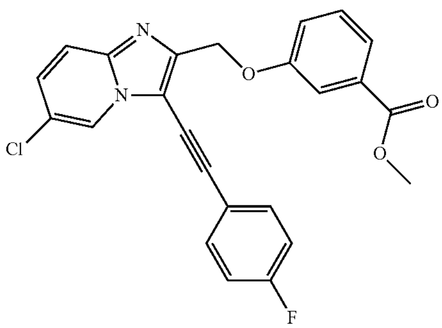 [SMILES: COC(=O)c1cccc(OCc2nc3ccc(Cl)cn3c2C#Cc2ccc(F)cc2)c1] | methyl 3-((6-chloro-3-((4-fluoro-phenyl)ethynyl)imidazo[1,2-a]pyridin-2-yl)methoxy)benzoate |
| 99 | 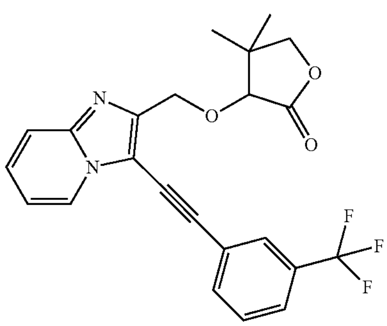 [SMILES: CC1(C)COC(=O)C1OCc1nc2ccccn2c1C#Cc1cccc(C(F)(F)F)c1] | 4,4-dimethyl-3-[[3-[2-[3-(trifluoromethyl)phenyl]ethynyl] imidazo[1,2-a]pyridin-2-yl]methoxy]-tetrahydrofuran-2-one |
| 100 | 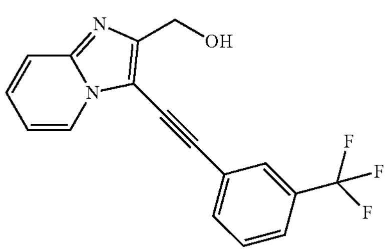 [SMILES: OCc1nc2ccccn2c1C#Cc1cccc(C(F)(F)F)c1] | [3-[2-[3-(trifluoromethyl)-phenyl]ethynyl]imidazo[1,2-a]pyridin-2-yl]methanol |
| 101 | 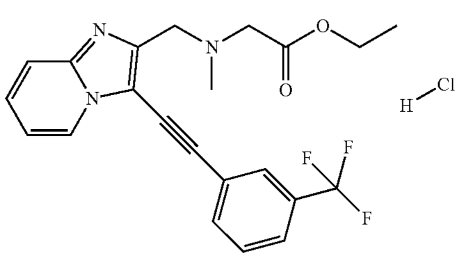 [SMILES: CCOC(=O)CN(C)Cc1nc2ccccn2c1C#Cc1cccc(C(F)(F)F)c1 ; Cl] | ethyl 2-[methyl-[[3-[2-[3-(trifluoromethyl)phenyl]ethynyl] imidazo[1,2-a]pyridin-2-yl]-methyl]amino]acetate hydrochloride |

TABLE 1-continued

List of the molecules, the synthesis of which is exemplified

| No. | Chemical structure | Chemical name |
|---|---|---|
| 102 | 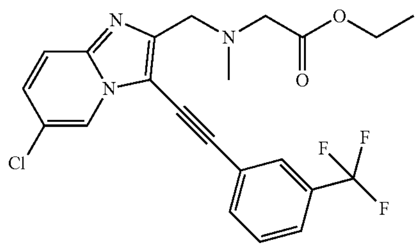 [SMILES: CCOC(=O)CN(C)Cc1nc2ccc(Cl)cn2c1C#Cc1cccc(C(F)(F)F)c1] | ethyl 2-[[6-chloro-3-[2-[3-(trifluoromethyl)phenyl]ethynyl]imidazo[1,2-a]pyridin-2-yl]methyl-methyl-amino]acetate |
| 103 | 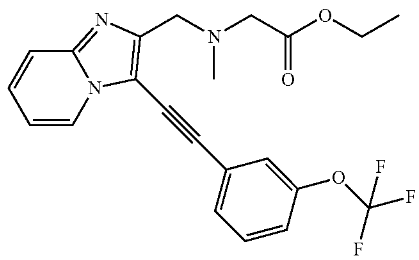 [SMILES: CCOC(=O)CN(C)Cc1nc2ccccn2c1C#Cc1cccc(OC(F)(F)F)c1] | ethyl 2-(methyl ((3-((3-(trifluoromethoxy)phenyl)ethynyl)imidazo[1,2-a]pyridin-2-yl)methyl)amino)acetate |
| 104 | 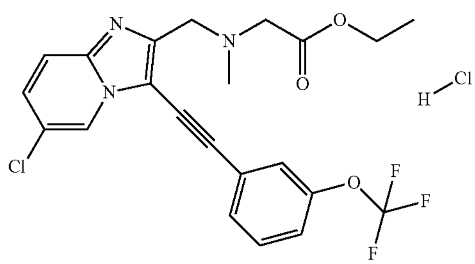 [SMILES: CCOC(=O)CN(C)Cc1nc2ccc(Cl)cn2c1C#Cc1cccc(OC(F)(F)F)c1 ; Cl] | ethyl 2-(((6-chloro-3-((3-(trifluoromethoxy)phenyl)ethynyl)imidazo[1,2-a]pyridin-2-yl)methyl)(methyl)amino)acetate hydrochloride |
| 105 | 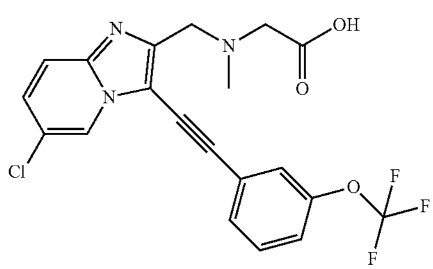 [SMILES: CN(CC(=O)O)Cc1nc2ccc(Cl)cn2c1C#Cc1cccc(OC(F)(F)F)c1] | 2-(((6-chloro-3-((3-(trifluoromethoxy)phenyl)ethynyl)imidazo[1,2-a]pyridin-2-yl)methyl)(methyl)amino)acetic acid |
| 106 | 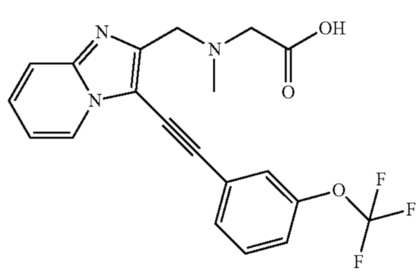 [SMILES: CN(CC(=O)O)Cc1nc2ccccn2c1C#Cc1cccc(OC(F)(F)F)c1] | 2-(methyl((3-((3-(trifluoromethoxy)phenyl)ethynyl)imidazo[1,2-a]pyridin-2-yl)methyl)amino)acetic acid |

TABLE 1-continued

List of the molecules, the synthesis of which is exemplified

| No. | Chemical structure | Chemical name |
|---|---|---|
| 107 | 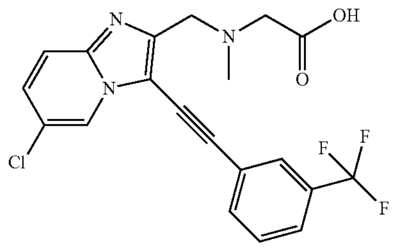 [SMILES: CN(CC(=O)O)Cc1nc2ccc(Cl)cn2c1C#Cc1cccc(C(F)(F)F)c1] | 2-(((6-chloro-3-((3-(trifluoromethyl)-phenyl)ethynyl)imidazo[1,2-a]pyridin-2-yl)methyl)(methyl)-amino) acetic acid |
| 108 | 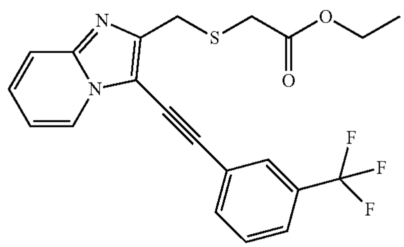 | ethyl 2-[[3-[2-[3-(trifluoromethyl)-phenyl]ethynyl]imidazo[1,2-a]pyridin-2-yl]methylsulfanyl]acetate |
| 109 | 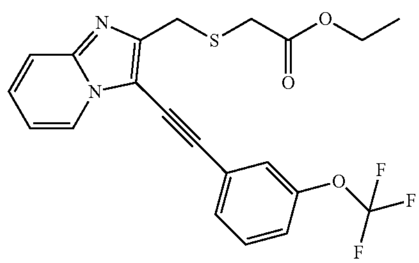 | ethyl 2-[[3-[2-[3-(trifluoromethoxy)-phenyl]ethynyl]imidazo[1,2-a]pyridin-2-yl]methylsulfanyl]acetate |
| 110 | 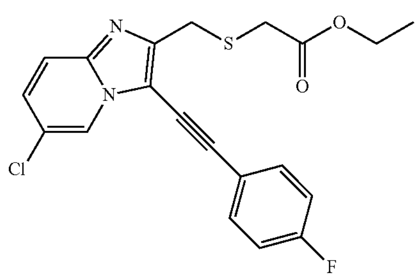 [SMILES: CCOC(=O)CSCc1nc2ccc(Cl)cn2c1C#Cc1ccc(F)cc1] | ethyl 2-[[6-chloro-3-[2-[4-(fluoro)-phenyl]ethynyl]imidazo[1,2-a]pyridin-2-yl]methylsulfanyl]acetate |
| 111 | 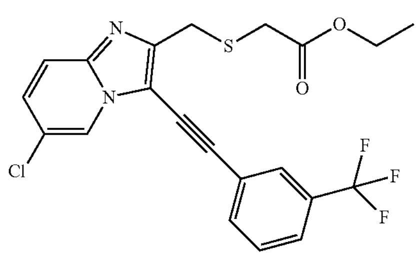 [SMILES: CCOC(=O)CSCc1nc2ccc(Cl)cn2c1C#Cc1cccc(C(F)(F)F)c1] | ethyl 2-[[6-chloro-3-[2-[3-(trifluoro-methyl)phenyl]ethynyl]imidazo[1,2-a]pyridin-2-yl]methylsulfanyl]acetate |
| 112 | 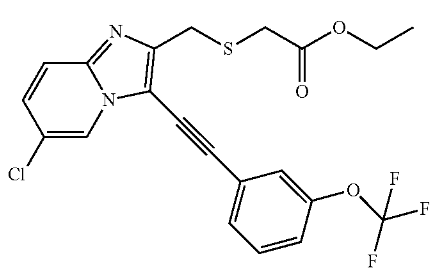 [SMILES: CCOC(=O)CSCc1nc2ccc(Cl)cn2c1C#Cc1cccc(OC(F)(F)F)c1] | ethyl 2-[[6-chloro-3-[2-[3-(trifluoromethoxy)phenyl]ethynyl]imidazo[1,2-a]pyridin-2-yl]methylsulfanyl]acetate |

TABLE 1-continued

List of the molecules, the synthesis of which is exemplified

| No. | Chemical structure | Chemical name |
|---|---|---|
| 113 | 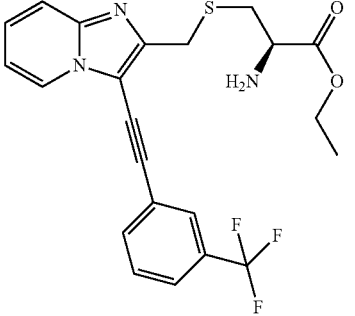 [SMILES: CCOC(=O)[C@@H](N)CSCc1nc2ccccn2c1C#Cc1cccc(C(F)(F)F)c1] | ethyl (2R)-2-amino-3-[[3-[2-[3-(trifluoromethyl)phenyl]ethynyl]imidazo[1,2-a]pyridin-2-yl]methyl-sulfanyl]propanoate |
| 114 | 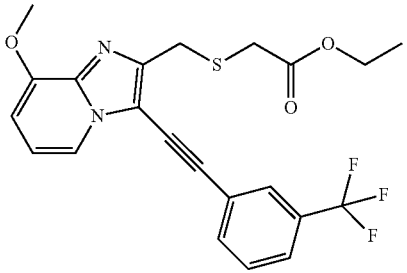 [SMILES: CCOC(=O)CSCc1nc2c(OC)cccn2c1C#Cc1cccc(C(F)(F)F)c1] | ethyl 2-[[8-methoxy-3-[2-[3-(trifluoromethyl)phenyl]ethynyl]imidazo[1,2-a]pyridin-2-yl]methyl-sulfanyl]acetate |
| 115 | 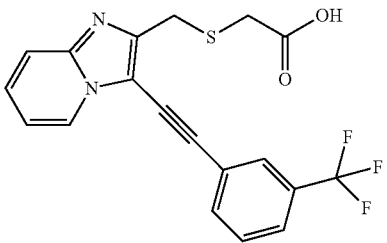 [SMILES: O=C(O)CSCc1nc2ccccn2c1C#Cc1cccc(C(F)(F)F)c1] | 2-[[3-[2-[3-(trifluoromethyl)phenyl]-ethynyl]imidazo[1,2-a]pyridin-2-yl]methylsulfanyl]acetic acid |
| 116 | 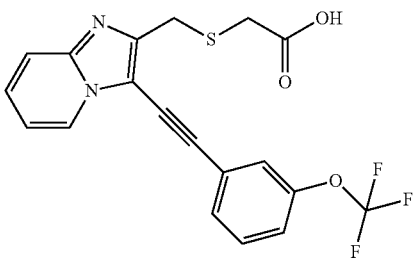 [SMILES: O=C(O)CSCc1nc2ccccn2c1C#Cc1cccc(OC(F)(F)F)c1] | 2-[[3-[2-[3-(trifluoromethoxy)-phenyl]ethynyl]imidazo[1,2-a]pyridin-2-yl]methylsulfanyl]acetic acid |
| 117 | 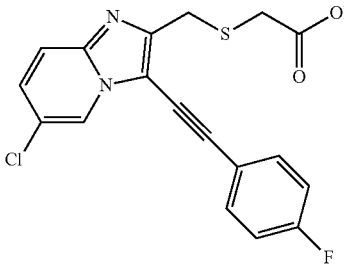 | 2-[[6-chloro-3-[2-(4-fluorophenyl)ethynyl]imidazo[1,2-a]pyridin-2-yl]methylsulfanyl]acetic acid |

TABLE 1-continued

List of the molecules, the synthesis of which is exemplified

| No. | Chemical structure | Chemical name |
|---|---|---|
| 118 | 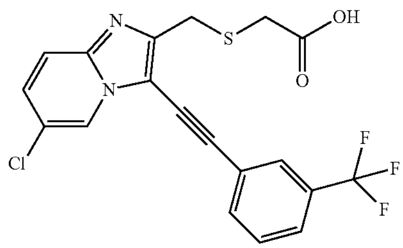 [SMILES: O=C(O)CSCc1nc2ccc(Cl)cn2c1C#Cc1cccc(C(F)(F)F)c1] | 2-[[6-chloro-3-[2-[3-(trifluoro-methyl)-phenyl]ethynyl]imidazo[1,2-a]pyridin-2-yl]methylsulfanyl]acetic acid |
| 119 | 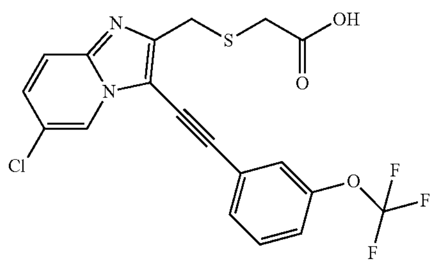 [SMILES: O=C(O)CSCc1nc2ccc(Cl)cn2c1C#Cc1cccc(OC(F)(F)F)c1] | 2-[[6-chloro-3-[2-[3-(trifluoromethoxy)phenyl]ethynyl]imidazo[1,2-a]pyridin-2-yl]methyl-sulfanyl]acetic acid |
| 120 | 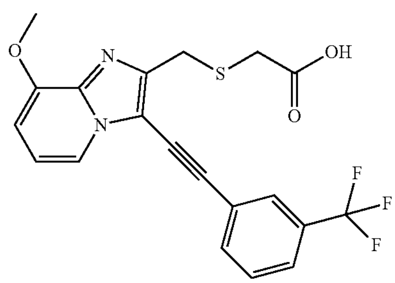 [SMILES: COc1cccn2c(C#Cc3cccc(C(F)(F)F)c3)c(CSCC(=O)O)nc12] | 2-[[8-methoxy-3-[2-[3-(trifluoromethyl)phenyl]ethynyl]imidazo[1,2-a]pyridin-2-yl]methylsulfanyl]acetic acid |
| 121 | 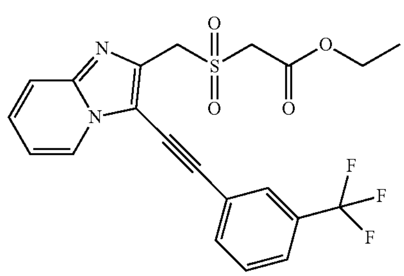 [SMILES: CCOC(=O)CS(=O)(=O)Cc1nc2ccccn2c1C#Cc1cccc(C(F)(F)F)c1] | ethyl 2-[[3-[2-[3-(trifluoromethyl)-phenyl]ethynyl]imidazo[1,2-a]pyridin-2-yl]methyl-sulfonyl]-acetate |
| 122 | 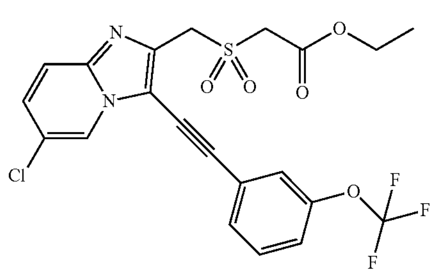 [SMILES: CCOC(=O)CS(=O)(=O)Cc1nc2ccc(Cl)cn2c1C#Cc1cccc(OC(F)(F)F)c1] | ethyl 2-[[6-chloro-3-[2-[3-(trifluoromethoxy)phenyl]ethynyl]imidazo[1,2-a]pyridin-2-yl]methyl-sulfonyl]acetate |

TABLE 1-continued

List of the molecules, the synthesis of which is exemplified

| No. | Chemical structure | Chemical name |
|---|---|---|
| 123 | 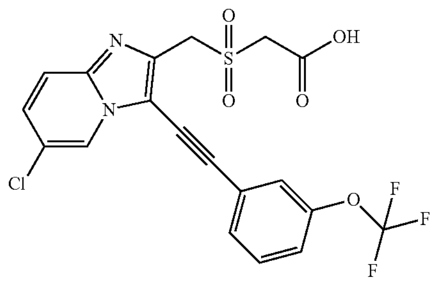 [SMILES: O=C(O)CS(=O)(=O)Cc1nc2ccc(Cl)cn2c1C#Cc1cccc(OC(F)(F)F)c1] | 2-[[6-chloro-3-[2-[3-(trifluoro-methoxy)phenyl]ethynyl]imidazo[1,2-a]pyridin-2-yl]methylsulfonyl]acetic acid |
| 124 | 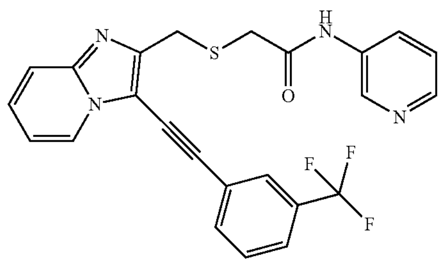 [SMILES: O=C(CSCc1nc2ccccn2c1C#Cc1cccc(C(F)(F)F)c1)Nc1cccnc1] | N-(3-pyridyl)-2-[[3-[2-[3-(trifluoromethyl)phenyl]ethynyl]imidazo[1,2-a]pyridin-2-yl]methylsulfanyl]acetamide |
| 125 | 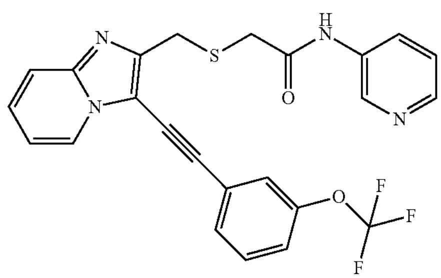 [SMILES: O=C(CSCc1nc2ccccn2c1C#Cc1cccc(OC(F)(F)F)c1)Nc1cccnc1] | N-(3-pyridyl)-2-[[3-[2-[3-(trifluoromethoxy)phenyl]ethynyl]imidazo[1,2-a]pyridin-2-yl]methoxy]acetamide |
| 126 | 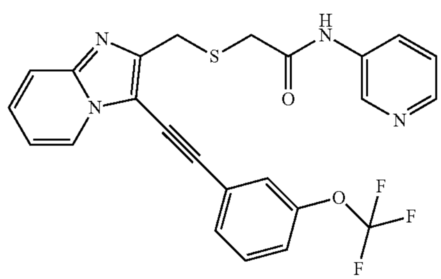 [SMILES: O=C(CSCc1nc2ccccn2c1C#Cc1cccc(OC(F)(F)F)c1)Nc1cccnc1] | N-(3-pyridyl)-2-[[3-[2-[3-(trifluoromethoxy)phenyl]ethynyl]imidazo[1,2-a]pyridin-2-yl]methylsulfanyl]acetamide |
| 127 | 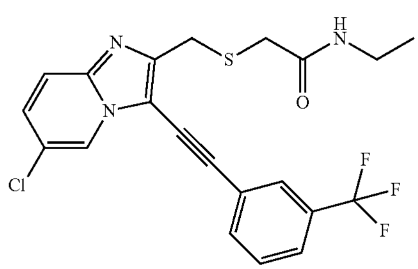 [SMILES: CCNC(=O)CSCc1nc2ccc(Cl)cn2c1C#Cc1cccc(C(F)(F)F)c1] | 2-[[6-chloro-3-[2-[3-(trifluoromethyl)phenyl]ethynyl]imidazo[1,2-a]pyridin-2-yl]methylsulfanyl]-N-ethyl-acetamide |

TABLE 1-continued

List of the molecules, the synthesis of which is exemplified

| No. | Chemical structure | Chemical name |
|-----|-------------------|---------------|
| 128 | 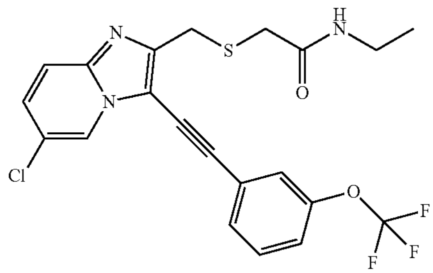 [SMILES: CCNC(=O)CSCc1nc2ccc(Cl)cn2c1C#Cc1cccc(OC(F)(F)F)c1] | 2-[[6-chloro-3-[2-[3-(trifluoromethoxy)phenyl]ethynyl]imidazo[1,2-a]pyridin-2-yl]methylsulfanyl]-N-ethyl-acetamide |
| 129 | 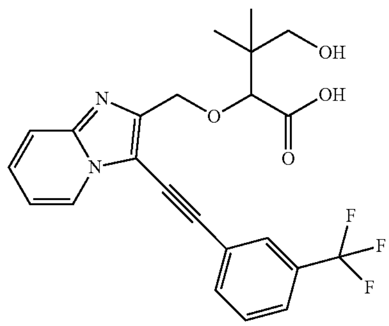 [SMILES: CC(C)(CO)C(OCc1nc2ccccn2c1C#Cc1cccc(C(F)(F)F)c1)C(=O)O] | 4-hydroxy-3,3-dimethyl-2-[[3-[2-[3-(trifluoromethyl)phenyl]ethynyl]imidazo[1,2-a]pyridin-2-yl]methoxy]butanoic acid |
| 130 | 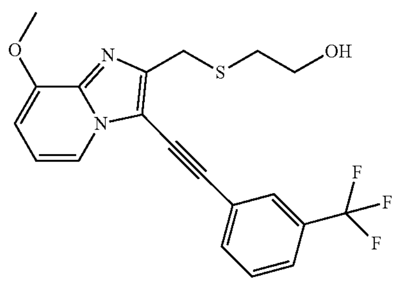 [SMILES: COc1cccn2c(C#Cc3cccc(C(F)(F)F)c3)c(CSCCO)nc12] | 2-[[8-methoxy-3-[2-[3-(trifluoromethyl)phenyl]ethynyl]imidazo[1,2-a]pyridin-2-yl]methylsulfanyl]ethanol |
| 131 | 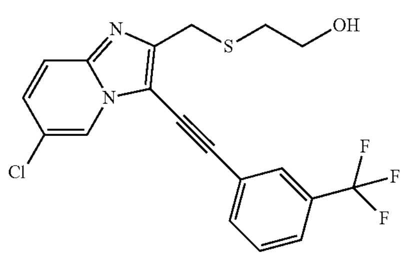 [SMILES: OCCSCc1nc2ccc(Cl)cn2c1C#Cc1cccc(C(F)(F)F)c1] | 2-[[6-chloro-3-[2-[3-(trifluoromethyl)phenyl]ethynyl]imidazo[1,2-a]pyridin-2-yl]methylsulfanyl]ethanol |
| 132 | 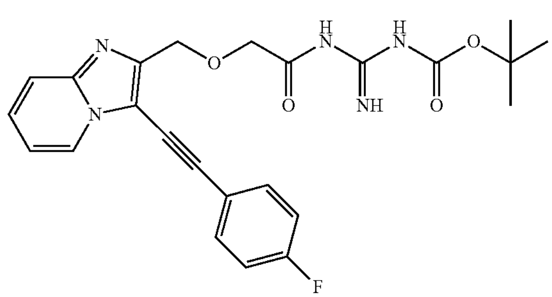 [SMILES: CC(C)(C)OC(=O)NC(=N)NC(=O)COCc1nc2ccccn2c1C#Cc1ccc(F)cc1] | tert-butyl N-[N-[2-[[3-[2-(4-fluoro-phenyl)ethynyl]imidazo[1,2-a]pyridin-2-yl]methoxy]acetyl]-carbamimidoyl]carbamate |

TABLE 1-continued

List of the molecules, the synthesis of which is exemplified

| No. | Chemical structure | Chemical name |
|---|---|---|
| 133 | 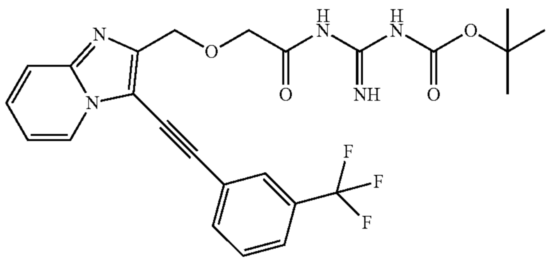 [SMILES: CC(C)(C)OC(=O)NC(=N)NC(=O)COCc1nc2ccccn2c1C#Cc1cccc(C(F)(F)F)c1] | tert-butyl N-[N-[2-[[3-[2-[3-(trifluoromethyl)phenyl]ethynyl]imidazo[1,2-a]pyridin-2-yl]methyl-sulfanyl]acetyl]carbamimidoyl]carbamate |
| 134 | 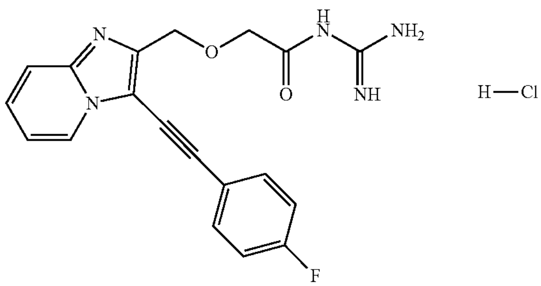 [SMILES: N=C(N)NC(=O)COCc1nc2ccccn2c1C#Cc1ccc(F)cc1 ; Cl] | N-carbamimidoyl-2-[[3-[2-(4-fluorophenyl)ethynyl]imidazo[1,2-a]pyridin-2-yl]methoxy]acetamide hydrochloride |
| 135 | 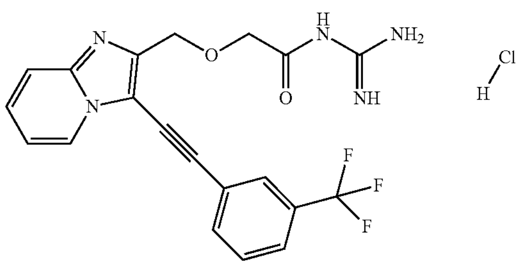 [SMILES: N=C(N)NC(=O)COCc1nc2ccccn2c1C#Cc1cccc(C(F)(F)F)c1 ; Cl] | N-carbamimidoyl-2-[[3-[2-[3-(trifluoromethyl)phenyl]ethynyl]imidazo[1,2-a]pyridin-2-yl]methyl-sulfanyl]acetamide hydrochloride |
| 136 | 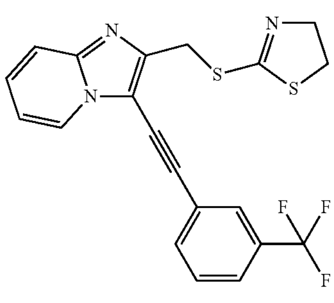 [SMILES: FC(F)(F)c1cccc(C#Cc2c(CSC3=NCCS3)nc3ccccn23)c1] | 2-((3-((3-(trifluoromethyl)phenyl)ethynyl)imidazo[1,2-a]pyridin-2-yl)methylthio)-4,5-dihydrothiazole |
| 137 | 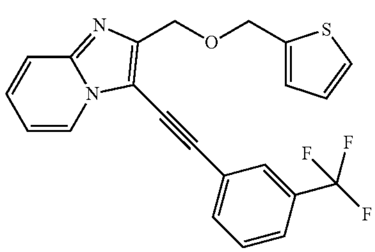 [SMILES: FC(F)(F)c1cccc(C#Cc2c(COCc3cccs3)nc3ccccn23)c1] | 2-((thiophen-2-ylmethoxy)methyl)-3-((3-(trifluoromethyl)phenyl)ethynyl)imidazo[1,2-a]pyridine |

TABLE 1-continued

List of the molecules, the synthesis of which is exemplified

| No. | Chemical structure | Chemical name |
|---|---|---|
| 138 | 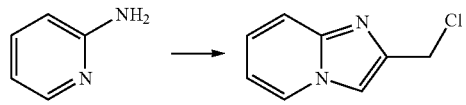 [SMILES: Nc1ccccn1 ; ClCc1cn2ccccc2n1] | 2-((pyridin-2-ylthio)methyl)-3-((3-(trifluoromethyl)phenyl)ethynyl)imidazo[1,2-a]pyridine |

Example 1

Preparation of Derivative No. 1: ethyl 2-((3-(phenylethynyl) imidazo[1,2-a]pyridin-2-yl)methoxy)acetate

Step 1: Preparation of 2-(chloromethyl)imidazo[1,2-a]pyridine 7.09 g (54.1 mmol) of 1,3-dichloroacetone were solubilised in 13 ml of DME, to this solution were added with magnetic stirring, 5 g (52.1 mmol) of 2-aminopyridine. The mixture was stirred at r.t. for 16 h. The solid formed was isolated by filtration and washed with 30 ml of diisopropyl ether. This yellow solid was suspended in 125 ml of absolute ethanol and the mixture was stirred with reflux for 2 h. The mixture was concentrated in vacuo and then the obtained residue was taken up in 150 ml of a mixture consisting of water and ice. The pH of the aqueous phase was basified up to pH 8-9 by adding a saturated NaHCO₃ aqueous solution. The aqueous phase was extracted with 3×100 ml of dichloromethane. The combined organic phases were washed with 200 ml of a saturated NaCl aqueous solution, dried on Na₂SO₄ which was then removed by filtration. The obtained filtrate was concentrated in vacuo. The crude residue was purified by flash chromatography on a silica gel cartridge (eluent: heptane/ethyl acetate gradient, from 50% to 40% of heptane, v/v). 4.77 g (yield=55%) of 2-(chloromethyl)imidazo[1,2-a]pyridine were obtained as a white solid. LC-MS: m/z=167 (MH⁺); UV purity at 254 nm=99%. ¹H NMR (300 MHz, DMSO) δ 8.52 (d, J=6.8 Hz, 1H), 7.99 (s, 1H), 7.51 (d, J=9.1 Hz, 1H), 7.32-7.16 (m, 1H), 6.89 (t, J=6.8 Hz, 1H), 4.84 (s, 2H)

Step 2: Preparation of 2-(imidazo[1,2-a]pyridin-2-ylmethoxy)acetic acid

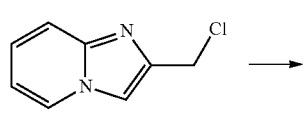

4.24 g (25.4 mmol) of 2-(chloromethyl)imidazo[1,2-a]pyridine were dissolved in 150 ml of tetrahydrofurane with magnetic stirring and then 4.2 g (28 mmol) of sodium iodide were added. The mixture was stirred at r.t. for 3 h. In another flask, 9.84 ml (101.8 mmol) of ethyl 2-hydroxyacetate were solubilized in 100 ml of tetrahydrofurane with magnetic stirring, and then the mixture was cooled to 0° C. and 4.072 g (101.8 mmol) of sodium hydride were added portionwise. The mixture was stirred 15 min at 0° C. and then the freshly prepared solution of 2-(iodomethyl)imidazo[1,2-a]pyridine in tetrahydrofurane was added drop wise within 15 min. The mixture was stirred at r.t. for 24 h before being filtered on silica (eluent: tetrahydrofurane 100%). The filtrate was concentrated in vacuo and directly purified by flash chromatography on a silica gel cartridge (eluent: dichloromethane/methanol gradient, from 100% to 70% of dichloromethane, v/v; and then washing the cartridge with 100% methanol). 3.62 g (yield=69%) of 2-(imidazo[1,2-a]pyridin-2-ylmethoxy)acetic acid were obtained as a beige solid. LC-MS: m/z=207 (MH⁺); UV purity at 254 nm=98%.

Step 3: Preparation of ethyl 2-(imidazo[1,2-a]pyridin-2-ylmethoxy)acetate

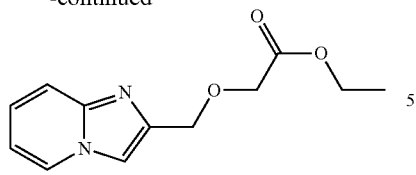

3.62 g (15.58 mmol) of 2-(imidazo[1,2-a]pyridin-2-yl-methoxy)acetic acid were solubilised with magnetic stirring in 100 ml of ethanol and 0.094 ml (1.758 mmol) of sulfuric acid were added. The mixture was stirred with reflux for 5 d. The reaction medium was concentrated in vacuo and directly purified by flash chromatography on a silica gel cartridge (eluent: ethyl acetate 100% and then dichloromethane/methanol, 9/1, v/v). The reaction medium was washed with 2×10 ml of water, and then extracted with 2×30 ml of ethyl acetate. The combined organic phases were washed with 30 ml of a saturated NaCl aqueous solution, dried on $Na_2SO_4$ which was then removed by filtration. The obtained filtrate was concentrated in vacuo. 0.162 mg (yield=91%) of isopropyl 2-((3-((4-fluorophenyl)ethynyl)imidazo[1,2-a]pyridin-2-yl)methoxy)acetate were obtained as a brown oil. MS: m/z=235 ($MH^+$). $^1$H NMR (300 MHz, DMSO) δ 8.52 (d, J=7.9 Hz, 1H), 7.91 (s, 1H), 7.50 (d, J=9.1 Hz, 1H), 7.30-7.13 (m, 1H), 6.87 (t, J=6.7 Hz, 1H), 4.65 (s, 2H), 4.20 (s, 2H), 4.12 (q, J=7.1 Hz, 2H), 1.19 (t, J=7.2 Hz, 3H).

Step 4: Preparation of ethyl 2-((3-iodoimidazo[1,2-a]pyridin-2-yl)methoxy)acetate

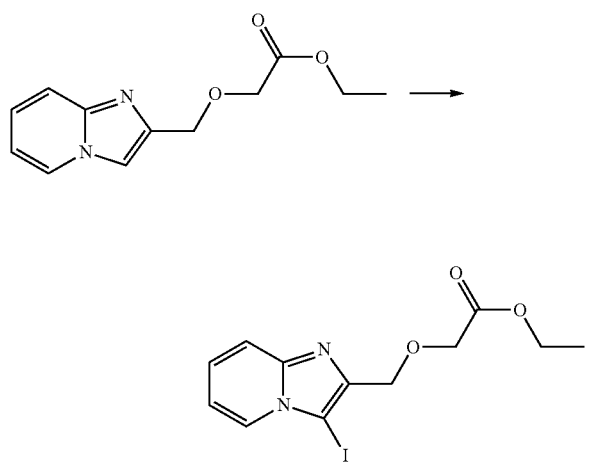

0.45 g (1.921 mmol) of ethyl 2-(imidazo[1,2-a]pyridin-2-ylmethoxy)acetate were solubilised in 6 ml of acetonitrile with magnetic stirring, to this solution were added 0.475 g (2.113 mmol) of N-iodosuccinimide. The mixture was stirred at r.t. for 16 h. A solid was removed by filtration and the obtained filtrate was concentrated in vacuo. The residue was triturated with 10 ml of diisopropyl ether and a precipitate was isolated by filtration. 0.465 g (yield=67%) ethyl 2-((3-iodoimidazo[1,2-a]pyridin-2-yl)methoxy)acetate were obtained as a yellow solid. LC-MS: m/z=361 ($MH^+$); UV purity at 254 nm=75%. $^1$H NMR (300 MHz, DMSO) δ 8.34 (d, J=6.9 Hz, 1H), 7.59 (d, J=8.1 Hz, 1H), 7.47-7.28 (m, 1H), 7.07 (d, J=5.7 Hz, 1H), 4.67 (s, 2H), 4.14 (t, J=10.7 Hz, 4H), 1.22 (d, J=1.9 Hz, 3H)

Step 5: Preparation of ethyl 2-((3-(phenylethynyl)imidazo[1,2-a]pyridin-2-yl)methoxy)acetate (Derivative Number 1)

In a flask placed under an argon flow, 0.1 g (0.278 mmol) of ethyl 2-((3-iodoimidazo[1,2-a]pyridin-2-yl)methoxy)acetate were solubilised in 0.3 ml of dimethylformamide with magnetic stirring.

To this solution, were added: 0.005 g (0.028 mmol) of copper iodide, 0.037 ml (0.333 mmol) of phenylacetylene and 0.3 ml (2.152 mmol) of triethylamine. The reaction medium was degassed with argon for 10 min before adding 0.025 g (0.028 mmol) of $Pd_2(dba)_3$. The mixture was stirred at r.t. for 16 h before being filtered on celite. The celite was washed with 20 ml of ethyl acetate, and then the filtrate was washed with 2×50 ml of water. After separation, the aqueous phase was extracted with 30 ml of ethyl acetate, the combined organic phases were washed with 30 ml of a saturated NaCl aqueous solution, dried on $Na_2SO_4$ which was then removed by filtration. The obtained filtrate was concentrated in vacuo. The crude residue was purified by flash chromatography on a silica gel cartridge (eluent: heptane/ethyl acetate, 1/1, v/v). 0.038 g (yield=41%) de ethyl 2-((3-(phenylethynyl)imidazo[1,2-a]pyridin-2-yl)methoxy)acetate were obtained as a pale yellow solid. LC-MS: m/z=335 ($MH^+$); UV purity at 254 nm=99%. $^1$H NMR (300 MHz, DMSO) δ 8.63 (d, J=5.6 Hz, 1H), 7.68 (d, J=8.0 Hz, 3H), 7.54-7.39 (m, 4H), 7.14 (t, J=6.8 Hz, 1H), 4.79 (s, 2H), 4.24 (s, 2H), 4.09 (q, J=7.1 Hz, 2H), 1.15 (t, J=7.1 Hz, 3H).

Derivatives numbers 2 to 26, 98 and 99 were obtained from ethyl 2-((3-iodoimidazo[1,2-a]pyridin-2-yl)methoxy)acetate according to the same procedure.

| No. | Molecular weight g/mol | Aspect | LCMS purity UV at 254 nm | Mass spectrometry MH+ | M-H+ | ¹H NMR (300 MHz, DMSO) δ |
|---|---|---|---|---|---|---|
| 2 | 348.40 | yellow oil | >99 | 349 | | 8.60 (d, J = 6.7 Hz, 1H), 7.67 (d, J = 9.0 Hz, 1H), 7.56 (d, J = 8.1 Hz, 2H), 7.49-7.38 (m, 1H), 7.28 (d, J = 7.9 Hz, 2H), 7.12 (t, J = 6.8 Hz, 1H), 4.77 (s, 2H), 4.23 (s, 2H), 4.09 (q, J = 7.1 Hz, 2H), 2.35 (s, 3H), 1.14 (t, J = 7.1 Hz, 3H). |
| 3 | 352.36 | pale grey solid | >99 | 353 | | 8.63 (d, J = 6.8 Hz, 1H), 7.80-7.62 (m, 3H), 7.50-7.39 (m, 1H), 7.33 (t, J = 8.9 Hz, 2H), 7.12 (t, J = 7.3 Hz, 1H), 4.77 (s, 2H), 4.22 (s, 2H), 4.08 (q, J = 7.1 Hz, 2H), 1.13 (t, J = 7.1 Hz, 3H). |
| 4 | 364.39 | brown oil | >99 | 365 | | 8.59 (d, J = 6.7 Hz, 1H), 7.77-7.56 (m, 3H), 7.50-7.36 (m, 1H), 7.22-6.97 (m, 3H), 4.77 (s, 2H), 4.23 (s, 2H), 4.18-4.02 (m, 2H), 1.15 (t, J = 7.1 Hz, 3H). |
| 5 | 379.37 | yellow solid | >99 | 380 | | 8.77 (d, J = 6.7 Hz, 1H), 8.33 (d, J = 9.0 Hz, 2H), 7.95 (d, J = 9.0 Hz, 2H), 7.72 (d, J = 9.0 Hz, 1H), 7.56-7.44 (m, 1H), 7.18 (t, J = 6.8 Hz, 1H), 4.82 (s, 2H), 4.27 (s, 2H), 4.11 (q, J = 7.1 Hz, 2H), 1.16 (t, J = 7.1 Hz, 3H). |
| 6 | 402.37 | brown solid | >99 | 403 | | 8.73 (d, J = 6.7 Hz, 1H), 7.89 (q, J = 8.4 Hz, 4H), 7.72 (d, J = 9.0 Hz, 1H), 7.54-7.42 (m, 1H), 7.18 (t, J = 6.3 Hz, 1H), 4.82 (s, 2H), 4.27 (s, 2H), 4.12 (q, J = 7.1 Hz, 2H), 1.16 (t, J = 7.1 Hz, 3H). |
| 7 | 402.37 | brown solid | 98.8 | 403 | | 8.76 (d, J = 6.7 Hz, 1H), 8.11 (s, 1H), 7.97 (d, J = 7.6 Hz, 1H), 7.79 (d, J = 7.9 Hz, 1H), 7.75-7.64 (m, 2H), 7.51-7.41 (m, 1H), 7.15 (t, J = 6.3 Hz, 1H), 4.80 (s, 2H), 4.25 (s, 2H), 4.09 (q, J = 7.1 Hz, 2H), 1.14 (t, J = 7.1 Hz, 3H). |
| 8 | 335.36 | pale yellow solid | >99 | 336 | | 8.88 (d, J = 1.4 Hz, 1H), 8.69 (d, J = 6.8 Hz, 1H), 8.60 (dd, J = 4.8, 1.5 Hz, 1H), 8.09 (dt, J = 7.9, 1.9 Hz, 1H), 7.70 (d, J = 9.0 Hz, 1H), 7.56-7.41 (m, 2H), 7.15 (td, J = 6.8, 1.0 Hz, 1H), 4.79 (s, 2H), 4.25 (s, 2H), 4.06 (s, 2H), 1.14 (t, J = 7.1 Hz, 3H). |
| 9 | 340.40 | brown solid | >99 | 341 | | 8.57 (d, J = 6.7 Hz, 1H), 8.02 (dd, J = 2.9, 1.1 Hz, 1H), 7.78-7.63 (m, 2H), 7.50-7.34 (m, 2H), 7.13 (t, J = 6.8 Hz, 1H), 4.76 (s, 2H), 4.23 (s, 2H), 4.10 (q, J = 7.1 Hz, 2H), 1.16 (t, J = 7.1 Hz, 3H). |
| 10 | 370.35 | Solid | >99 | 371 | | 8.68 (d, J = 6.8 Hz, 1H), 7.96-7.76 (m, 1H), 7.69 (d, J = 9.0 Hz, 1H), 7.63-7.52 (m, 2H), 7.52-7.39 (m, 1H), 7.14 (td, J = 6.8, 1.1 Hz, 1H), 4.78 (s, 2H), 4.24 (s, 2H), 4.10 (q, J = 7.1 Hz, 2H), 1.15 (t, J = 7.1 Hz, 3H). |

-continued

| No. | Molecular weight g/mol | Aspect | LCMS purity UV at 254 nm | Mass spectrometry MH+ | M-H+ | ¹H NMR (300 MHz, DMSO) δ |
|---|---|---|---|---|---|---|
| 11 | 436.36 | Solid | 97.3 | 437 | | 8.71 (d, J = 6.7 Hz, 1H), 7.93 (dd, J = 11.1, 1.8 Hz, 1H), 7.79-7.54 (m, 3H), 7.54-7.36 (m, 1H), 7.16 (td, J = 6.8, 1.1 Hz, 1H), 4.79 (s, 2H), 4.25 (s, 2H), 4.10 (q, J = 7.1 Hz, 2H), 1.15 (t, J = 7.1 Hz, 3H). |
| 12 | 364.40 | brown oil | >99 | 365 | | 8.58 (d, J = 6.7 Hz, 1H), 7.62 (d, J = 9.0 Hz, 1H), 7.45-7.26 (m, 2H), 7.18 (t, J = 4.2 Hz, 2H), 7.08 (t, J = 6.6 Hz, 1H), 7.00-6.90 (m, 1H), 4.72 (s, 2H), 4.18 (s, 2H), 4.04 (q, J = 7.1 Hz, 2H), 3.76 (s, 3H), 1.09 (t, J = 7.1 Hz, 3H). |
| 13 | 350.37 | brown solid | >99 | 351 | 349 | 9.75 (s, 1H), 8.58 (d, J = 6.8 Hz, 1H), 7.68 (d, J = 9.0 Hz, 1H), 7.53-7.35 (m, 1H), 7.26 (t, J = 7.9 Hz, 1H), 7.12 (ddd, J = 8.9, 7.3, 1.2 Hz, 2H), 7.05-6.98 (m, 1H), 6.85 (ddd, J = 8.2, 2.4, 0.9 Hz, 1H), 4.77 (s, 2H), 4.23 (s, 2H), 4.10 (q, J = 7.1 Hz, 2H), 1.15 (t, J = 7.1 Hz, 3H). |
| 14 | 359.38 | solid | 98.9 | 360 | | 8.68 (d, J = 6.7 Hz, 1H), 8.19 (t, J = 1.4 Hz, 1H), 7.97-7.89 (m, 1H), 7.89-7.78 (m, 1H), 7.63 (dd, J = 13.3, 5.4 Hz, 2H), 7.48-7.35 (m, 1H), 7.08 (dd, J = 16.4, 9.7 Hz, 1H), 4.74 (s, 2H), 4.20 (s, 2H), 4.06 (p, J = 7.0 Hz, 2H), 1.16-1.07 (m, 3H). |
| 15 | 373.41 | brown oil | 97.7 | 374 | | 8.64 (d, J = 6.5 Hz, 1H), 7.70 (d, J = 8.3 Hz, 3H), 7.45 (d, J = 8.4 Hz, 3H), 7.14 (t, J = 6.8 Hz, 1H), 4.78 (s, 2H), 4.24 (s, 2H), 4.09 (dd, J = 13.4, 6.3 Hz, 4H), 1.15 (t, J = 7.1 Hz, 3H). |
| 16 | 378.38 | beige solid | 93.8 | 379 | 377 | 13.28 (s, 1H), 8.72 (d, J = 6.8 Hz, 1H), 8.21 (d, J = 1.4 Hz, 1H), 8.07-7.85 (m, 2H), 7.78-7.54 (m, 2H), 7.54-7.33 (m, 1H), 7.15 (td, J = 6.8, 1.1 Hz, 1H), 4.80 (s, 2H), 4.26 (d, J = 8.7 Hz, 2H), 4.11 (q, J = 7.1 Hz, 2H), 1.15 (t, J = 7.1 Hz, 3H). |
| 17 | 418.37 | beige solid | 96 | 419 | | 8.65 (d, J = 6.7 Hz, 1H), 7.87-7.74 (m, 2H), 7.68 (d, J = 9.0 Hz, 1H), 7.55-7.42 (m, 3H), 7.14 (td, J = 6.8, 1.0 Hz, 1H), 4.78 (s, 2H), 4.23 (s, 2H), 4.08 (q, J = 7.1 Hz, 2H), 1.13 (t, J = 7.1 Hz, 3H). |
| 18 | 418.37 | yellow oil | >99 | 419 | | 8.71 (dd, J = 5.8, 1.0 Hz, 1H), 7.80-7.66 (m, 3H), 7.60 (t, J = 8.0 Hz, 1H), 7.54-7.39 (m, 2H), 7.15 (td, J = 6.8, 1.1 Hz, 1H), 4.79 (s, 2H), 4.24 (s, 2H), 4.09 (q, J = 7.1 Hz, 2H), 1.14 (t, J = 7.1 Hz, 3H). |

-continued

| No. | Molecular weight g/mol | Aspect | LCMS purity UV at 254 nm | Mass spectrometry MH+ | M-H+ | ¹H NMR (300 MHz, DMSO) δ |
|---|---|---|---|---|---|---|
| 19 | 391.42 | yellow oil | 95.1 | 392 | 390 | 10.09 (s, 1H), 8.56 (d, J = 6.8 Hz, 1H), 7.90 (s, 1H), 7.68 (d, J = 9.1 Hz, 1H), 7.56 (d, J = 7.8 Hz, 1H), 7.52-7.26 (m, 3H), 7.14 (t, J = 6.8 Hz, 1H), 4.77 (s, 2H), 4.22 (s, 2H), 4.09 (q, J = 7.1 Hz, 2H), 2.06 (s, 3H), 1.14 (t, J = 7.1 Hz, 3H). |
| 20 | 400.38 | solid | 96.9 | 401 | | 8.68 (d, J = 6.8 Hz, 1H), 7.69 (d, J = 9.0 Hz, 1H), 7.60-7.40 (m, 4H), 7.32 (s, 1H), 7.30-7.22 (m, 1H), 7.15 (td, J = 6.8, 1.1 Hz, 1H), 4.79 (s, 2H), 4.24 (s, 2H), 4.13-4.05 (m, 2H), 1.15 (t, J = 7.1 Hz, 3H). |
| 21 | 394.42 | brown oil | >99 | 395 | | 8.60 (s, 1H), 7.64 (s, 1H), 7.38 (s, 1H), 7.18 (d, J = 6.9 Hz, 2H), 7.06 (t, J = 6.6 Hz, 1H), 6.98 (d, J = 8.9 Hz, 1H), 4.69 (d, J = 17.6 Hz, 2H), 4.25 (d, J = 31.2 Hz, 2H), 4.04 (q, J = 7.1 Hz, 2H), 3.75 (d, J = 4.6 Hz, 6H), 1.09 (t, J = 7.1 Hz, 3H). |
| 22 | 377.44 | Solid | >99 | 378 | | 8.52 (d, J = 6.7 Hz, 1H), 7.64 (d, J = 8.9 Hz, 1H), 7.52-7.33 (m, 3H), 7.09 (t, J = 6.7 Hz, 1H), 6.75 (d, J = 9.0 Hz, 2H), 4.74 (s, 2H), 4.21 (s, 2H), 4.09 (q, J = 7.1 Hz, 2H), 2.97 (s, 6H), 1.15 (t, J = 7.1 Hz, 3H). |
| 23 | 352.36 | brown oil | >99 | 353 | | 8.68 (d, J = 6.7 Hz, 1H), 7.69 (d, J = 9.0 Hz, 1H), 7.64-7.39 (m, 4H), 7.37-7.22 (m, 1H), 7.14 (t, J = 6.5 Hz, 1H), 4.79 (s, 2H), 4.24 (s, 2H), 4.10 (q, J = 7.1 Hz, 2H), 1.15 (t, J = 7.1 Hz, 3H). |
| 24 | 364.40 | brown oil | >99 | 365 | | 8.50 (d, J = 6.8 Hz, 1H), 7.68 (d, J = 9.0 Hz, 1H), 7.58 (dd, J = 7.6, 1.7 Hz, 1H), 7.49-7.39 (m, 2H), 7.16 (ddd, J = 8.2, 6.0, 2.6 Hz, 2H), 7.02 (td, J = 7.5, 0.8 Hz, 1H), 4.76 (s, 2H), 4.24 (s, 2H), 4.09 (q, J = 7.1 Hz, 2H), 3.92 (s, 3H), 1.14 (t, J = 7.1 Hz, 3H). |
| 25 | 352.36 | brown oil | 98.7 | 353 | | 8.56 (d, J = 6.6 Hz, 1H), 7.85-7.65 (m, 2H), 7.61-7.47 (m, 2H), 7.43 (dd, J = 9.6, 8.8 Hz, 1H), 7.39-7.32 (m, 1H), 7.18 (t, J = 6.8 Hz, 1H), 4.79 (s, 2H), 4.24 (s, 2H), 4.10 (q, J = 7.1 Hz, 2H), 1.15 (t, J = 7.1 Hz, 3H). |
| 26 | 402.37 | brown oil | 95 | 403 | | 8.60 (s, 1H), 7.96 (d, J = 7.6 Hz, 1H), 7.74 (ddd, J = 43.4, 18.7, 7.7 Hz, 4H), 7.50 (s, 1H), 7.22 (t, J = 6.5 Hz, 1H), 4.79 (s, 2H), 4.26 (s, 2H), 4.10 (q, J = 7.0 Hz, 2H), 1.15 (t, J = 7.1 Hz, 3H). |
| 98 | 434.85 | beige solid | 99 | 435 | | 8.87 (d, J = 1.7 Hz, 1H), 7.84-7.72 (m, 3H), 7.62-7.29 (m, 7H), 5.40 (s, 2H), 3.79 (s, 3H). |

-continued

| No. | Molecular weight g/mol | Aspect | LCMS purity UV at 254 nm | Mass spectrometry MH+ | M-H+ | $^1$H NMR (300 MHz, DMSO) δ |
|---|---|---|---|---|---|---|
| 99 | 428.40 | brown solid | 99 | 429 | | 8.77 (d, J = 6.6 Hz, 1H), 8.08 (s, 1H), 7.94 (d, J = 7.6 Hz, 1H), 7.79 (d, J = 7.9 Hz, 1H), 7.71 (t, J = 7.7 Hz, 2H), 7.53-7.41 (m, 1H), 7.16 (t, J = 6.8 Hz, 1H), 5.13 (d, J = 11.9 Hz, 1H), 4.95 (d, J = 11.8 Hz, 1H), 4.30 (s, 1H), 3.99-3.90 (m, 2H), 1.06 (s, 3H), 0.96 (s, 3H) |

Example 2

Preparation of Derivative No. 27: 2-((3-((3-cyanophenyl)ethynyl)imidazo[1,2-a]pyridin-2-yl)methoxy) acetic acid

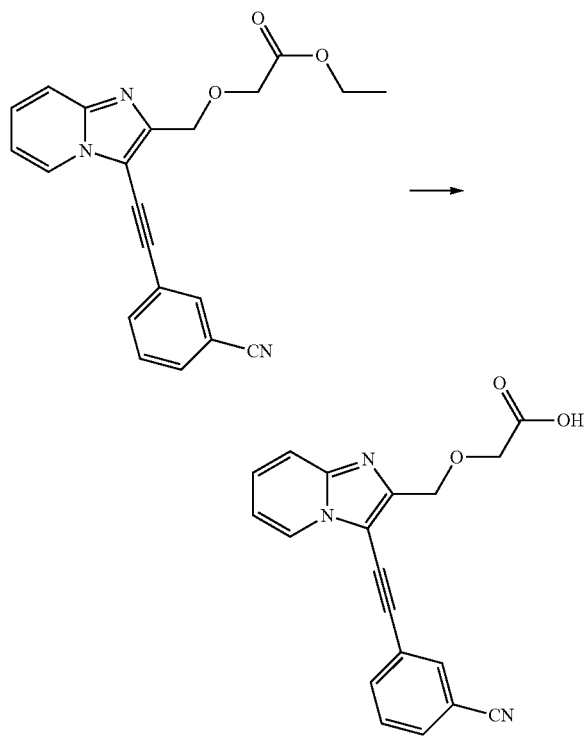

0.05 g (0.139 mmol) of ethyl 2-((3-((3-cyanophenyl)ethynyl)imidazo[1,2-a]pyridin-2-yl)methoxy) acetate were solubilized with magnetic stirring in 4 ml of an ethanol/tetrahydrofurane (1/1, v/v) mixture and then 0.167 ml (0.167 mmol) of a 1N NaOH aqueous solution were added. The mixture was stirred at r.t. for 16 h before adding 20 ml of water and then 0.016 ml (0.278 mmol) of acetic acid. The aqueous phase was extracted with 3×20 ml of ethyl acetate. The combined organic phases were dried on $Na_2SO_4$ which was then removed by filtration. The obtained filtrate was concentrated in vacuo. 0.042 g (yield=91%) of 2-((3-((3-cyanophenyl)ethynyl)imidazo[1,2-a]pyridin-2-yl)methoxy) acetic acid were obtained as a pale yellow solid. LC-MS: m/z=332 (MH$^+$); UV purity at 254 nm=99%. $^1$H NMR (300 MHz, DMSO) δ 12.70 (s, 1H), 8.73 (d, J=6.7 Hz, 1H), 8.22 (t, J=1.3 Hz, 1H), 8.07-7.94 (m, 1H), 7.94-7.78 (m, 1H), 7.78-7.55 (m, 2H), 7.54-7.38 (m, 1H), 7.15 (td, J=6.8, 0.9 Hz, 1H), 4.79 (s, 2H), 4.15 (s, 2H).

Derivatives numbers 28 to 44 were prepared according to the same procedure.

| No. | Molecular weight g/mol | Aspect | LCMS purity UV at 254 nm | Mass spectrometry MH+ | M-H+ | $^1$H NMR (300 MHz, DMSO) δ |
|---|---|---|---|---|---|---|
| 28 | 349.38 | Solid | 97.3 | 350 | | 8.52 (d, J = 6.8 Hz, 1H), 7.64 (d, J = 9.0 Hz, 1H), 7.46 (d, J = 8.9 Hz, 2H), 7.43-7.33 (m, 1H), 7.09 (td, J = 6.8, 1.1 Hz, 1H), 6.74 (d, J = 9.0 Hz, 2H), 4.74 (s, 2H), 4.12 (s, 2H), 2.97 (s, 6H). |

-continued

| No. | Molecular weight g/mol | Aspect | LCMS purity UV at 254 nm | Mass spectrometry MH+ | M-H+ | ¹H NMR (300 MHz, DMSO) δ |
|---|---|---|---|---|---|---|
| 29 | 390.31 | Solid | >99 | 391 | 389 | 12.68 (s, 1H), 8.72 (d, J = 6.7 Hz, 1H), 7.83-7.65 (m, 3H), 7.60 (t, J = 8.0 Hz, 1H), 7.46 (t, J = 7.8 Hz, 2H), 7.15 (t, J = 6.7 Hz, 1H), 4.79 (s, 2H), 4.15 (s, 2H). |
| 30 | 336.34 | Solid | >99 | 337 | 335 | 12.70 (s, 1H), 8.65 (d, J = 6.7 Hz, 1H), 7.69 (d, J = 9.0 Hz, 1H), 7.54-7.33 (m, 2H), 7.26 (dd, J = 4.1, 2.6 Hz, 2H), 7.15 (t, J = 6.7 Hz, 1H), 7.02 (dd, J = 7.9, 2.0 Hz, 1H), 4.79 (s, 2H), 4.16 (s, 2H), 3.83 (s, 3H). |
| 31 | 350.33 | Solid | >99 | | 349 | 13.00-11.49 (m, 1H), 9.77 (s, 1H), 8.59 (d, J = 6.7 Hz, 1H), 7.68 (d, J = 9.0 Hz, 1H), 7.51-7.39 (m, 1H), 7.26 (t, J = 7.9 Hz, 1H), 7.20-7.00 (m, 3H), 6.86 (ddd, J = 8.2, 2.4, 0.9 Hz, 1H), 4.77 (s, 2H), 4.14 (s, 2H). |
| 32 | 390.31 | Solid | 94 | | 389 | 12.53 (s, 1H), 8.62 (t, J = 9.6 Hz, 1H), 7.81-7.73 (m, 2H), 7.61 (t, J = 7.9 Hz, 1H), 7.44-7.36 (m, 3H), 7.15-7.02 (m, 1H), 4.71 (d, J = 3.8 Hz, 2H), 4.06 (d, J = 12.9 Hz, 2H). |
| 33 | 322.32 | Solid | 92.7 | | 321 | 9.75 (s, 1H), 8.57 (d, J = 6.7 Hz, 1H), 7.67 (d, J = 9.0 Hz, 1H), 7.49-7.37 (m, 1H), 7.25 (t, J = 7.9 Hz, 1H), 7.18-7.07 (m, 2H), 7.07-6.97 (m, 1H), 6.84 (dd, J = 8.2, 1.5 Hz, 1H), 4.76 (s, 2H), 4.10 (s, 2H). |
| 34 | 363.37 | solid | 95.3 | | 362 | 12.60 (s, 1H), 10.08 (s, 1H), 8.56 (d, J = 6.7 Hz, 1H), 7.89 (s, 1H), 7.68 (d, J = 9.0 Hz, 1H), 7.58 (d, J = 7.5 Hz, 1H), 7.52-7.33 (m, 3H), 7.14 (t, J = 6.5 Hz, 1H), 4.77 (s, 2H), 4.14 (s, 2H), 2.06 (s, 3H). |
| 35 | 372.32 | solid | >99 | 373 | 371 | 12.68 (s, 1H), 8.68 (d, J = 6.7 Hz, 1H), 7.69 (d, J = 9.0 Hz, 1H), 7.63-7.39 (m, 4H), 7.32 (s, 1H), 7.29-7.19 (m, 1H), 7.19-7.11 (m, 1H), 7.08 (s, 1H), 4.78 (s, 1H), 4.15 (s, 2H). |
| 36 | 366.37 | solid | >99 | 367 | | 12.67 (s, 8H), 8.60 (d, J = 6.3 Hz, 10H), 7.66 (d, J = 9.0 Hz, 13H), 7.52-7.34 (m, 16H), 7.24 (s, 23H), 7.12 (t, J = 6.6 Hz, 12H), 7.03 (d, J = 8.8 Hz, 12H), 4.76 (s, 20H), 4.15 (s, 21H), 3.81 (d, J = 3.9 Hz, 60H). |
| 37 | 345.35 | Solid | 94.6 | 346 | 344 | 8.63 (d, J = 6.7 Hz, 1H), 7.69 (t, J = 8.3 Hz, 3H), 7.45 (t, J = 6.4 Hz, 3H), 7.14 (t, J = 6.3 Hz, 1H), 4.78 (s, 2H), 4.13 (d, J = 4.8 Hz, 4H). |
| 38 | 342.30 | brown solid | >99 | 343 | 341 | 12.38 (s, 1H), δ 8.69 (s, 1H), 7.84 (dd, J = 11.1, 8.0 Hz, 1H), 7.69 (d, J = |

-continued

| No. | Molecular weight g/mol | Aspect | LCMS purity UV at 254 nm | MH+ | M-H+ | $^1$H NMR (300 MHz, DMSO) δ |
|---|---|---|---|---|---|---|
| | | | | | | 8.3 Hz, 1H), 7.63-7.51 (m, 2H), 7.46 (s, 1H), 7.15 (t, J = 6.2 Hz, 1H), 4.78 (s, 2H), 4.16 (s, 2H). |
| 39 | 408.30 | brown solid | >99 | 409 | 407 | 12.66 (s, 1H) 8.70 (d, J = 6.6 Hz, 1H), 7.97-7.83 (m, 1H), 7.66 (q, J = 9.1 Hz, 3H), 7.47 (t, J = 7.8 Hz, 1H), 7.15 (t, J = 6.7 Hz, 1H), 4.79 (s, 2H), 4.15 (s, 2H). |
| 40 | 324.31 | brown solid | >99 | 325 | 323 | 12.62 (s, 1H) 8.67 (d, J = 6.8 Hz, 1H), 7.68 (d, J = 9.0 Hz, 1H), 7.65-7.39 (m, 4H), 7.35-7.23 (m, 1H), 7.14 (td, J = 6.8, 1.0 Hz, 1H), 4.78 (s, 2H), 4.15 (s, 2H). |
| 41 | 336.34 | brown solid | 99 | 337 | 335 | 12.63 (s, 1H) 8.58-8.44 (m, 1H), 7.68 (d, J = 9.0 Hz, 1H), 7.59 (dd, J = 7.6, 1.7 Hz, 1H), 7.51-7.36 (m, 2H), 7.16 (ddd, J = 8.2, 6.1, 2.7 Hz, 2H), 7.02 (td, J = 7.5, 0.9 Hz, 1H), 4.77 (s, 2H), 4.16 (s, 2H), 3.93 (s, 3H). |
| 42 | 324.31 | brown solid | >99 | 325 | 323 | 8.52 (d, J = 6.7 Hz, 1H), 7.74 (ddd, J = 22.0, 11.0, 5.3 Hz, 2H), 7.58-7.25 (m, 4H), 7.16 (t, J = 6.7 Hz, 1H), 4.78 (s, 2H), 4.13 (s, 2H).1H under H2O peak (3, 3) |
| 43 | 374.31 | yellow oil | >99 | 375 | 373 | 12.65 (s, 1H), 8.52 (s, 1H), 7.96 (d, J = 7.0 Hz, 1H), 7.86 (d, J = 7.8 Hz, 1H), 7.76 (t, J = 7.4 Hz, 2H), 7.61 (d, J = 7.6 Hz, 1H), 7.49 (s, 1H), 7.21 (s, 1H), 4.78 (s, 2H), 4.15 (s, 2H). |
| 44 | 324.31 | Solid | 99 | 325 | 323 | 12.75 (s, 1H), 8.65 (d, J = 6.7 Hz, 1H), 7.93-7.60 (m, 3H), 7.47 (m, 1H), 7.34 (t, J = 8.9 Hz, 2H), 7.20-7.03 (m, 1H), 4.78 (s, 2H), 4.15 (s, 2H). |

Example 3

Preparation of Derivative No. 45: sodium 2-((3-(phenyl ethynyl)imidazo[1,2-a]pyridin-2-yl)methoxy)acetate

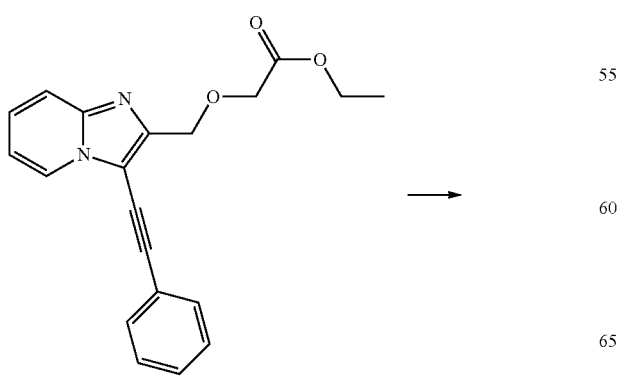

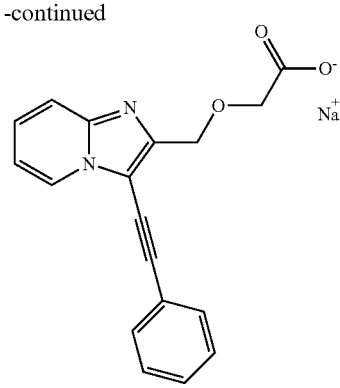

0.061 g (0.182 mmol) of ethyl 2-((3-(phenylethynyl)imidazo[1,2-a]pyridin-2-yl)methoxy)acetate were solubilised with magnetic stirring in 3 ml of a mixture consisting of methanol and tetrahydrofurane (1/1, v/v) and then 0.173 ml (0.173 mmol) of a 1N NaOH aqueous solution were added. The mixture was stirred at r.t. for 2 d before being concentrated in vacuo. The crude residue was triturated in 3 ml of diisopropyl ether, the obtained solid was isolated by filtration and dried under a vacuum bell jar in order to obtain 0.027 g (yield=45%) of sodium 2-((3-(phenyl ethynyl)imidazo[1,2-a]pyridin-2-yl)methoxy)acetate. LC-MS: m/z=307 (MH+); UV purity at 254 nm=99%. ¹H NMR (300 MHz, DMSO) δ 8.62 (d, J=6.7 Hz, 1H), 7.79-7.58 (m, 3H), 7.45 (dd, J=8.8, 7.2 Hz, 4H), 7.13 (t, J=6.5 Hz, 1H), 4.74 (s, 2H), 3.70 (s, 2H)

Derivatives numbers 46 to 53 were prepared according to the same procedure.

| No. | Molecular weight g/mol | Aspect | LCMS purity UV at 254 nm | Mass spectrometry MH+ | M-H+ | ¹H NMR (300 MHz, DMSO) δ |
|---|---|---|---|---|---|---|
| 46 | 346.29 | solid | >99 | 325 | | 8.62 (d, J = 6.7 Hz, 1H), 7.77 (dd, J = 8.9, 5.5 Hz, 2H), 7.64 (d, J = 9.0 Hz, 1H), 7.48-7.38 (m, 1H), 7.31 (t, J = 8.9 Hz, 2H), 7.11 (t, J = 6.8 Hz, 1H), 4.72 (s, 2H), 3.67 (s, 2H). |
| 47 | 342.32 | solid | >99 | 321 | | 8.59 (d, J = 6.7 Hz, 1H), 7.62 (dd, J = 17.6, 8.5 Hz, 3H), 7.51-7.38 (m, 1H), 7.28 (d, J = 8.0 Hz, 2H), 7.12 (t, J = 6.8 Hz, 1H), 4.73 (s, 2H), 3.70 (s, 2H), 2.36 (s, 3H). |
| 48 | 373.30 | orangey solid | >99 | 352 | 350 | 8.75 (d, J = 6.4 Hz, 1H), 8.30 (d, J = 8.8 Hz, 2H), 7.99 (d, J = 8.8 Hz, 2H), 7.69 (d, J = 8.9 Hz, 1H), 7.49 (t, J = 7.6 Hz, 1H), 7.17 (t, J = 6.8 Hz, 1H), 4.79 (s, 2H), 3.69 (d, J = 21.8 Hz, 2H). |
| 49 | 358.32 | solid | >99 | 337 | 335 | 8.56 (s, 1H), 7.63 (d, J = 8.6 Hz, 3H), 7.42 (t, J = 7.1 Hz, 1H), 7.17-6.93 (m, 3H), 4.71 (s, 2H), 3.81 (s, 3H), 3.69 (s, 2H). |
| 50 | 396.30 | solid | 98.7 | 375 | 373 | 8.69 (d, J = 6.7 Hz, 1H), 7.93 (d, J = 8.1 Hz, 2H), 7.81 (d, J = 8.3 Hz, 2H), 7.66 (d, J = 9.0 Hz, 1H), 7.52-7.41 (m, 1H), 7.20-7.09 (m, 1H), 4.76 (s, 2H), 3.70 (s, 2H). |
| 51 | 396.30 | solid | 99 | 375 | 373 | 8.75 (dd, J = 6.7, 1.0 Hz, 1H), 8.13 (s, 1H), 8.01 (d, J = 7.6 Hz, 1H), 7.78 (d, J = 7.9 Hz, 1H), 7.74-7.62 (m, 2H), 7.51-7.41 (m, 1H), 7.14 (td, J = 6.8, 1.1 Hz, 1H), 4.76 (s, 2H), 3.70 (s, 2H). |
| 52 | 329.29 | solid | >99 | 308 | 306 | 8.91 (d, J = 1.4 Hz, 1H), 8.68 (d, J = 6.7 Hz, 1H), 8.60 (dd, J = 4.9, 1.6 Hz, 1H), 8.14 (dt, J = 7.9, 1.8 Hz, 1H), 7.67 (d, J = 9.0 Hz, 1H), 7.55-7.40 (m, 2H), 7.14 (t, J = 6.3 Hz, 1H), 4.76 (s, 2H), 3.70 (s, 2H). |
| 53 | 334.33 | solid | 98.4 | 313 | 311 | 8.55 (d, J = 5.4 Hz, 1H), 8.03 (dd, J = 2.9, 1.0 Hz, 1H), 7.68 (dd, J = 5.0, 3.0 Hz, 2H), 7.38 (dd, J = 5.0, 1.0 Hz, 2H), 7.10 (t, J = 6.8 Hz, 1H), 4.70 (s, 2H), 3.69 (s, 2H). |

Example 4

Preparation of Derivative No. 54: isopropyl 2-((3-((4-fluorophenyl)ethynyl)imidazo[1,2-a]pyridin-2-yl)methoxy)-acetate

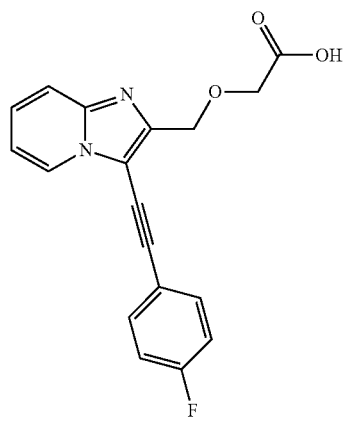

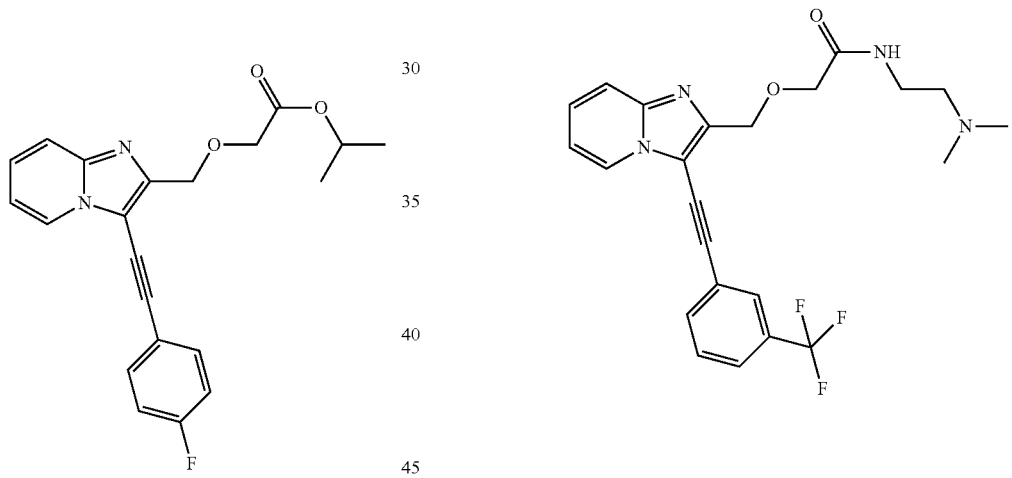

0.155 g (0.478 mmol) of 2-((3-((4-fluorophenyl)ethynyl)imidazo[1,2-a]pyridin-2-yl) methoxy)acetic acid were solubilized with magnetic stirring in 5 ml of isopropanol and a drop of sulfuric acid was added. The mixture was stirred at 60° C. for 3 h. The reaction medium was washed with 2×10 ml of water, and then extracted with 2×30 ml of ethyl acetate. The combined organic phases were washed with 30 ml of a saturated NaCl aqueous solution, dried on $Na_2SO_4$ which was then removed by filtration. The obtained filtrate was concentrated in vacuo. 0.162 mg (yield=91%) of isopropyl 2-((3-((4-fluorophenyl)ethynyl)imidazo[1,2-a]pyridin-2-yl)-methoxy)acetate were obtained as a brown oil. LC-MS: m/z=367 (MH⁺); UV purity at 254 nm=98%. ¹H NMR (300 MHz, DMSO) δ 8.62 (d, J=6.8 Hz, 1H), 7.74 (dd, J=8.7, 5.5 Hz, 2H), 7.67 (d, J=9.0 Hz, 1H), 7.45 (d, J=7.0 Hz, 1H), 7.33 (t, J=8.9 Hz, 2H), 7.12 (t, J=6.5 Hz, 1H), 4.93 (dt, J=12.5, 6.3 Hz, 1H), 4.78 (s, 2H), 4.19 (s, 2H), 1.15 (d, J=6.3 Hz, 6H).

Example 5

Preparation of derivative No 55: N-(2-(dimethylamino)ethyl)-2-((3-((3-(trifluoromethyl)phenyl)ethynyl)imidazo[1,2-a]pyridin-2-yl)methoxy)acetamide

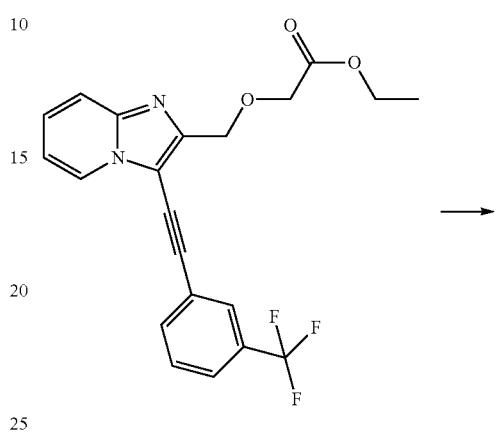

0.15 g (0.373 mmol) of ethyl 2-((3-((3-(trifluoromethyl)phenyl)ethynyl)imidazo[1,2-a]pyridin-2-yl)methoxy)acetate were solubilized in 2 ml of pyridine with magnetic stirring, to this solution were added 0.409 ml (3.73 mmol) of N,N-dimethylethane-1,2-diamine and 0.249 mg (1.864 mmol) of aluminium trichloride. The mixture was stirred at r.t. for 18 h before being treated with 30 ml of a saturated NaCl aqueous solution. The aqueous phase was extracted with 3×30 ml of ethyl acetate. The combined organic phases were dried on $Na_2SO_4$ which was then removed by filtration. The obtained filtrate was concentrated in vacuo. 0.056 g (yield=34%) of N-(2-(dimethylamino)ethyl)-2-((3-((3-(trifluoromethyl)phenyl)ethynyl)-imidazo[1,2-a]pyridin-2-yl)methoxy) acetamide were obtained as a beige solid. LC-MS: m/z=445 (MH⁺); UV purity at 254 nm=96%. ¹H NMR (300 MHz, CDCl₃) δ 7.85 (s, 1H), 7.78 (d, J=7.7 Hz, 2H), 7.70 (s, 2H), 7.58 (t, J=7.8 Hz, 2H), 7.23 (s, 1H), 5.11 (s, 2H), 4.31 (dd, J=26.6, 11.2 Hz, 2H), 3.83 (s, 2H), 3.33 (s, 2H), 2.89 (s, 6H).

Example 6

Preparation of Derivative No. 56: 2-((3-((4-fluorophenyl)ethynyl)imidazo[1,2-a]pyridin-2-yl)methoxy)-1-morpholino-ethanone

Step 1: Preparation of 2-((3-((4-fluorophenyl)ethynyl)-imidazo[1,2-a]pyridin-2-yl)methoxy) acetyl chloride

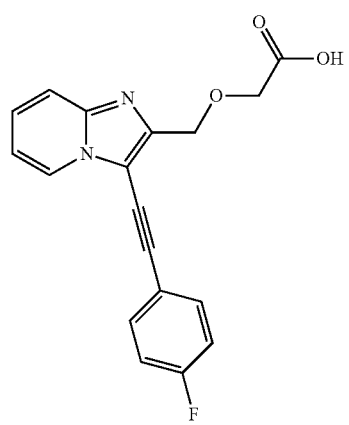

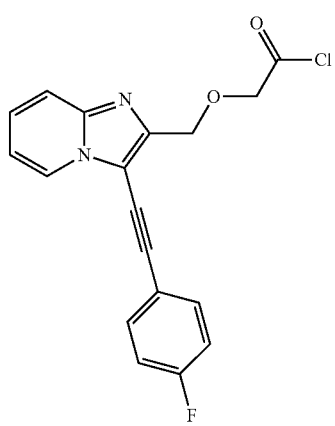

1.5 g (4.63 mmol) of 2-((3-((4-fluorophenyl)ethynyl)imidazo[1,2-a]pyridin-2-yl)methoxy)acetic acid were suspended in 40 ml of dichloromethane with magnetic stirring, the mixture was placed in a bath at 0° C. and then 1.215 ml (13.88 mmol) of oxalyl chloride were added dropwise, finally, a few drops of dimethylformamide were added. The cold bath was withdrawn and then the mixture was stirred at r.t. for 1 h. The reaction medium was concentrated in vacuo and immediately used in the next step.

Step 2: Preparation of 2-((3-((4-fluorophenyl)ethynyl)imidazo[1,2-a]pyridin-2-yl)methoxy)-1-morpholinoethanone (Derivative No. 56)

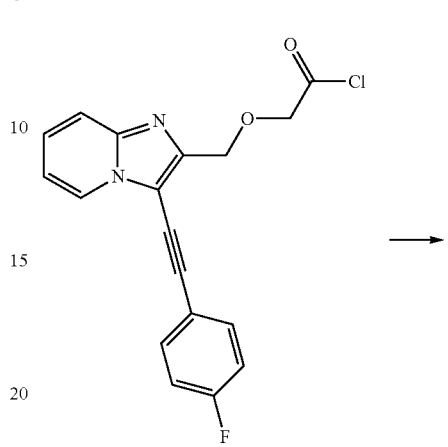

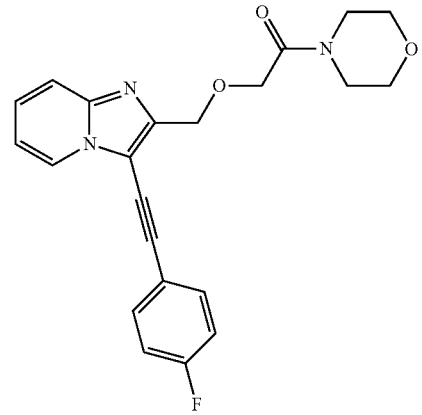

0.806 ml (9.25 mmol) of morpholine were solubilised in 4 ml of dichloromethane with magnetic stirring, a solution of 2-((3-((4-fluorophenyl)ethynyl)imidazo[1,2-a]pyridin-2-yl)methoxy)acetyl chloride in 4 ml of dichloromethane was added and then the mixture was added at r.t. for 1 h before being treated with 10 ml of water. The aqueous phase was extracted with 2×5 ml of dichloromethane. The combined organic phases were washed with 5 ml of a saturated NaCl aqueous solution, dried on $Na_2SO_4$ which was then removed by filtration. The obtained filtrate was concentrated in vacuo. The crude residue was purified by flash chromatography on a silica gel cartridge (eluent: ethyl acetate 100%). 0.211 g (yield=58%) of 2-((3-((4-fluorophenyl)ethynyl)imidazo[1,2-a]pyridin-2-yl)methoxy)-1-morpholino ethanone were obtained as a pale yellow solid. LC-MS: m/z=394 (MH$^+$); UV purity at 254 nm=99%. $^1$H NMR (300 MHz, DMSO) δ 8.62 (d, J=6.8 Hz, 1H), 7.74 (dd, J=8.7, 5.5 Hz, 2H), 7.67 (d, J=9.0 Hz, 1H), 7.50-7.39 (m, 1H), 7.33 (t, J=8.9 Hz, 2H), 7.12 (t, J=6.8 Hz, 1H), 4.75 (s, 2H), 4.27 (s, 2H), 3.55-3.46 (m, 4H), 3.39 (s, 4H).

Derivatives numbers 57 to 59 were obtained from of 2-((3-((4-fluorophenyl)ethynyl)imidazo[1,2-a]pyridin-2-yl)methoxy)acetyl chloride according to the same procedure.

| No. | Molecular weight g/mol | Aspect | LCMS purity UV at 254 nm | Mass spectrometry MH+ | M-H+ | ¹H NMR (300 MHz, DMSO) δ |
|---|---|---|---|---|---|---|
| 57 | 394.44 | Solid | 99 | 395 | | 8.64 (d, J = 6.8 Hz, 1H), 7.82-7.59 (m, 4H), 7.51-7.41 (m, 1H), 7.34 (t, J = 8.9 Hz, 2H), 7.19-7.05 (m, 1H), 4.79 (s, 2H), 4.03 (s, 2H), 3.17 (dd, J = 12.6, 6.5 Hz, 2H), 2.24 (t, J = 6.7 Hz, 2H), 2.09 (s, 6H). |
| 58 | 367.37 | Solid | 99 | 368 | | 11.10 (s, 1H), 8.63 (d, J = 6.7 Hz, 1H), 7.76 (dd, J = 8.6, 5.5 Hz, 2H), 7.68 (d, J = 9.0 Hz, 1H), 7.49-7.41 (m, 1H), 7.33 (t, J = 8.8 Hz, 2H), 7.13 (t, J = 6.7 Hz, 1H), 4.77 (s, 2H), 4.02 (s, 2H), 3.78 (q, J = 7.0 Hz, 2H), 1.10 (t, J = 7.0 Hz, 3H). |
| 59 | 339.32 | Solid | 97.4 | 340 | | 10.60 (s, 1H), 8.84 (s, 1H), 8.63 (d, J = 6.6 Hz, 1H), 7.87-7.60 (m, 3H), 7.36 (dd, J = 31.0, 22.2 Hz, 3H), 7.13 (t, J = 6.7 Hz, 1H), 4.76 (s, 2H), 4.01 (s, 2H). |

Example 7

Preparation of Derivative number 60: 2-((3-((4-fluorophenyl)ethynyl)imidazo[1,2-a]pyridin-2-yl)methoxy)-1-morpholinoethanone

Step 1: Preparation of 2-(((triisopropylsilyl)oxy)methyl)imidazo[1,2-a]pyridine

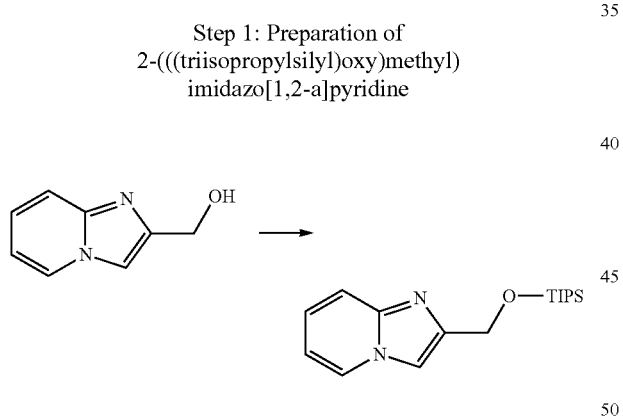

1 g (6.55 mmol) of imidazo[1,2-a]pyridin-2-ylmethanol were solubilised in 25 ml of dichloromethane with magnetic stirring and then 2.145 ml (9.82 mmol) of triisopropylsilyl chloride were slowly added. The mixture was stirred at r.t. for 1 h before being treated with 100 ml of water. The aqueous phase was extracted with 3×50 ml of dichloromethane. The combined organic phases were washed with 100 ml of a saturated NaCl aqueous solution, dried on Na₂SO₄ which was then removed by filtration. The obtained filtrate was concentrated in vacuo. The crude residue was purified by flash chromatography on a silica gel cartridge (eluent: dichloromethane 100% and then ethyl acetate 100%). 1.85 g (yield=92%) of 2-(((triisopropylsilyl)oxy)methyl)imidazo[1,2-a]pyridine were obtained as a colourless oil. LC-MS: m/z=305 (MH⁺); UV purity at 254 nm=99%. ¹H NMR (300 MHz, DMSO) δ 8.57-8.50 (m, 1H), 7.81 (s, 1H), 7.46 (dd, J=9.1, 0.6 Hz, 1H), 7.19 (ddd, J=9.1, 6.7, 1.3 Hz, 1H), 6.84 (td, J=6.8, 1.1 Hz, 1H), 4.88 (d, J=0.6 Hz, 2H), 1.23-1.11 (m, 3H), 1.11-1.02 (m, 18H).

Step 2: Preparation of 3-iodo-2-(((triisopropylsilyl)oxy)methyl)imidazo[1,2-a]pyridine 1.85 g (6.08 mmol) of 2-(((triisopropylsilyl)oxy)methyl)imidazo[1,2-a]pyridine were solubilised in 25 ml of acetonitrile with magnetic stirring, to this solution were added 1.409 g (6.08 mmol) of N-iodosuccinimide. The mixture was stirred at r.t. for 16 h before being treated with 100 ml of water. The aqueous phase was extracted with 3×50 ml of dichloromethane. The combined organic phases were washed with 100 ml of a saturated NaCl aqueous solution, dried on Na₂SO₄ which was then removed by filtration. The obtained filtrate was concentrated in vacuo. 2.29 g (yield=83%) of 3-iodo-2-(((triisopropylsilyl)oxy)methyl)imidazo[1,2-a]pyridine were obtained as a pale yellow solid. LC-MS: m/z=431 (MH⁺); UV purity at 254 nm=95%.

$^1$H NMR (300 MHz, DMSO) δ 8.30 (dd, J=5.6, 2.2 Hz, 1H), 7.59 (dd, J=14.3, 9.1 Hz, 1H), 7.33 (tt, J=6.8, 4.1 Hz, 1H), 7.14-6.96 (m, 1H), 4.80 (s, 2H), 1.27-0.90 (m, 21H).

Step 3: Preparation of 3-(phenylethynyl)-2-(((triisopropylsilyl)oxy)methyl)imidazo[1,2-a]pyridine

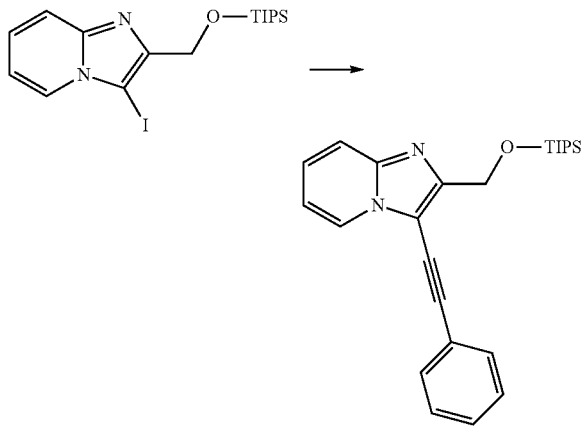

In a flask placed under an argon flow, 2.29 g (5.32 mmol) of 3-iodo-2-(((triisopropylsilyl)oxy)methyl)imidazo[1,2-a]pyridine were solubilised in 11 ml of dimethylformamide with magnetic stirring. To this solution, were added: 0.103 g (0.532 mmol) of copper iodide, 0.715 ml (6.38 mmol) of phenylacetylene and 11.12 ml (80 mmol) of triethylamine. The reaction medium was degassed with argon for 10 min before adding 0.487 g (0.532 mmol) of Pd$_2$(dba)$_3$. The mixture was stirred at r.t. for 16 h before being filtered on celite. The celite was washed with 200 ml of ethyl acetate. The filtrate was washed with 2×100 ml of water and 100 ml of a saturated NaCl aqueous solution and then dried on Na$_2$SO$_4$ which was then removed by filtration. The obtained filtrate was concentrated in vacuo. The crude residue was purified by flash chromatography on a silica gel cartridge (eluent: heptane/ethyl acetate gradient, from 90% to 80% of heptane, v/v). 1.56 g (yield=72%) of 2 3-(phenylethynyl)-2-(((triisopropylsilyl)oxy)methyl)imidazo[1,2-a]pyridine were obtained as a brown solid. LC-MS: m/z=405 (MH$^+$); UV purity at 254 nm=99%. $^1$H NMR (300 MHz, DMSO) δ 8.60 (d, J=6.7 Hz, 1H), 7.72-7.55 (m, 3H), 7.52-7.36 (m, 4H), 7.17-7.06 (m, 1H), 4.94 (s, 2H), 1.14 (m, 3H), 1.04 (d, J=6.5 Hz, 18H).

Step 4: Preparation of (3-(phenylethynyl)imidazo[1,2-a]pyridin-2-yl)methanol (Derivative Number 60)

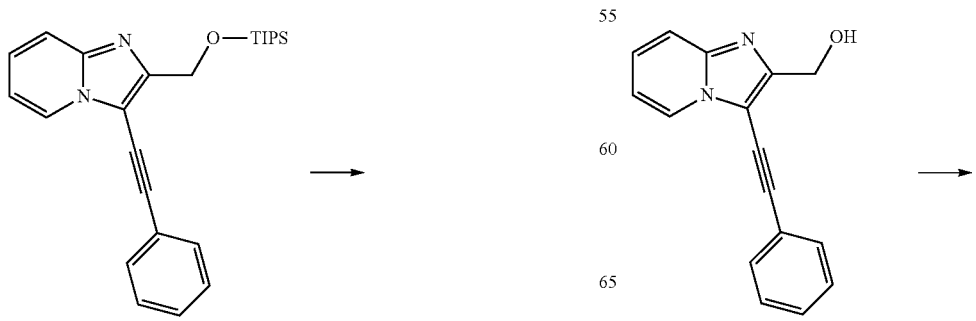

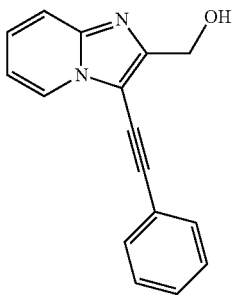

1.56 g (3.86 mmol) of 2-(((triisopropylsilyl)oxy)methyl)imidazo[1,2-a]pyridine were solubilized in 30 ml of tetrahydrofurane with magnetic stirring, to this solution were added 4.24 ml (4.24 mmol) of a 1M solution of tetrabutylammonium fluoride in tetrahydrofurane. The mixture was stirred at r.t. for 1 hour before being concentrated in vacuo. The crude residue was directly purified by flash chromatography on a silica gel cartridge (eluent: ethyl acetate 100%). 0.83 g (yield=86%) of (3-(phenylethynyl)imidazo[1,2-a]pyridin-2-yl)methanol were obtained as an orangey solid. LC-MS: m/z=249 (MH$^+$); UV purity at 254 nm=99%. $^1$H NMR (300 MHz, DMSO) δ 8.59 (dt, J=6.7, 1.1 Hz, 1H), 7.77-7.56 (m, 3H), 7.56-7.32 (m, 4H), 7.11 (td, J=6.8, 1.1 Hz, 1H), 5.33 (t, J=5.9 Hz, 1H), 4.67 (d, J=5.9 Hz, 2H).

Derivative number 100 was obtained according to the same procedure.

| No. | Molecular weight g/mol | Aspect | LCMS purity UV at 254 | Mass spectrometry m/z MH+ | $^1$H NMR (300 MHz, DMSO) δ |
|---|---|---|---|---|---|
| 100 | 316.28 | pale brown solid | 94 | 317.1 | 8.74 (d, J = 6.7 Hz, 1H), 8.10 (s, 1H), 7.96 (d, J = 7.6 Hz, 1H), 7.83-7.63 (m, 3H), 7.50-7.39 (m, 1H), 7.13 (t, J = 6.5 Hz, 1H), 5.36 (t, J = 5.9 Hz, 1H), 4.70 (d, J = 5.9 Hz, 2H) |

Example 8

Preparation of Derivative No. 61: isobutyl ((3-(phenyl ethynyl)imidazo[1,2-a]pyridin-2-yl)methyl) carbonate

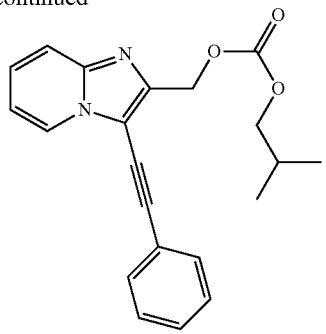

0.1 g (0.403 mmol) of (3-(phenylethynyl)imidazo[1,2-a]pyridin-2-yl) methanol were solubilised in 3 ml of dichloromethane with magnetic stirring. 0.084 ml (0.604 mmol) of triethylamine and 0.059 ml (0.443 mmol) of isobutyl chloroformate were added. The mixture was stirred at r.t. for 15 min before being concentrated in vacuo. The residue was taken up in 10 ml of diisopropyl ether and a solid was isolated by filtration. The solid was purified by preparative HPLC and 0.084 g (yield=59%) of isobutyl ((3-(phenylethynyl)imidazo[1,2-a]pyridin-2-yl)methyl) carbonate were obtained as a pale yellow solid. LC-MS: m/z=349 (MH+); UV purity at 254 nm=99%. ¹H NMR (300 MHz, DMSO) δ 8.70 (d, J=6.8 Hz, 1H), 7.79-7.65 (m, 3H), 7.60-7.45 (m, 4H), 7.23 (td, J=6.8, 1.1 Hz, 1H), 5.42 (s, 2H), 3.91 (d, J=6.6 Hz, 2H), 1.95-1.80 (m, 1H), 0.86 (d, J=6.7 Hz, 6H).

Example 9

Preparation of Derivative No. 62: (3-(phenylethynyl)imidazo[1,2-a]pyridin-2-yl)methyl morpholine-4-carboxylate

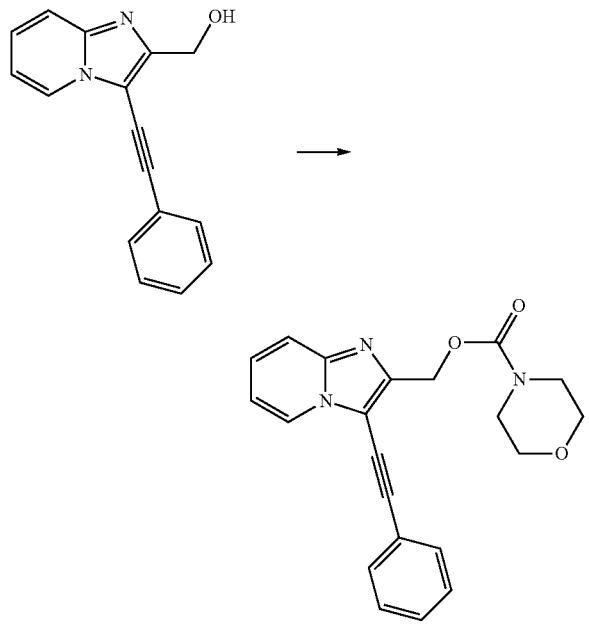

0.117 g (0.467 mmol) of (3-(phenylethynyl)imidazo[1,2-a]pyridin-2-yl) methanol were solubilised in 4 ml of tetrahydrofurane with magnetic stirring. 0.228 g (0.7 mmol) of cesium carbonate and 0.61 ml (0.513 mmol) of morpholine-4-carbonyl chloride were added. The mixture was stirred at r.t. for 16 h. 1.22 ml (1.026 mmol) of additional morpholine-4-carbonyl chloride were added and the mixture was stirred at r.t. for 2 d before being treated with 10 ml of a saturated NaCl aqueous solution. The aqueous phase was extracted with 3×10 ml of ethyl acetate. The combined organic phases were dried on Na₂SO₄ which was then removed by filtration. The crude residue was purified by preparative HPLC and 0.078 g (yield=46%) of (3-(phenylethynyl)imidazo[1,2-a]pyridin-2-yl)methylmorpholine-4-carboxylate were obtained as a beige solid. LC-MS: m/z=362 (MH+); UV purity at 254 nm=99%. ¹H NMR (300 MHz, DMSO) δ 8.60 (d, J=6.7 Hz, 1H), 7.66 (dd, J=11.0, 5.4 Hz, 3H), 7.47 (dd, J=4.1, 1.3 Hz, 4H), 7.14 (t, J=6.4 Hz, 1H), 5.33 (s, 2H), 3.48 (s, 4H), 3.34 (s, 4H).

Example 10

Preparation of Derivative No. 63: (3-(phenyl ethynyl)imidazo[1,2-a]pyridin-2-yl)methyl diethylcarbamate

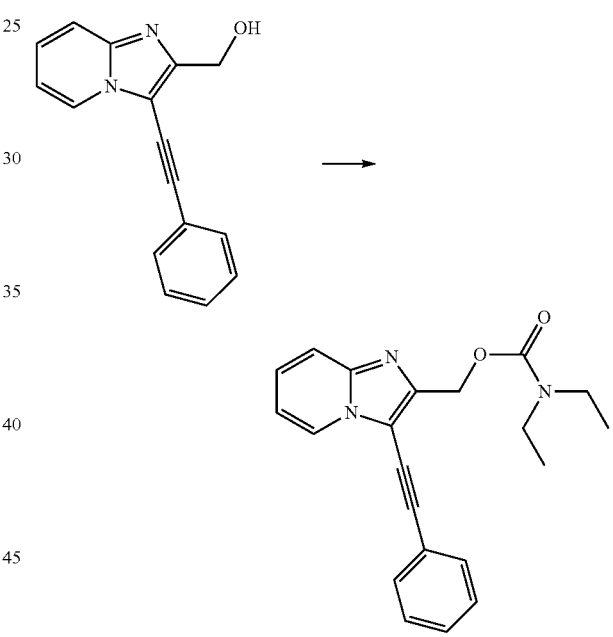

0.1 g (0.403 mmol) of (3-(phenylethynyl)imidazo[1,2-a]pyridin-2-yl) methanol were solubilised in 3 ml of dimethylformamide with magnetic stirring. The mixture was cooled to 0° C., 0.048 g (1.208 mmol) of sodium hydride (60% by mass) were added portion wise. The mixture was stirred for 10 min at 0° C. and then 0.204 ml (1.611 mmol) of diethylcarbamoyl chloride were added. The cold bath was withdrawn, the mixture was stirred at r.t. for 2 h before being treated with 30 ml of a saturated NaCl aqueous solution. The aqueous phase was extracted with 3×10 ml of ethyl acetate. The combined organic phases were dried on Na₂SO₄ which was then removed by filtration. The crude residue was purified by flash chromatography on a silica gel cartridge (eluent: heptane/ethyl acetate, 6/4, v/v). 0.101 g (yield=72%) of (3-(phenylethynyl)imidazo[1,2-a]pyridin-2-yl)methyl diethylcarbamate were obtained as a pale yellow solid. LC-MS: m/z=348 (MH+); UV purity at 254 nm=99%. ¹H NMR (300 MHz, DMSO) δ 8.61 (d, J=6.8 Hz, 1H), 7.74-7.59 (m, 3H), 7.53-7.38 (m, 4H), 7.13 (td, J=6.8, 1.1 Hz, 1H), 5.30 (s, 2H), 3.22 (q, J=7.1 Hz, 4H), 1.01 (t, J=7.1 Hz, 6H).

Example 11

Preparation of Derivative No. 64: 3-((2-((2-hydroxy ethoxy)methyl)imidazo[1,2-a]pyridin-3-yl)ethynyl) benzonitrile Step 1: Preparation of 2-(chloromethyl)-3-iodoimidazo[1,2-a]pyridine

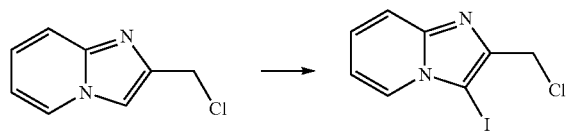 [SMILES: ClCc1cn2ccccc2n1 ; ClCc1nc2ccccn2c1I]

5 g (30 mmol) of 2-(chloromethyl)imidazo[1,2-a]pyridine were solubilised in 60 ml of acetonitrile with magnetic stirring, 7.31 g (31.5 mmol) of N-iodosuccinimide were added and the mixture was stirred at r.t. for 15 min. The solid formed was isolated by filtration, washed with 30 ml of water and dried in a vacuum bell jar. 8.46 g (yield=95%) of 2-(chloromethyl)-3-iodoimidazo[1,2-a]pyridine were obtained as a white solid. LC-MS: m/z=293 (MH+); UV purity at 254 nm=99%. $^1$H NMR (300 MHz, DMSO) δ 8.31 (d, J=6.9 Hz, 1H), 7.58 (d, J=9.1 Hz, 1H), 7.46-7.29 (m, 1H), 7.07 (td, J=6.8, 1.0 Hz, 1H), 4.81 (s, 2H).

Step 2: Preparation of (3-iodoimidazo[1,2-a]pyridin-2-yl)methyl 3-hydroxypropanoate

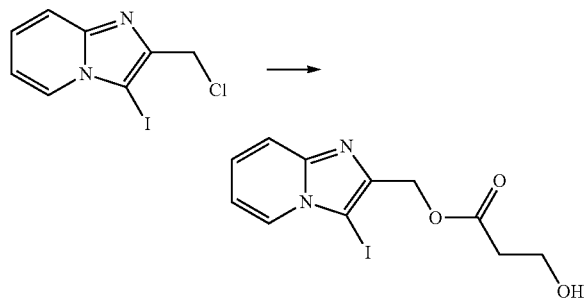

In a flask placed under an argon flow, 0.515 ml (3.42 mmol) of 2-(chloromethyl)-3-iodoimidazo[1,2-a]pyridine were solubilised with magnetic stirring in 8 ml of tetrahydrofurane and then 0.06 g (1.504 mmol) of sodium hydride (60% by mass) were added, the mixture was stirred at r.t. for 30 min and then 0.4 g (1.368 mmol) of 2-(chloromethyl)-3-iodoimidazo[1,2-a]pyridine and 0.05 ml (0.137 mmol) of tetrabutyl ammonium iodide were added. The mixture was stirred with reflux for 2 d. The reaction medium was treated with 30 ml of a saturated ammonium chloride aqueous solution. The aqueous phase was extracted with 2×30 ml of ethyl acetate. The combined organic phases were washed with 30 ml of a saturated NaCl aqueous solution, dried on Na$_2$SO$_4$ which was then removed by filtration. The obtained filtrate was concentrated in vacuo. The crude residue was purified by flash chromatography on a silica gel cartridge (eluent: heptane/ethyl acetate gradient, 1/1, v/v). 0.17 g (yield=36%) of (3-iodoimidazo[1,2-a]pyridin-2-yl)methyl 3-hydroxypropanoate were obtained as a brown solid. LC-MS: m/z=347 (MH+); UV purity at 254 nm=99%.

$^1$H NMR (300 MHz, DMSO) δ 8.32 (d, J=6.9 Hz, 1H), 7.57 (d, J=9.1 Hz, 1H), 7.42-7.24 (m, 1H), 7.07 (t, J=6.4 Hz, 1H), 5.16 (s, 2H), 4.73 (t, J=5.3 Hz, 1H), 3.64 (dd, J=11.6, 6.0 Hz, 2H), 2.46 (m, 2H).

Step 3: Preparation of (3-((3-cyanophenyl)ethynyl) imidazo[1,2-a]pyridin-2-yl)methyl 3-hydroxypropanoate (Derivative No. 64)

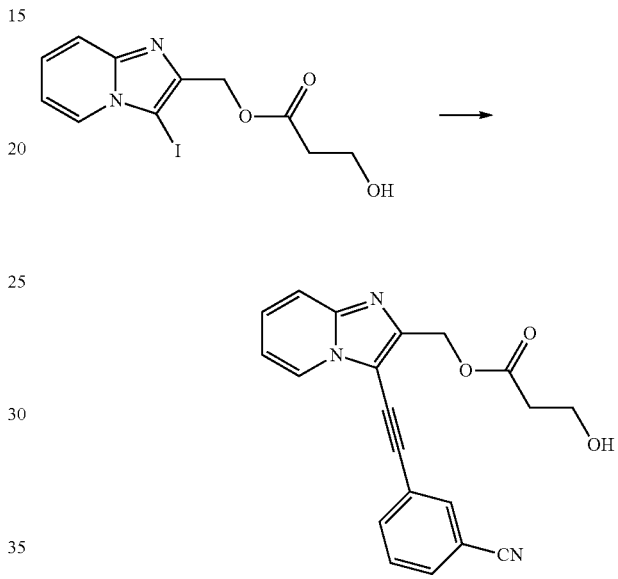

In a flask placed under an argon flow, 0.138 g (0.397 mmol) of (3-iodoimidazo[1,2-a]pyridin-2-yl)methyl 3-hydroxypropanoate were solubilised in 4 ml of dimethylformamide with magnetic stirring. To this solution, were added: 0.008 g (0.04 mmol) of copper iodide, 0.06 g (0.477 mmol) of 3-ethynylbenzonitrile and 0.831 ml (5.96 mmol) of triethylamine. The reaction medium was degassed with argon for 10 min before adding 0.036 g (0.04 mmol) of Pd$_2$(dba)$_3$. The mixture was stirred at r.t. for 1 h before being treated with 50 ml of a saturated NaCl aqueous solution, the aqueous phase was extracted with 2×50 ml of ethyl acetate. The combined organic phases were washed with 50 ml of a saturated NaCl aqueous solution and then dried on Na$_2$SO$_4$ which was then removed by filtration. The obtained filtrate was concentrated in vacuo. The crude residue was purified by flash chromatography on a silica gel cartridge (eluent: heptane/ethyl acetate, 2/8, v/v). 0.12 g (yield=82%) of (3-((3-cyanophenyl)ethynyl) imidazo[1,2-a]pyridin-2-yl)methyl 3-hydroxy propanoate were obtained as a yellow solid. LC-MS: m/z=346 (MH+); UV purity at 254 nm=93%. $^1$H NMR (300 MHz, DMSO) δ 8.74 (d, J=6.8 Hz, 1H), 8.26 (s, 1H), 7.98 (dd, J=5.3, 3.9 Hz, 1H), 7.90 (dd, J=5.2, 3.8 Hz, 1H), 7.76-7.63 (m, 2H), 7.57-7.41 (m, 1H), 7.18 (td, J=6.8, 1.0 Hz, 1H), 5.35 (s, 2H), 4.76 (t, J=5.3 Hz, 1H), 3.67 (dd, J=11.6, 6.2 Hz, 2H), 2.54-2.49 (m, 2H).

Derivatives numbers 65 to 67 were prepared according to the same sequence of steps 1 to 4.

| No. | Molecular weight g/mol | Aspect | LCMS purity UV at 254 nm | Mass spectrometry MH+ | M-H+ | 1H NMR (300 MHz, DMSO) δ |
|---|---|---|---|---|---|---|
| 65 | 317.34 | Solid | 99 | 318 | | 8.72 (d, J = 6.7 Hz, 1H), 8.25 (s, 1H), 7.98 (d, J = 7.9 Hz, 1H), 7.88 (d, J = 7.8 Hz, 1H), 7.67 (t, J = 8.0 Hz, 2H), 7.54-7.38 (m, 1H), 7.14 (t, J = 6.7 Hz, 1H), 4.72 (s, 2H), 4.66 (t, J = 5.2 Hz, 1H), 3.56 (dd, J = 8.3, 4.6 Hz, 4H). |
| 66 | 388.34 | Solid | 99 | 389 | | 8.76 (d, J = 6.7 Hz, 1H), 8.12 (s, 1H), 7.97 (d, J = 7.6 Hz, 1H), 7.80 (d, J = 7.9 Hz, 1H), 7.71 (dd, J = 8.3, 5.8 Hz, 2H), 7.55-7.43 (m, 1H), 7.17 (t, J = 6.7 Hz, 1H), 5.36 (s, 2H), 4.74 (t, J = 5.3 Hz, 1H), 3.66 (dd, J = 11.7, 6.0 Hz, 2H), 2.52 (d, J = 6.4 Hz, 2H). |
| 67 | 360.33 | Solid | 96 | 363 | 361 | 8.77 (d, J = 6.7 Hz, 1H), 8.13 (s, 1H), 7.99 (d, J = 7.6 Hz, 1H), 7.81 (d, J = 7.8 Hz, 1H), 7.72 (t, J = 8.8 Hz, 2H), 7.56-7.42 (m, 1H), 7.16 (td, J = 6.8, 1.0 Hz, 1H), 4.75 (s, 2H), 4, 70 (s, 1H), 3.58 (td, J = 7.7, 4.0 Hz, 4H). |

Example 12

Preparation of Derivative No. 68: 2-(((3-((3-(trifluoromethyl)phenyl)ethynyl)imidazo[1,2-a]pyridin-2-yl)methyl)amino)acetic acid Step 1: Preparation of 2-(imidazo[1,2-a]pyridin-2-ylmethyl)isoindoline-1,3-dione

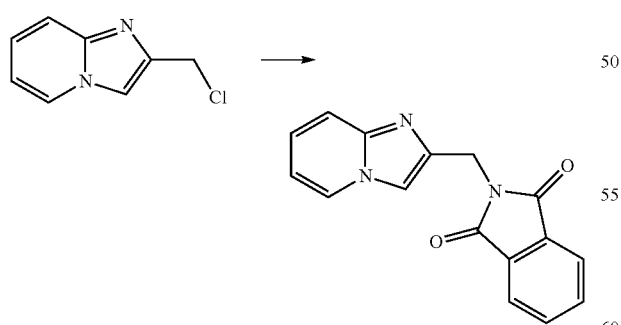

1.5 g (9 mmol) of 2-(chloromethyl)imidazo[1,2-a]pyridine were solubilised in 55 ml of dimethylformamide with magnetic stirring, 1.834 g (9.9 mmol) of potassium phthalimide were added portion wise and then the mixture was stirred at 60° C. for 2 h. The obtained solid was isolated by filtration, washed with 30 ml of diisopropyl ether and dried in a vacuum bell jar in order to obtain 1.81 g (yield=67%) of 2-(imidazo[1,2-a]pyridin-2-ylmethyl)isoindoline-1,3-dione as a white solid. LC-MS: m/z=278 (MH+); UV purity at 254 nm=93%. 1H NMR (300 MHz, DMSO) δ 8.45 (d, J=6.8 Hz, 1H), 7.96-7.67 (m, 5H), 7.45 (dd, J=9.1, 0.5 Hz, 1H), 7.33-7.14 (m, 1H), 6.84 (td, J=6.8, 1.1 Hz, 1H), 4.88 (s, 2H).

Step 2: Preparation of 2-((3-iodoimidazo[1,2-a]pyridin-2-yl)methyl)isoindoline-1,3-diose

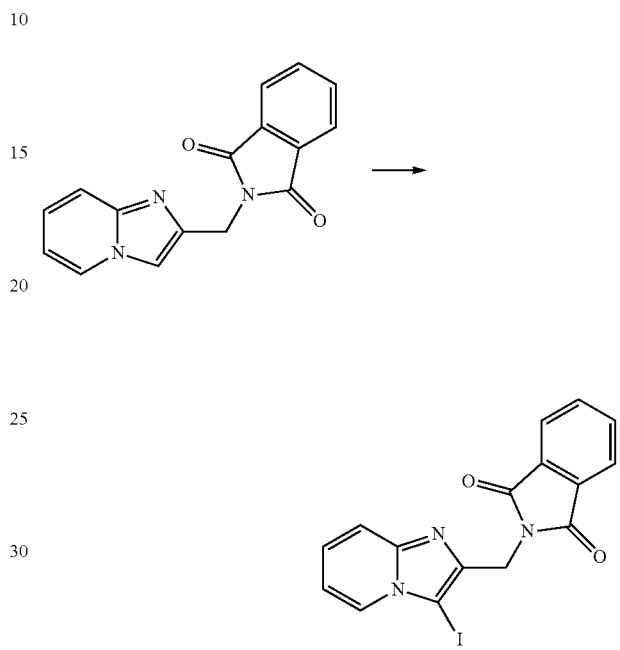

1.7 g (5.7 mmol) of 2-(chloromethyl)imidazo[1,2-a]pyridine were solubilised in 65 ml of acetonitrile with magnetic stirring, 1.389 g (5.99 mmol) of N-iodosuccinimide were added and the mixture was stirred at r.t. for 1 h. The solid formed was isolated by filtration, washed with 20 ml of diisopropyl ether and dried in a vacuum bell jar. 0.105 g (yield=87%) of 2-((3-iodoimidazo[1,2-a]pyridin-2-yl)methyl) isoindoline-1,3-dione were obtained as a white solid. LC-MS: m/z=404 (MH+); UV purity at 254 nm=78%. 1H NMR (300 MHz, DMSO) δ 8.29 (d, J=6.8 Hz, 1H), 7.89 (d, J=5.6 Hz, 4H), 7.48 (d, J=9.0 Hz, 1H), 7.36-7.24 (m, 1H), 7.03 (t, J=6.4 Hz, 1H), 4.89 (s, 2H).

Step 3: Preparation of 2-((3-((3-(trifluoromethyl) phenyl) ethynyl)imidazo[1,2-a]pyridin-2-yl)methyl) isoindoline-1,3-dione

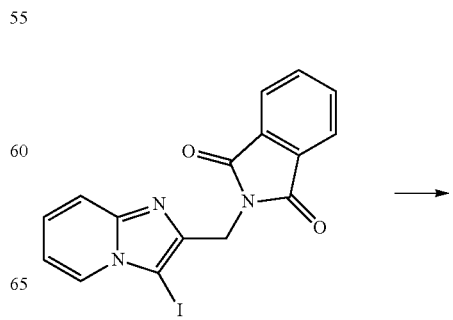

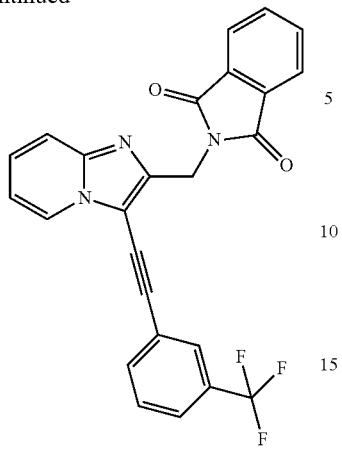

In a flask placed under an argon flow, 2.1 g (5.21 mmol) of 2-((3-iodoimidazo[1,2-a]pyridin-2-yl)methyl)isoindoline-1,3-dione were solubilised in 11 ml of dimethylformamide with magnetic stirring. To this solution, were added: 0.008 g (0.04 mmol) of copper iodide, 0.921 ml (6.25 mmol) of 3-trifluoromethylphenyl acetylene and 10.89 ml (78 mmol) of triethylamine. The reaction medium was degassed with argon for 10 min before adding 0.477 g (0.521 mmol) of Pd$_2$(dba)$_3$. The mixture was stirred at r.t. for 16 h before being filtered on a silica gel cartridge which was then rinsed with 300 ml of ethyl acetate. The organic phase was washed with 3×150 ml of a saturated NaCl aqueous solution, and then dried on Na$_2$SO$_4$ which was then removed by filtration. The obtained filtrate was concentrated in vacuo. The crude residue was purified by flash chromatography on a silica gel cartridge (eluent: heptane/ethyl acetate gradient, from 50% to 40% of heptane, v/v). 1.41 g (yield=59%) of 2-((3-((3-(trifluoromethyl)phenyl)ethynyl)imidazo[1,2-a]pyridin-2-yl)methyl) isoindoline-1,3-dione were obtained as a brown solid. LC-MS: m/z=446 (MH$^+$); UV purity at 254 nm=97%. $^1$H NMR (300 MHz, DMSO) δ 8.67 (d, J=6.7 Hz, 1H), 7.91 (dd, J=5.6, 3.0 Hz, 2H), 7.82 (dd, J=5.5, 3.1 Hz, 2H), 7.69 (dd, J=12.5, 8.5 Hz, 2H), 7.63-7.52 (m, 2H), 7.52-7.42 (m, 2H), 7.13 (td, J=6.8, 1.1 Hz, 1H), 5.09 (s, 2H).

Step 4: Preparation of (3-((3-(trifluoromethyl)phenyl) ethynyl)imidazo[1,2-a]pyridin-2-yl)methenamine

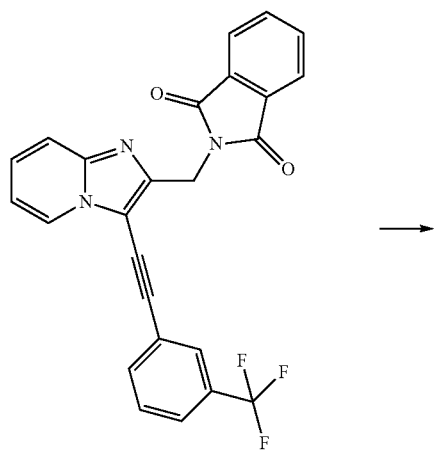

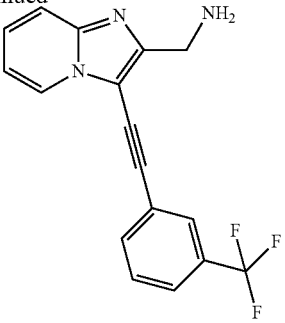

1.41 g (3.08 mmol) of 2-((3-((3-(trifluoromethyl)phenyl) ethynyl) imidazo[1,2-a]pyridin-2-yl)methyl) isoindoline-1,3-dione were solubilised in 30 ml of ethanol with magnetic stirring, 0.978 ml (30.8 mmol) of hydrazine monohydrate were added. The mixture gradually became milky and was stirred at r.t. for 1.5 h. The suspended solid was isolated by filtration and washed with 2×25 ml of ethanol. The filtrate was concentrated in vacuo. The residue was triturated in 20 ml of ethanol, the solid was isolated by filtration and the filtrate concentrated in vacuo in order to obtain 0.715 g (yield=69%) of (3-((3-(trifluoromethyl)phenyl)ethynyl)imidazo[1,2-a]pyridin-2-yl)methanamine as a pale yellow solid. LC-MS: m/z=316 (MH$^+$); UV purity at 254 nm=94%. $^1$H NMR (300 MHz, DMSO) δ 8.73 (d, J=6.7 Hz, 1H), 8.12 (s, 1H), 7.98 (d, J=7.7 Hz, 1H), 7.82-7.63 (m, 3H), 7.49-7.40 (m, 1H), 7.13 (td, J=6.8, 1.1 Hz, 1H), 3.96 (s, 2H).

Step 5: Preparation of 2-(((3-((3-(trifluoromethyl) phenyl)ethynyl)imidazo[1,2-a]pyridin-2-yl)methyl) amino) acetic acid (Derivative Number 68)

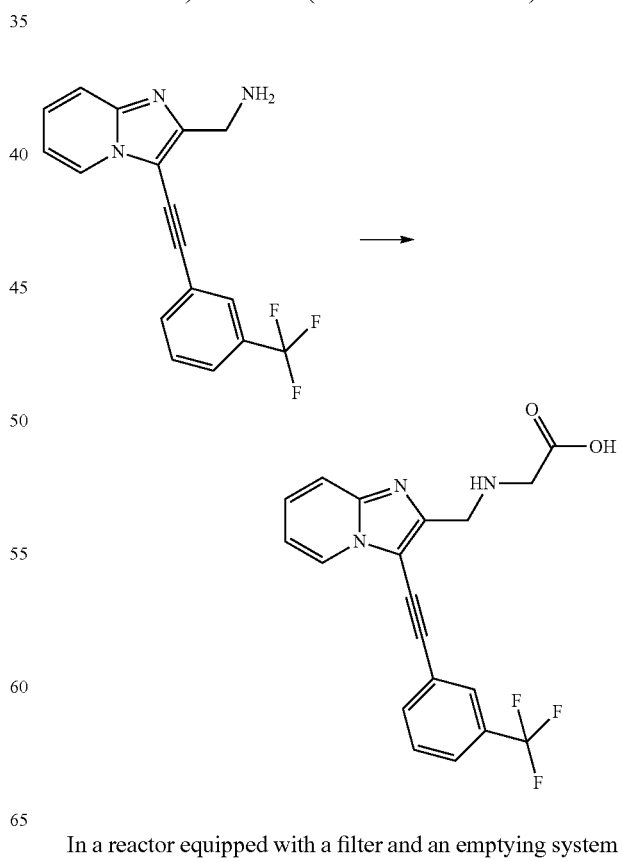

In a reactor equipped with a filter and an emptying system and placed on a vortex, were introduced 0.33 g (0.656 mmol)

of cyanoborohydride resin. The resin was swelled in 3 ml of dichloromethane, the mixture was stirred at r.t. for 10 min and then dichloromethane was removed by filtration. The operation was repeated a second time and then a mixture of 0.2 g of (3-((3-(trifluoromethyl)phenyl)ethynyl) imidazo[1,2-a]pyridin-2-yl) methanamine and 0.055 g (0.596 mmol) of 2-oxoacetic acid hydrate solubilised in 3 ml of methanol was added. The mixture was stirred under a slow vortex at r.t. for 24 h. The resin was removed by filtration, washed with 15 ml of methanol, 15 ml of dichloromethane and then again 15 ml of methanol. The obtained filtrate was concentrated in vacuo and the residue was purified by flash chromatography on a silica gel cartridge (eluent: dichloromethane/methanol/aqueous ammonia (20% by mass), 80/20/2, v/v/v). 0.049 g (yield=22%) of 2-(((3-((3-(trifluoromethyl)phenyl)ethynyl) imidazo[1,2-a]pyridin-2-yl)methyl)amino) acetic acid were obtained as a white solid. LC-MS: m/z=374 (MH$^+$); UV purity at 254 nm=98%. $^1$H NMR (300 MHz, DMSO) δ 8.76 (d, J=6.7 Hz, 1H), 8.13 (s, 1H), 8.01 (d, J=7.6 Hz, 1H), 7.78 (d, J=7.9 Hz, 1H), 7.69 (dd, J=8.3, 7.1 Hz, 2H), 7.53-7.42 (m, 1H), 7.16 (td, J=6.8, 1.0 Hz, 1H), 4.17 (s, 2H), 3.31 (s, 6H).

Example 13

Preparation of Derivative No. 69: N-((3-((3-(trifluoro methyl)phenyl)ethynyl)imidazo[1,2-a]pyridin-2-yl) methyl) propane-2-sulfonamide

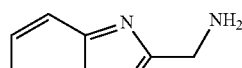

0.08 g (0.239 mmol) of (3-((3-(trifluoromethyl)phenyl) ethynyl) imidazo[1,2-a]pyridin-2-yl) methanamine (prepared according to steps 1 to 4 of Example 11) were solubilised in 2 ml of dichloromethane with magnetic stirring, 0.208 ml (1.193 mmol) of diisopropylethylamine and 0.083 ml (0.716 mmol) of isopropylsulfonyl chloride were added. The mixture was stirred at r.t. for 16 h. A supplement of 0.083 ml (0.716 mmol) of isopropylsulfonyl chloride was added and the mixture was stirred at r.t. for 1 h before being concentrated in vacuo. The crude residue was directly purified by flash chromatography on a silica gel cartridge (eluent: dichloromethane/methanol 95/5, v/v). 0.048 g (yield=22%) of N-((3-((3-(trifluoromethyl)phenyl)ethynyl) imidazo[1,2-a]pyridin-2-yl)methyl)propane-2-sulfonamide were obtained as a white solid. LC-MS: m/z=422 (MH$^+$); UV purity at 254 nm=98%. $^1$H NMR (300 MHz, DMSO) δ 8.75 (d, J=6.8 Hz, 1H), 8.13 (s, 1H), 7.99 (d, J=7.5 Hz, 1H), 7.85-7.61 (m, 4H), 7.53-7.38 (m, 1H), 7.15 (t, J=6.8 Hz, 1H), 4.44 (d, J=5.9 Hz, 2H), 3.25 (dd, J=13.6, 6.8 Hz, 1H), 1.21 (d, J=6.8 Hz, 6H).

Derivatives numbers 70 and 71 were prepared according to the same procedure.

| No. | Molecular weight g/mol | Aspect | LCMS purity UV at 254 nm | Mass spectrometry MH$^+$ M-H$^+$ | $^1$H NMR (300 MHz, DMSO) δ |
|---|---|---|---|---|---|
| 70 | 353.44 | solid | 99 | 354 | 8.79 (d, J = 6.7 Hz, 1H), 7.89-7.61 (m, 4H), 7.49 (dd, J = 5.1, 1.8 Hz, 3H), 7.33 (s, 1H), 4.49 (d, J = 5.8 Hz, 2H), 4.03 (s, 1H), 3.40-3.22 (m, 1H), 1.23 (d, J = 6.8 Hz, 6H). |
| 71 | 385.38 | | 99 | 386 | 8.73 (d, J = 6.7 Hz, 1H), 8.38 (s, 1H), 8.12 (s, 1H), 7.97 (d, J = 7.5 Hz, 1H), 7.82-7.58 (m, 3H), 7.52-7.37 (m, 1H), 7.13 (t, J = 6.7 Hz, 1H), 4.55 (d, J = 5.4 Hz, 2H), 2.48-2.36 (m, 1H), 0.98 (d, J = 6.8 Hz, 6H). |

Example 14

Preparation of Derivative Number 72: methyl 2-(methyl((3-((3-(trifluoromethyl)phenyl)ethynyl)imidazo[1,2-a]pyridin-2-yl)methyl)amino)acetate Step 1: Preparation of methyl 2-((imidazo[1,2-a]pyridin-2-ylmethyl)(methyl)amino)acetate

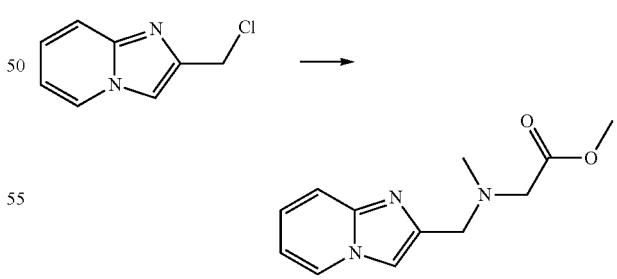

0.303 g (1.773 mmol) of 2-(chloromethyl)imidazo[1,2-a]pyridine were dissolved in 15 ml of dimethylformamide with magnetic stirring and then 0.253 g (1.773 mmol) of sarcosine methylester hydrochloride and 0.741 ml (5.32 mmol) of triethylamine were added. The mixture was stirred at r.t. for 16 h, and then treated with 30 ml of a saturated NaCl aqueous solution. The aqueous phase was concentrated in vacuo. The residue was triturated in 75 ml of isopropanol, the salts were removed by filtration and the filtrate was concentrated in vacuo. The crude residue was purified by flash chromatography on a silica gel cartridge (eluent: dichloromethane/methanol, 95/5, v/v). 0.107 g (yield=26%) of methyl 2-((imidazo[1,2-a]pyridin-2-ylmethyl)(methyl)amino)acetate were obtained as a pale yellow oil. LC-MS: m/z=234 (MH$^+$); UV purity at 254 nm=99%. $^1$H NMR (300 MHz, DMSO) δ 8.49 (d, J=6.8 Hz, 1H), 7.79 (s, 1H), 7.47 (d, J=9.0 Hz, 1H), 7.18 (ddd, J=9.0, 6.7, 1.2 Hz, 1H), 6.84 (td, J=6.7, 1.1 Hz, 1H), 3.76 (s, 2H), 3.61 (s, 3H), 2.32 (s, 3H).

Step 2: Preparation of methyl 2-(((3-iodoimidazo[1,2-a]pyridin-2-yl)methyl)(methyl)amino)acetate

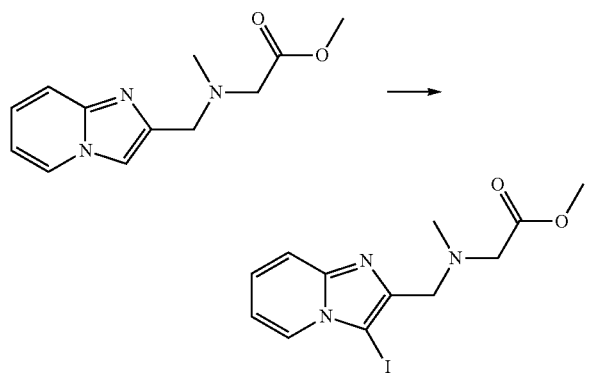

0.107 g (0.459 mmol) of methyl 2-((imidazo[1,2-a]pyridin-2-ylmethyl)(methyl)amino)acetate were dissolved in 4 ml of acetonitrile with magnetic stirring, to this solution were added 0.112 g (0.482 mmol) of N-iodosuccinimide. The mixture was stirred at r.t. for 16 h. The reaction mixture was treated with 10 ml of water and then extracted with 3×10 ml of ethyl acetate. The combined organic phases were washed with 20 ml of a saturated NaCl aqueous solution, and then dried on Na$_2$SO$_4$ which was then removed by filtration. The obtained filtrate was concentrated in vacuo. The crude residue was purified by flash chromatography on a silica gel cartridge (eluent: ethyl acetate 100%). 0.093 g (yield=46%) of methyl 2-(((3-iodoimidazo[1,2-a]pyridin-2-yl)methyl)(methyl)amino)acetate were obtained as a yellow oil. LC-MS: m/z=360 (MH$^+$); UV purity at 254 nm=82%. $^1$H NMR (300 MHz, DMSO) δ 8.30 (d, J=6.8 Hz, 1H), 7.54 (d, J=9.0 Hz, 1H), 7.41-7.23 (m, 1H), 7.03 (t, J=6.7 Hz, 1H), 3.79 (s, 2H), 3.62 (s, 3H), 3.37 (s, 2H), 2.34 (s, 3H).

Step 3: Preparation of methyl 2-(methyl((3-((3-(trifluoromethyl)phenyl)ethynyl)imidazo[1,2-a]pyridin-2-yl)methyl)amino)acetate (Derivative Number 72)

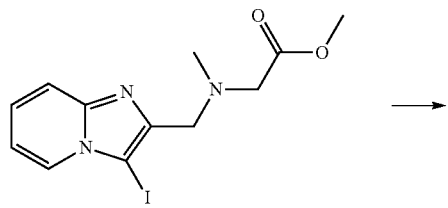

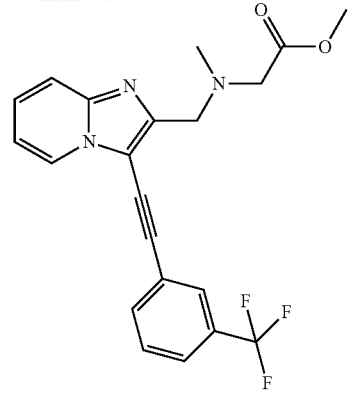

In a flask placed under an argon flow, 0.093 g (0.212 mmol) of methyl 2-(((3-iodoimidazo[1,2-a]pyridin-2-yl)methyl)(methyl)amino)acetate were dissolved in 0.5 ml of dimethylformamide with magnetic stirring. To this solution, were added: 0.004 g (0.021 mmol) of copper iodide, 0.037 ml (0.255 mmol) of 3-trifluoromethylphenylacetylene and 0.444 ml (3.18 mmol) of triethylamine. The reaction medium was degassed with argon for 10 min before adding 0.019 g (0.021 mmol) of Pd$_2$(dba)$_3$. The mixture was stirred at r.t. for 16 h before being treated, diluted with 15 ml of ethyl acetate and washed with 2×15 ml of a saturated NaCl aqueous solution. The aqueous phase was extracted with 20 ml of ethyl acetate. The combined organic phases were dried on Na$_2$SO$_4$ which was then removed by filtration. The obtained filtrate was concentrated in vacuo. The crude residue was purified by flash chromatography on a silica gel cartridge (eluent: ethyl acetate 100%). 0.05 g (yield=57%) of methyl 2-(methyl((3-((3-(trifluoromethyl)phenyl)ethynyl)imidazo[1,2-a]pyridin-2-yl)methyl)amino)acetate were obtained as a pale brown solid. LC-MS: m/z=402 (MH$^+$); UV purity at 254 nm=96%. $^1$H NMR (300 MHz, DMSO) δ 8.75 (d, J=6.7 Hz, 1H), 8.11 (s, 1H), 7.97 (d, J=7.6 Hz, 1H), 7.83-7.59 (m, 3H), 7.55-7.37 (m, 1H), 7.14 (td, J=6.8, 0.9 Hz, 1H), 3.97 (s, 2H), 3.58 (s, 3H), 3.43 (s, 2H), 2.39 (s, 3H).

Derivatives numbers 101 to 104 were prepared according to the same procedure.

| No. | Molecular weight g/mol | Aspect | LCMS purity UV at 254 | Mass spectrometry m/z MH$^+$ | M-H$^+$ | $^1$H NMR (300 MHz, DMSO) δ |
|---|---|---|---|---|---|---|
| 101 | 451.13 | yellow solid | 99 | 416 | | 8.87 (d, J = 6.7 Hz, 1H), 8.20 (s, 1H), 8.08 (d, J = 7.5 Hz, 1H), 7.79 (dt, J = 15.6, 8.4 Hz, 3H), 7.65-7.53 (m, 1H), 7.26 (t, J = 6.7 Hz, 1H), 4.69 (s, 2H), 4.32 (s, 2H), 4.23-4.16 (m, 4H), 2.97 (s, 3H), 1.20 (t, J = 7.1 Hz, 3H). |
| 102 | 449.85 | beige solid | | 450 | | 8.95 (s, 1H), 8.14 (s, 1H), 8.00 (d, J = 7.5 Hz, 1H), 7.73 (dt, J = 15.5, 7.8 Hz, 3H), 7.48 (d, J = 8.3 Hz, 1H), 4.04 (d, J = 7.0 Hz, 2H), 3.96 (s, 2H), 3.39 (s, 2H), 2.38 (s, 3H), 1.13 (t, J = 7.0 Hz, 3H). |

| No. | Molecular weight g/mol | Aspect | LCMS purity UV at 254 | Mass spectrometry m/z MH+ M-H+ | $^1$H NMR (300 MHz, DMSO) δ |
|---|---|---|---|---|---|
| 103 | 431.41 | yellow solid | 99 | 432 | 8.83 (d, J = 6.7 Hz, 1H), 7.88-7.77 (m, 3H), 7.59 (ddd, J = 27.9, 17.8, 8.1 Hz, 3H), 7.26 (t, J = 6.7 Hz, 1H), 4.68 (s, 2H), 4.32 (s, 2H), 4.20 (d, J = 7.1 Hz, 2H), 2.97 (s, 3H), 1.21 (t, J = 7.1 Hz, 3H). |
| 104 | 465.85 | brown solid | 99 | 466 | 9.08 (s, 1H), 7.85 (dd, J = 13.6, 6.0 Hz, 3H), 7.69-7.60 (m, 2H), 7.50 (d, J = 8.3 Hz, 1H), 4.64 (s, 2H), 4.28 (s, 2H), 4.19 (dd, J = 14.1, 7.0 Hz, 2H), 2.93 (s, 3H), 1.20 (t, J = 7.1 Hz, 3H). |

Example 15

Preparation of Derivative Number 73: 2-(methyl((3-((3-(trifluoromethyl)phenyl)ethynyl)imidazo[1,2-a]pyridin-2-yl)methyl)amino)acetic acid

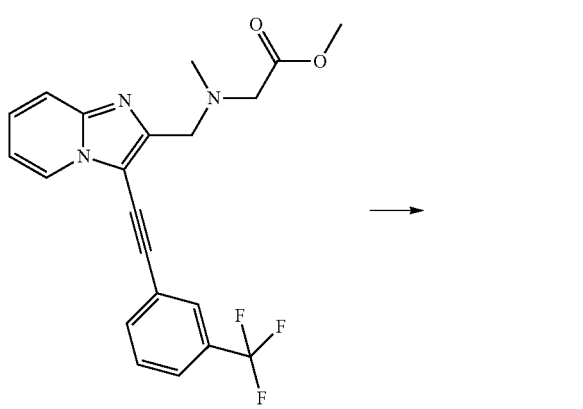

0.22 g (0.543 mmol) of 2-(methyl((3-((3-(trifluoromethyl)phenyl) ethynyl) imidazo[1,2-a]pyridin-2-yl)methyl)amino) acetate were dissolved in 6 ml of a mixture consisting of methanol and tetrahydrofurane with magnetic stirring and then 0.543 ml (0.543 mmol) of a 1M NaOH aqueous solution were added. The mixture was stirred at r.t. for 16 h. 0.163 ml (0.163 mmol) of a 1M NaOH aqueous solution were added. The mixture was stirred at r.t. for a further 24 h before being treated with a solution of 0.04 ml (0.705 mmol) of acetic acid in 10 ml of water. The mixture was stirred at r.t. for 30 min. The solid formed was isolated by filtration, washed with 5 ml of water and dried in a vacuum bell jar in order to obtain 0.155 g (yield=73%) of 2-(methyl((3-((3-(trifluoromethyl)phenyl) ethynyl)imidazo[1,2-a]pyridin-2-yl)methyl)amino) acetic acid as a beige solid. LC-MS: m/z=388 (MH+); UV purity at 254 nm=99%. $^1$H NMR (300 MHz, DMSO) δ 8.74 (d, J=6.7 Hz, 1H), 8.10 (s, 1H), 7.97 (d, J=7.6 Hz, 1H), 7.77 (d, J=7.8 Hz, 1H), 7.74-7.64 (m, 2H), 7.49-7.39 (m, 1H), 7.13 (t, J=6.4 Hz, 1H), 4.02 (s, 2H), 3.59 (s, 1H), 3.33 (s, 2H), 2.41 (s, 3H).

Derivatives numbers 105 to 107 were prepared according to the same procedure.

| No. | Molecular weight g/mol | Aspect | LCMS purity UV at 254 | Mass spectrometry m/z MH+ M-H+ | $^1$H NMR (300 MHz, DMSO) δ |
|---|---|---|---|---|---|
| 105 | 437.8 | green solid | 99 | 438 | 9.08 (s, 1H), 7.91-7.80 (m, 3H), 7.63 (s, 2H), 7.50 (d, J = 7.2 Hz, 1H), 4.65 (s, 2H), 4.19 (s, 2H), 2.92 (s, 1H), 1.23 (s, 3H). |
| 106 | 403.36 | brown solid | 99 | 404 | 8.79 (d, J = 5.9 Hz, 1H), 7.88-7.71 (m, 3H), 7.63 (t, J = 7.8 Hz, 1H), 7.56-7.42 (m, 2H), 7.22 (d, J = 6.3 Hz, 1H), 4.48 (s, 2H), 3.97 (s, 2H), 2.79 (s, 1H), 1.03 (d, J = 5.8 Hz, 3H). |
| 107 | 421.8 | brown solid | 99 | 422 | 8.96 (s, 1H), 8.15 (s, 1H), 8.01 (s, 1H), 7.74 (dd, J = 24.9, 7.0 Hz, 3H), 7.52 (s, 1H), 3.94 (s, 2H), 3.03 (s, 2H), 2.33 (s, 3H). |

Example 16

Preparation of Derivative Number 74: methyl 3-(3-((3-((3-(trifluoromethyl)phenyl)ethynyl)imidazo[1,2-a]pyridin-2-yl)methyl)ureido)benzoate

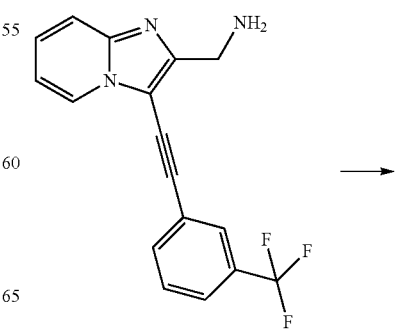

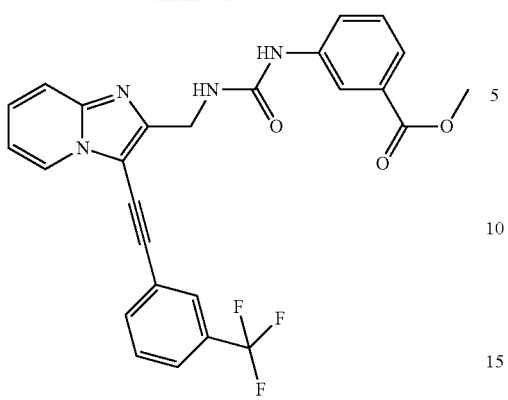

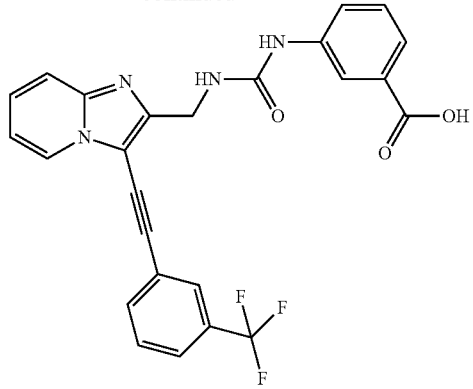

0.15 g (0.477 mmol) of (3-((3-(trifluoromethyl)phenyl)ethynyl)imidazo[1,2-a]pyridin-2-yl)methanamine (prepared according to steps 1 to 4 of Example 11) were dissolved in 4 ml of dichloromethane with magnetic stirring and then 0.09 g (0.492 mmol) of methyl benzoate-3-isocyanate. The mixture was stirred at r.t. for 15 min. The solid formed was isolated by filtration and washed with 10 ml of dichloromethane. The solid was then purified by preparative HPLC in order to obtain 0.057 g (yield=25%) of methyl 3-(3-((3-((3-(trifluoromethyl)phenyl)ethynyl)imidazo[1,2-a]pyridin-2-yl)methyl) ureido)benzoate as a white powder. LC-MS: m/z=493 (MH+); UV purity at 254 nm=98%. $^1$H NMR (300 MHz, DMSO) δ), 8.74 (d, J=6.7 Hz, 1H), 8.11 (t, J=1.8 Hz, 1H), 8.04 (s, 1H), 7.91 (d, J=7.8 Hz, 1H), 7.70 (dd, J=13.0, 8.5 Hz, 2H), 7.58 (t, J=7.9 Hz, 2H), 7.53-7.42 (m, 2H), 7.34 (t, J=7.9 Hz, 1H), 7.15 (td, J=6.8, 1.1 Hz, 1H), 6.81 (t, J=5.7 Hz, 1H), 4.64 (d, J=5.7 Hz, 2H), 3.83 (s, 3H).

0.038 g (0.078 mmol) of methyl 3-(3-((3-((3-(trifluoromethyl)phenyl)ethynyl) imidazo[1,2-a]pyridin-2-yl)methyl) ureido)benzoate were dissolved in 2 ml of a methanol/tetrahydrofurane mixture (1/1, v/v) with magnetic stirring and then 0.931 ml (0.931 mmol) of a (1M) NaOH aqueous solution were added and the mixture was stirred at r.t. for 16 h before being treated with a solution of 0.053 ml (0.931 mmol) of acetic acid in 10 ml of water. The mixture was stirred at r.t. for 30 min. The solid formed was isolated by filtration, washed with 5 ml of water and dried in a vacuum bell jar in order to obtain 0.026 g (yield=70%) of 3-(3-((3-((3-(trifluoromethyl)phenyl)ethynyl)imidazo[1,2-a]pyridin-2-yl)methyl) ureido) benzoic acid as a white solid. LC-MS: m/z=479 (MH+); UV purity at 254 nm=99%. $^1$H NMR (300 MHz, DMSO) δ 12.83 (s, 1H), 8.96 (s, 1H), 8.73 (d, J=6.7 Hz, 1H), 8.04 (s, 2H), 7.90 (d, J=7.5 Hz, 1H), 7.69 (dd, J=13.0, 8.4 Hz, 2H), 7.58 (d, J=7.7 Hz, 2H), 7.45 (d, J=7.5 Hz, 2H), 7.29 (t, J=7.9 Hz, 1H), 7.13 (t, J=6.8 Hz, 1H), 6.80 (t, J=5.4 Hz, 1H), 4.62 (d, J=5.6 Hz, 2H).

Example 17

Preparation of Derivative Number 75: 3-(3-((3-((3-(trifluoromethyl)phenyl)ethynyl)imidazo[1,2-a]pyridin-2-yl)methyl)ureido)benzoic acid

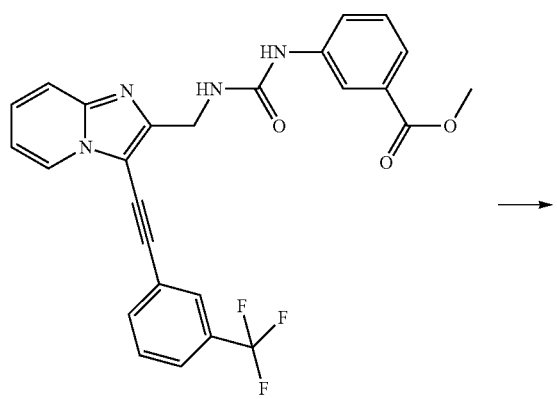

Example 18

Preparation of Derivative No. 76: methyl 2-((3-((4-fluorophenyl)ethynyl)imidazo[1,2-a]pyridin-2-yl)methoxy)-benzoate Step 1: Preparation of methyl 2-((3-iodoimidazo[1,2-a]pyridin-2-yl)methoxy)benzoate

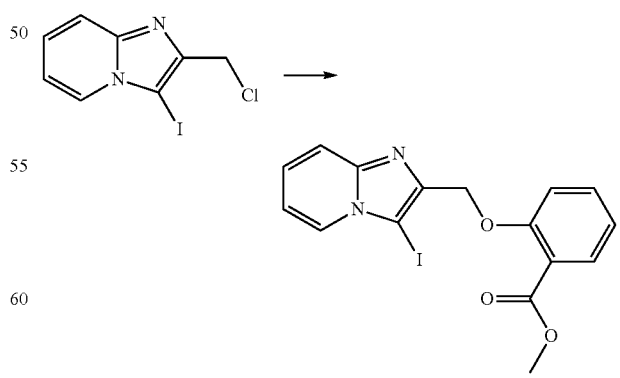

4 g (13.68 mmol) of 2-(chloromethyl)-3-iodoimidazo[1,2-a]pyridine were dissolved in dimethylformamide with magnetic stirring and then 2.71 ml (20.51 mmol) of methyl 2-hydroxybenzoate and 6.68 g (20.51 mmol) of cesium carbonate were added. The mixture was stirred at 60° C. for 2 h before being poured into 200 ml of water. The aqueous phase was extracted with 2×100 ml of ethyl acetate. The combined organic phases were washed with 100 ml of a saturated NaHCO$_3$ aqueous solution, 100 ml of a saturated NaCl aqueous solution, dried on Na$_2$SO$_4$ which was then removed by filtration. The obtained filtrate was concentrated in vacuo. The crude residue was triturated in 50 ml of diisopropyl ether, the obtained solid was isolated by filtration. 2.55 g of expected product were isolated. On the other hand, an aqueous phase suspension was isolated by filtration and washed with 2×30 ml of water. The analyses confirmed that this was also the expected product. Both batches were therefore collected and 5.58 g (yield=76%) of methyl 2-((3-iodoimidazo[1,2-a]pyridin-2-yl) methoxy)benzoate were obtained as a white powder. LC-MS: m/z=409 (MH$^+$); UV purity at 254 nm=98%. $^1$H NMR (300 MHz, DMSO) δ 8.33 (d, J=6.9 Hz, 1H), 7.69-7.44 (m, 3H), 7.45-7.28 (m, 2H), 7.16-6.93 (m, 2H), 5.23 (s, 2H), 3.73 (s, 3H).

Step 2: Preparation of methyl 2-((3-((4-fluorophenyl)ethynyl)imidazo[1,2-a]pyridin-2-yl)methoxy)benzoate (Derivative No. 76)

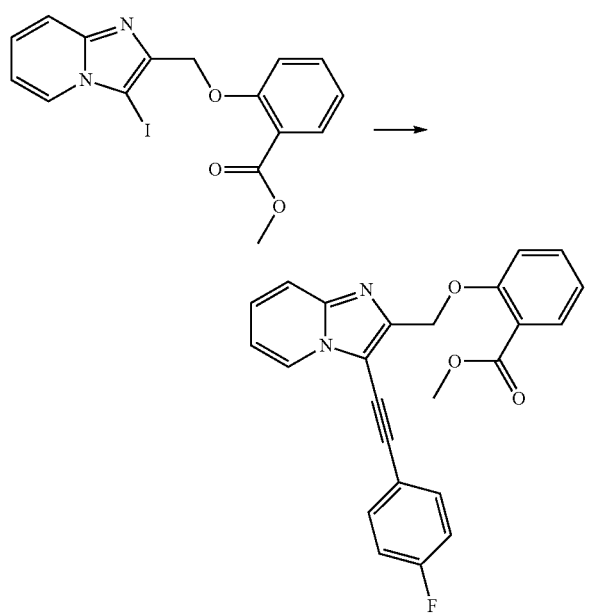

In a flask placed under an argon flow, 2 g (3.82 mmol) of methyl 2-((3-iodoimidazo[1,2-a]pyridin-2-yl)methoxy)benzoate were dissolved in 8 ml of dimethylformamide with magnetic stirring. To this solution were added: 0.074 g (0.382 mmol) of copper iodide, 0.551 g (4.59 mmol) of 1-ethynyl-4-fluorobenzene and 8 ml (57.3 mmol) of triethylamine. The reaction medium was degassed with argon for 10 min before adding 0.35 g (0.382 mmol) of Pd$_2$(dba)$_3$. The mixture was stirred at r.t. for 16 h before being treated with 100 ml of a saturated NaCl aqueous solution. The aqueous phase was extracted with 2×100 ml of ethyl acetate. The combined organic phases were washed with 100 ml of a saturated NaCl aqueous solution, dried on Na$_2$SO$_4$ which was then removed by filtration. The obtained filtrate was concentrated in vacuo. The crude residue was purified by flash chromatography on a silica gel cartridge (eluent: heptane/ethyl acetate, 1/1, v/v). 1.36 g (yield=84%) of methyl 2-((3-((4-fluorophenyl)ethynyl) imidazo[1,2-a]pyridin-2-yl)methoxy)benzoate were obtained as a pale brown solid. LC-MS: m/z=401 (MH$^+$); UV purity at 254 nm=98%. $^1$H NMR (300 MHz, DMSO) δ 8.63 (d, J=6.7 Hz, 1H), 7.75-7.59 (m, 4H), 7.48 (ddd, J=15.9, 11.5, 4.8 Hz, 2H), 7.40-7.26 (m, 3H), 7.13 (t, J=6.8 Hz, 1H), 7.01 (t, J=7.4 Hz, 1H), 5.40 (s, 2H), 3.68 (s, 3H).

Derivatives numbers 77 to 86 were prepared according to the same sequence of steps 1 and 2.

| No. | Molecular weight g/mol | Aspect | LCMS purity UV at 254 nm | Mass spectrometry MH$^+$ M-H$^+$ | $^1$H NMR (300 MHz, DMSO) δ |
|---|---|---|---|---|---|
| 77 | 450.41 | brown solid | 99 | 451 | 8.77 (d, J = 6.7 Hz, 1H), 8.03 (s, 1H), 7.91 (d, J = 7.6 Hz, 1H), 7.83-7.59 (m, 4H), 7.57-7.44 (m, 2H), 7.36 (d, J = 8.4 Hz, 1H), 7.15 (dd, J = 14.3, 7.5 Hz, 1H), 7.02 (t, J = 7.5 Hz, 1H), 5.46 (s, 2H), 3.68 (s, 3H). |
| 78 | 382.11 | yellow solid | 95 | 383 | $^1$H NMR(DMSO-D6): 8.63 (d, J = 6.8 Hz, 1H), 7.79-7.57 (m, 4H), 7.57-7.35 (m, 6H), 7.14 (tt, J = 10.1, 5.0 Hz, 1H), 7.02 (td, J = 7.6, 0.9 Hz, 1H), 5.41 (s, 2H), 3.68 (s, 3H). |
| 79 | 407.21 | Solid | 92 | 408 | 8.73 (d, J = 6.7 Hz, 1H), 8.15 (s, 1H), 8.00-7.82 (m, 2H), 7.79-7.59 (m, 3H), 7.50 (td, J = 8.1, 3.9 Hz, 2H), 7.36 (d, J = 8.3 Hz, 1H), 7.16 (t, J = 6.8 Hz, 1H), 7.02 (t, J = 7.5 Hz, 1H), 5.44 (s, 2H), 3.69 (s, 3H). |
| 80 | 381.40 | brown oil | 93.1 | 382 | 8.52 (d, J = 6.8 Hz, 1H), 7.69 (s, 1H), 7.62-7.52 (m, 5H), 7.45-7.34 (m, 2H), 7.22 (d, J = 8.9 Hz, 2H), 7.02 (t, J = 6.8 Hz, 1H), 4.68 (s, 2H), 4.58 (s, 2H). |
| 81 | 450.41 | brown solid | 99 | 451 | 8.81-8.71 (m, 1H), 8.04 (s, 1H), 7.94 (d, J = 7.7 Hz, 1H), 7.84-7.61 (m, 4H), 7.58-7.30 (m, 4H), 7.16 (td, J = 6.8, 1.1 Hz, 1H), 5.45 (s, 2H), 3.78 (s, 3H). |
| 82 | 382.41 | brown solid | 95 | 383 | 8.64 (d, J = 6.8 Hz, 1H), 7.97-7.85 (m, 2H), 7.75-7.59 (m, 3H), 7.52-7.39 (m, 4H), 7.26-7.10 (m, 3H), 5.42 (s, 2H), 3.79 (s, 3H). |
| 83 | 450.41 | brown solid | 96 | 451 | 8.78 (d, J = 6.7 Hz, 1H), 8.04 (s, 1H), 7.92 (t, J = 8.1 Hz, 3H), 7.73 (dt, J = 13.9, 7.8 Hz, 3H), 7.56-7.41 (m, 1H), 7.27-7.09 (m, 3H), 5.47 (s, 2H), 3.80 (s, 3H). |

-continued

| No. | Molecular weight g/mol | Aspect | LCMS purity UV at 254 nm | Mass spectrometry MH+ M-H+ | 1H NMR (300 MHz, DMSO) δ |
|---|---|---|---|---|---|
| 84 | 324.38 | orangey solid | 99 | 325 | 8.64 (dd, J = 6.8, 1.0 Hz, 1H), 7.77-7.59 (m, 3H), 7.53-7.40 (m, 4H), 7.30 (ddd, J = 7.5, 5.8, 2.2 Hz, 2H), 7.21-7.04 (m, 3H), 6.95 (t, J = 7.3 Hz, 1H), 5.33 (s, 2H). |
| 85 | 367.38 | solid | 97 | 368 | 8.66 (d, J = 6.8 Hz, 1H), 7.79-7.68 (m, 3H), 7.63 (s, 1H), 7.55-7.40 (m, 4H), 7.33 (t, J = 8.9 Hz, 2H), 7.15 (td, J = 6.8, 1.0 Hz, 1H), 5.42 (s, 2H). |
| 86 | 431.41 | beige solid | >99 | 432 | 8.75 (d, J = 5.9 Hz, 1H), 7.97 (s, 1H), 7.91-7.62 (m, 7H), 7.58-7.40 (m, 2H), 7.15 (t, J = 6.8 Hz, 1H), 4.82 (s, 2H), 4.70 (s, 2H). |

Example 19

Preparation of Derivative Number 87: methyl 3-((3-(phenylethynyl)imidazo[1,2-a]pyridin-2-yl)methoxy)benzoate Step 1: Preparation of ethyl imidazo[1,2-a]pyridine-2-carboxylate

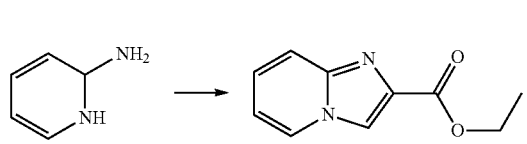

3 g (31.9 mmol) of 2-aminopyridine were dissolved in 65 ml of tetrahydrofurane with magnetic stirring. The addition of 4.44 ml (31.9 mmol) of ethyl bromopyruvate caused precipitation of a solid. The heterogenous mixture was stirred with reflux for 4 h. After returning to r.t., the solid was isolated by filtration and taken up in 65 ml of ethanol in order to be stirred with reflux in 65 ml of ethanol for 16 h. After returning to r.t., the solid was isolated by filtration. The filtrate was placed in ice in order to facilitate crystallization of the product which was collected by filtration and thus so forth until the liquid phase remained limpid. The solid was rinsed with 30 ml of diisopropyl ether and dried in a vacuum bell jar in order to obtain 5.14 g (yield=84%) of ethyl imidazo[1,2-a]pyridine-2-carboxylate as a white powder. LC-MS: m/z=191 (MH+); UV purity at 254 nm=99%. 1H NMR (300 MHz, DMSO) δ 8.95 (s, 1H), 8.84 (d, J=6.8 Hz, 1H), 7.98-7.80 (m, 2H), 7.46 (t, J=7.2 Hz, 1H), 4.43 (q, J=7.1 Hz, 2H), 1.35 (d, J=7.1 Hz, 3H).

Step 2: Preparation of ethyl 3-iodoimidazo[1,2-a]pyridine-2-carboxylate

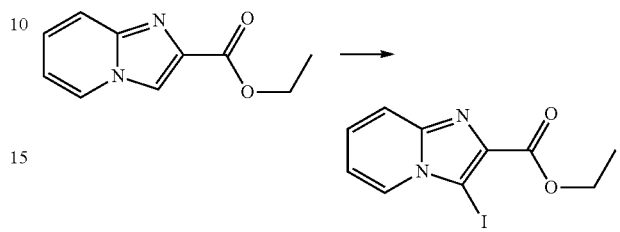

2.405 g (12.16 mmol) of ethyl imidazo[1,2-a]pyridine-2-carboxylate were dissolved in 60 ml of acetonitrile with magnetic stirring, to this solution were added 3.01 g (13.38 mmol) of N-iodosuccinimide. The mixture was stirred at r.t. for 1 h. The reaction mixture was treated with 50 ml of 100 mg/ml $Na_2S_2O_5$ aqueous solution. The aqueous phase was extracted with 2×100 ml of ethyl acetate. The aqueous phase was neutralized by adding $NaHCO_3$ portionwise and then extracted with 3×100 ml of ethyl acetate. The whole of the organic phases was combined and then washed with 200 ml of a saturated NaCl aqueous solution, and then dried on $Na_2SO_4$ which was then removed by filtration. The obtained filtrate was concentrated in vacuo in order to obtain 1.59 g (yield=41%) of ethyl 3-iodoimidazo[1,2-a]pyridine-2-carboxylate as a pale yellow solid. LC-MS: m/z=317 (MH+); UV purity at 254 nm=99%. 1H NMR (300 MHz, DMSO) δ 8.45 (d, J=6.9 Hz, 1H), 7.66 (d, J=9.1 Hz, 1H), 7.46 (d, J=7.0 Hz, 1H), 7.15 (d, J=6.6 Hz, 1H), 4.30 (d, J=7.1 Hz, 2H), 1.36 (d, J=7.1 Hz, 3H).

Step 3: Preparation of ethyl 3-(phenylethynyl)imidazo[1,2-a]pyridine-2-carboxylate

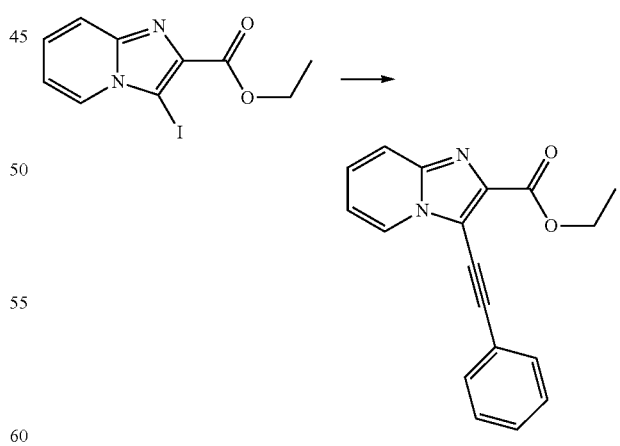

In a flask placed under an argon flow, 1.82 g (5.77 mmol) of ethyl 3-iodoimidazo[1,2-a]pyridine-2-carboxylate were dissolved in 6 ml of dimethylformamide with magnetic stirring. To this solution were added: 0.11 g (0.577 mmol) of copper iodide, 0.776 ml (6.93 mmol) of phenylacetylene and 6 ml (43 mmol) of triethylamine. The reaction medium was degassed with argon for 10 min before adding 0.529 g (0.577 mmol) of Pd₂(dba)₃. The mixture was stirred at r.t. for 16 h before being filtered on celite. The celite was washed with 50 ml of ethyl acetate, and then the filtrate was washed with 2×50 ml of water. After separation, the aqueous phase was extracted with 2×50 ml of ethyl acetate; the combined organic phases were washed with 70 ml of a saturated NaCl aqueous solution, dried on Na₂SO₄ which was then removed by filtration. The obtained filtrate was concentrated in vacuo. The crude residue was purified by flash chromatography on a silica gel cartridge (eluent: heptane/ethyl acetate, 6/4, v/v). 1.28 g (yield=57%) of ethyl 3-(phenylethynyl)imidazo[1,2-a]pyridine-2-carboxylate were obtained as a pale yellow solid. LC-MS: m/z=291 (MH⁺); UV purity at 254 nm=93%. ¹H NMR (300 MHz, DMSO) δ 8.70 (d, J=6.8 Hz, 1H), 7.74 (dd, J=22.1, 6.2 Hz, 3H), 7.53 (dd, J=17.6, 6.9 Hz, 4H), 7.23 (t, J=6.3 Hz, 1H), 4.36 (d, J=4.7 Hz, 2H), 1.36 (d, J=7.1 Hz, 3H).

Step 4: Preparation of (3-(phenylethynyl)imidazo[1, 2-a]pyridin-2-yl)methanol

In a flask placed under an argon flow, 0.078 g (1.984 mmol) of LAH were dissolved in 1.4 ml of tetrahydrofurane and then with vigorous magnetic stirring, a solution of 0.3 g (0.992 mmol) of ethyl 3-(phenylethynyl)imidazo[1,2-a]pyridine-2-carboxylate in 3.3 ml of tetrahydrofurane was added drop wise. The mixture was stirred at r.t. for 15 min and then 0.2 ml of water were added with caution, followed by a solution of 0.2 ml of sulfuric acid in 1.5 ml of water. After separation, the organic phase was washed with 50 ml of water. The aqueous phase was extracted with 3×50 ml of ethyl acetate and then the combined organic phases were washed with 100 ml of a saturated NaCl aqueous solution and then dried on Na₂SO₄ which was then removed by filtration. The obtained filtrate was concentrated in vacuo. The crude residue was purified by flash chromatography on a silica gel cartridge (eluent: heptane/ethyl acetate gradient, from 40% to 30% of heptane, v/v). 0.076 g (yield=30%) of (3-(phenylethynyl)imidazo[1, 2-a]pyridin-2-yl)methanol were obtained as a pale yellow solid. LC-MS: m/z=249 (MH⁺); UV purity at 254 nm=97%. ¹H NMR (300 MHz, DMSO) δ 8.59 (dt, J=6.7, 1.1 Hz, 1H), 7.77-7.56 (m, 3H), 7.56-7.32 (m, 4H), 7.11 (td, J=6.8, 1.1 Hz, 1H), 5.33 (t, J=5.9 Hz, 1H), 4.67 (d, J=5.9 Hz, 2H).

Step 5: Preparation of methyl 3-((3-(phenylethynyl) imidazo[1,2-a]pyridin-2-yl)methoxy)benzoate (Derivative No. 87)

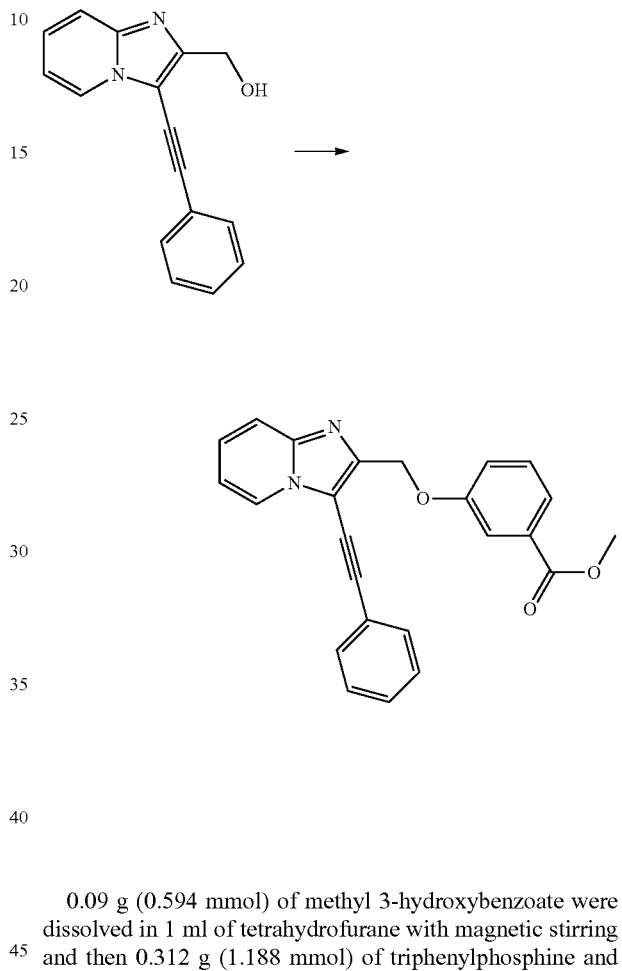

0.09 g (0.594 mmol) of methyl 3-hydroxybenzoate were dissolved in 1 ml of tetrahydrofurane with magnetic stirring and then 0.312 g (1.188 mmol) of triphenylphosphine and 0.231 ml (1.188 mmol) of DIAD were added. The mixture was stirred at r.t. for 15 min and then a solution of 0.076 g (0.297 mmol) of (3-(phenylethynyl)imidazo[1,2-a]pyridin-2-yl)methanol in 4 ml of tetrahydrofurane was added and the mixture was stirred at r.t. for 16 h. A mixture of 0.09 g (0.594 mmol) of methyl 3-hydroxybenzoate, 0.312 g (1.188 mmol) of triphenylphosphine and 0.231 ml (1.188 mmol) of DIAD dissolved in 1 ml of tetrahydrofurane was added and the reaction medium was stirred at r.t. for a further 2 h. The reaction medium was treated with 10 ml. The aqueous phase was extracted with 3×10 ml of ethyl acetate and then the combined organic phases were washed with 10 ml of a saturated NaCl solution and then dried on Na₂SO₄ which was then removed by filtration. The obtained filtrate was concentrated in vacuo. The crude residue was purified by flash chromatography on a silica gel cartridge (eluent: heptane/ethyl acetate, from 70% to 40% heptane, v/v). 0.048 g (yield=42%) of methyl 3-((3-(phenylethynyl)imidazo[1,2-a]pyridin-2-yl) methoxy)benzoate were obtained as a pale yellow solid. LC-MS: m/z=383 (MH⁺); UV purity at 254 nm=99%. ¹H NMR (300 MHz, DMSO) δ 8.64 (d, J=6.8 Hz, 1H), 7.68 (dd, J=17.0, 7.2 Hz, 4H), 7.55 (d, J=8.7 Hz, 1H), 7.52-7.34 (m, 6H), 7.15 (t, J=7.3 Hz, 1H), 5.42 (s, 2H), 3.80 (s, 3H).

Example 20

Preparation of Derivative No. 88: 2-((3-((4-fluoro phenyl)ethynyl)-imidazo[1,2-a]pyridin-2-yl)methoxy)benzoic acid

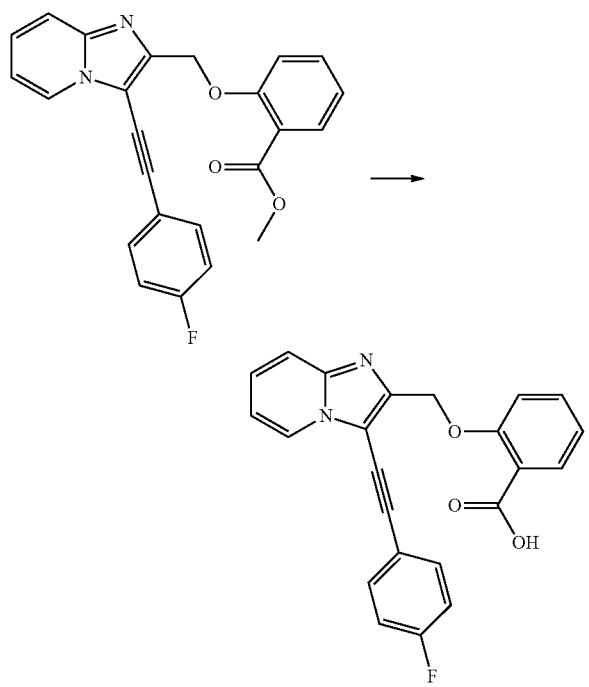

0.65 g (1.542 mmol) of methyl 2-((3-((4-fluorophenyl)ethynyl)imidazo[1,2-a]pyridin-2-yl)methoxy)benzoate were solubilized with magnetic stirring in 30 ml of a mixture consisting of ethanol and of tetrahydrofurane (1/1, v/v) and then 15.42 ml (15.42 mmol) of a 1N NaOH aqueous solution were added. The mixture was stirred at r.t. for 16 h before adding 20 ml of water and then 0.883 ml (15.42 mmol) of acetic acid. The formed precipitate was isolated by filtration, washed with 10 ml of water and dried in a vacuum bell jar in order to obtain 0.518 g (yield=81%) of 2-((3-((4-fluoro-phenyl)ethynyl)imidazo[1,2-a]pyridin-2-yl)methoxy)benzoic acid as a pale yellow solid. LC-MS: m/z=387 (MH$^+$); UV purity at 254 nm=99%. $^1$H NMR (300 MHz, DMSO) δ 12.72 (s, 1H), 8.64 (d, J=5.5 Hz, 1H), 7.78-7.59 (m, 4H), 7.45 (d, J=6.2 Hz, 2H), 7.41-7.24 (m, 3H), 7.14 (t, J=6.8 Hz, 1H), 7.00 (t, J=7.3 Hz, 1H), 5.42 (s, 2H).

Derivatives numbers 89 to 93 were prepared according to the same procedure.

| No. | Molecular weight g/mol | Aspect | LCMS purity UV at 254 nm | Mass spectrometry MH$^+$ | M-H$^+$ | $^1$H NMR (300 MHz, DMSO) δ |
|---|---|---|---|---|---|---|
| 89 | 436.38 | solid | 99 | 437 | 435 | 12.71 (s, 1H), 8.76 (d, J = 6.5 Hz, 1H), 8.05 (s, 1H), 7.93 (d, J = 7.6 Hz, 1H), 7.82-7.58 (m, 5H), 7.48 (dd, J = 13.1, 6.6 Hz, 3H), 7.36 (d, J = 8.3 Hz, 1H), 7.17 (t, J = 6.7 Hz, 1H), 7.01 (t, J = 7.4 Hz, 1H), 5.47 (s, 2H). |
| 90 | 436.38 | brown solid | 99 | 437 | | 12.66 (s, 1H), 8.78 (d, J = 6.8 Hz, 1H), 8.05 (s, 1H), 8.01-7.84 (m, 3H), 7.84-7.60 (m, 3H), 7.57-7.42 (m, 1H), 7.30-7.05 (m, 3H), 5.45 (s, 2H). |
| 91 | 390.37 | brown solid | 98 | 369 | | 8.63 (d, J = 6.8 Hz, 1H), 7.79 (d, J = 8.7 Hz, 2H), 7.65 (s, 3H), 7.45 (s, 4H), 7.15 (td, J = 6.8, 1.0 Hz, 1H), 6.96 (d, J = 8.8 Hz, 2H), 5.31 (s, 2H). |
| 92 | 390.37 | yellow solid | 98 | 369 | | 8.64 (d, J = 6.7 Hz, 1H), 7.85-7.62 (m, 3H), 7.56-7.37 (m, 4H), 7.29 (t, J = 7.7 Hz, 1H), 7.23-6.98 (m, 3H), 6.94-6.72 (m, 1H), 5.28 (s, 2H). |
| 93 | 368.39 | yellow solid | 98.6 | 369 | | 13.02 (s, 1H), 8.64 (d, J = 6.8 Hz, 1H), 7.76-7.59 (m, 4H), 7.59-7.32 (m, 7H), 7.15 (t, J = 6.3 Hz, 1H), 5.41 (s, 2H). |

Example 21

Preparation of Derivative No. 94: (2-((3-((3-(trifluoro methyl)phenyl)ethynyl)imidazo[1,2-a]pyridin-2-yl)methoxy)phenyl) methanol

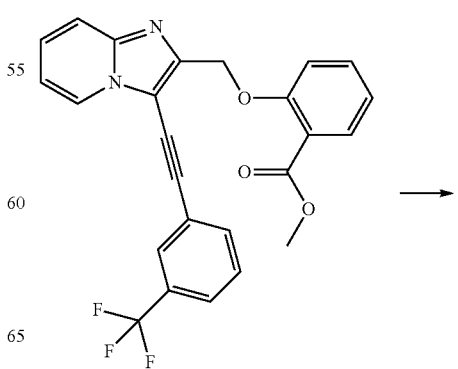

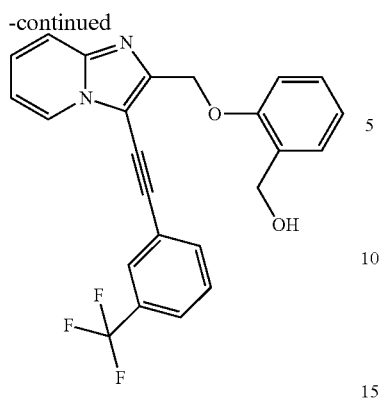

In a flask placed under an argon flow, 0.16 g (0.352 mmol) of methyl 2-((3-((3-(trifluoromethyl)-phenyl)ethynyl)imidazo[1,2-a]pyridin-2-yl)methoxy)benzoate were dissolved in 4 ml of tetrahydrofurane with magnetic stirring, the mixture was cooled to 0° C. and then 0.148 ml (0.492 mmol) of RED-Al were added. The mixture was stirred at 0° C. for 15 min before being diluted with 15 ml of ethyl acetate and poured into 20 ml of water. With intense stirring, 1 ml of a NaOH aqueous solution (32% by mass) was slowly added. After separation, the organic phase was washed with 2×10 ml of water. The aqueous phases were extracted with 2×5 ml of ethyl acetate. The combined organic phases were washed with 20 ml of a saturated NaCl aqueous solution and then dried on $Na_2SO_4$ which was then removed by filtration. The obtained filtrate was concentrated in vacuo. The crude residue was purified by trituration in 10 ml of diisopropyl ether. The solid was isolated by filtration and dried in vacuo. 0.091 g (yield=58%) of (2-((3-((3-(trifluoromethyl)phenyl)ethynyl)imidazo[1,2-a]pyridin-2-yl) methoxy)phenyl)methanol were obtained as a pale brown solid. LC-MS: m/z=425 (M+2H$^+$); UV purity at 254 nm=94%. $^1$H NMR (300 MHz, DMSO) δ 8.77 (d, J=6.8 Hz, 1H), 8.05 (s, 1H), 7.92 (d, J=7.6 Hz, 1H), 7.73 (dt, J=14.3, 7.8 Hz, 3H), 7.55-7.43 (m, 1H), 7.38 (d, J=7.4 Hz, 1H), 7.20 (d, J=3.6 Hz, 3H), 7.03-6.86 (m, 1H), 5.39 (s, 2H), 4.98 (t, J=5.7 Hz, 1H), 4.55 (d, J=5.6 Hz, 2H).

Example 22

Preparation of Derivative Number 95: N-(2-(dimethylamino)ethyl)-2-((3-((4-fluorophenyl)ethynyl)imidazo[1,2-a]pyridin-2-yl)methoxy)benzamide Step 1: Preparation of 2-((3-((4-fluorophenyl) ethynyl)imidazo-[1,2-a]pyridin-2-yl)methoxy)benzoyl chloride

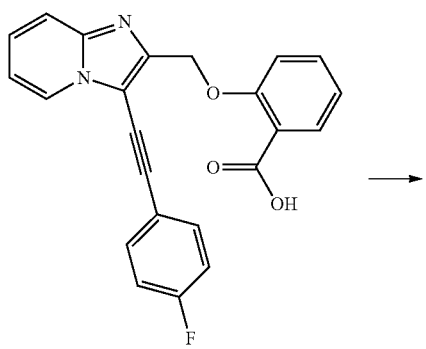

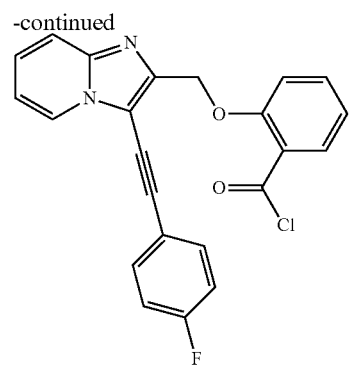

0.6 g (1.553 mmol) of 2-((3-((4-fluorophenyl)ethynyl)imidazo[1,2-a]pyridin-2-yl)methoxy)-benzoic acid were suspended in 20 ml of dichloromethane with magnetic stirring, the mixture was placed in a bath at 0° C. and then 0.408 ml (4.66 mmol) of oxalyl chloride were added drop wise, finally a few drops of dimethylformamide were added. The cold bath was withdrawn and then the mixture was stirred at r.t. for 2 h. The reaction medium was concentrated in vacuo and immediately used in the next step.

Step 2: Preparation of N-(2-(dimethylamino)ethyl)-2-((3-((4-fluorophenyl)ethynyl)imidazo[1,2-a]pyridin-2-yl)methoxy)benzamide (Derivative No. 95)

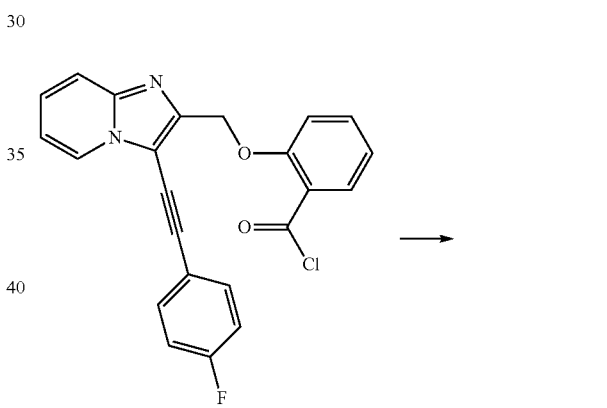

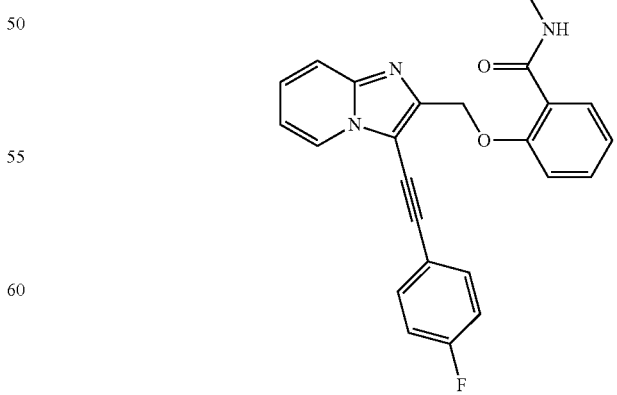

0.896 ml (7.76 mmol) of N,N-dimethylethane-1,2-diamine were solubilized in 8 ml of dichloromethane with magnetic stirring, 0.449 g (0.776 mmol) of 2-((3-((4-fluorophenyl)ethynyl)imidazo[1,2-a]pyridin-2-yl)methoxy)benzoyl chloride were added and the mixture was stirred at r.t. for 16 h before being concentrated in vacuo. The crude residue was purified by trituration in 20 ml of diisopropyl ether. The solid was isolated by filtration, washed with 10 ml of water and dried in vacuo. 0.178 g (yield=50%) of N-(2-(dimethylamino)ethyl)-2-((3-((4-fluorophenyl)ethynyl)imidazo[1,2-a]-pyridin-2-yl)methoxy)benzamide were obtained as a pale yellow solid. LC-MS: m/z=457 (MH$^+$); UV purity at 254 nm=98%. $^1$H NMR (300 MHz, DMSO) δ 8.68 (d, J=6.7 Hz, 1H), 8.47 (d, J=4.8 Hz, 1H), 7.91 (dd, J=7.7, 1.5 Hz, 1H), 7.72 (dd, J=8.6, 5.2 Hz, 3H), 7.57-7.39 (m, 3H), 7.32 (t, J=8.9 Hz, 2H), 7.17 (t, J=6.6 Hz, 1H), 7.09 (t, J=7.3 Hz, 1H), 5.51 (s, 2H), 2.5 (1H hidden under the solvent peak), 2.25 (t, J=6.5 Hz, 2H), 1.92 (s, 6H).

Derivative number 96 was prepared according to the same procedure.

| No. | Molecular weight g/mol | Aspect | LCMS purity UV at 254 nm | Mass spectrometry MH$^+$ | $^1$H NMR M-H$^+$ (300 MHz, DMSO) δ |
|---|---|---|---|---|---|
| 96 | 401.39 | solid | 97.5 | 402 | 10.97 (s, 1H), 9.12 (s, 1H), 8.66 (d, J = 6.8 Hz, 1H), 7.77 (dd, J = 8.8, 5.5 Hz, 2H), 7.70 (dd, J = 5.4, 3.5 Hz, 2H), 7.55-7.26 (m, 5H), 7.16 (t, J = 6.4 Hz, 1H), 7.06 (t, J = 6.9 Hz, 1H), 5.52 (s, 2H). |

Example 23

Preparation of Derivative No. 97: N-(3-((3-(phenyl ethynyl)imidazo[1,2-a]pyridin-2-yl)methoxy)phenyl) methane sulfonamide Step 1: Preparation of 2-(chloromethyl)-3-(phenylethynyl)imidazo[1,2-a]pyridine

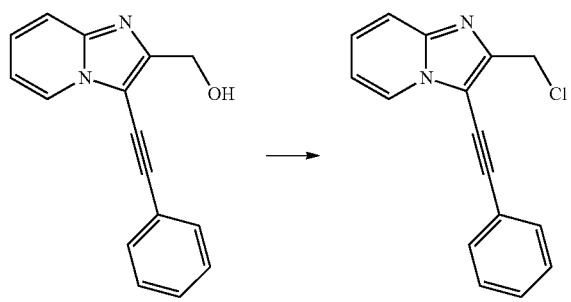 [SMILES: OCc1nc2ccccn2c1C#Cc1ccccc1 ; ClCc1nc2ccccn2c1C#Cc1ccccc1]

0.238 g (0.949 mmol) of (3-(phenyl-ethynyl)imidazo[1,2-a]pyridin-2-yl) methanol were dissolved in 5 ml of dichloromethane with magnetic stirring and then 0.346 ml (4.75 mmol) of thionyl chloride were added. The mixture was stirred at r.t. for 2 h before being concentrated in vacuo. The residue was taken up into 20 ml of a mixture consisting of ethyl acetate and of a saturated NaHCO$_3$ aqueous solution (1/1, v/v). After separation, the aqueous phase was extracted with 10 ml of ethyl acetate. The combined organic phases were washed with 10 ml of a saturated NaCl aqueous solution and then dried on Na$_2$SO$_4$ which was then removed by filtration. The obtained filtrate was concentrated in vacuo. 0.246 g (yield=96%) of 2-(chloromethyl)-3-(phenyl ethynyl)imidazo [1,2-a]pyridine were obtained as a brown solid. LC-MS: m/z=267 (MH$^+$); UV purity at 254 nm=98%.

Step 2: Preparation of N-(3-hydroxyphenyl) methanesulfonamide

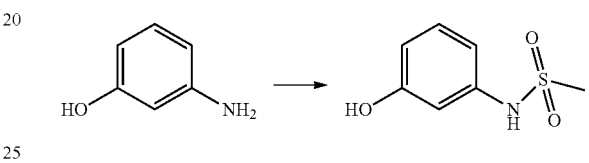

2 g (18.33 mmol) of 3-aminophenol were dissolved in 6 ml of pyridine with magnetic stirring, the mixture was cooled to 10° C. and then 1.8 ml (23.26 mmol) of methanesulfonyl chloride were added. The cold bath was withdrawn and the mixture was stirred at r.t. for 18 h before being diluted with 100 ml of a saturated NaCl aqueous solution. The aqueous phase was extracted with 100 ml of ethyl acetate. The organic phase was washed with 50 ml of a saturated NaHCO$_3$ aqueous solution, extracted with 50 ml of an aqueous solution of NaOH (0.5 N). The basic aqueous phase was washed with 2×100 ml of ethyl acetate and then acidified down to pH 2-3 by adding a 1N HCl aqueous solution. The acidified aqueous phase was extracted with 2×100 ml of ethyl acetate. The combined organic phases were washed with 100 ml of a saturated NaCl aqueous solution and then dried on Na$_2$SO$_4$ which was then removed by filtration. The obtained filtrate was concentrated in vacuo. 3.3 g (yield=80%) of N-(3-hydroxyphenyl)methanesulfonamide were obtained as an oil. LC-MS: m/z=186 (M-H$^+$); UV purity at 254 nm=81%.

Step 3: Preparation of N-(3-((3-(phenylethynyl)imidazo[1,2-a]pyridin-2-yl)methoxy)phenyl)methanesulfonamide (Derivative Number 97)

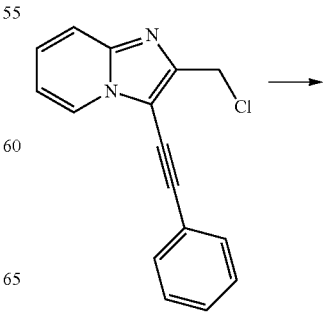

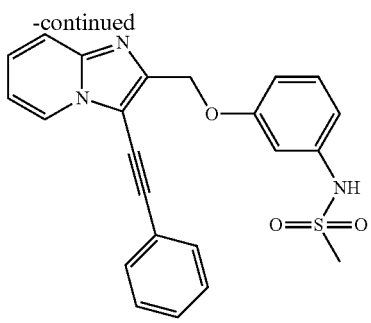

0.094 g (0.352 mmol) of 2-(chloromethyl)-3-(phenylethynyl)imidazo[1,2-a]pyridine were dissolved in 2 ml of dimethylformamide with magnetic stirring, 121 mg (0.529 mmol) of N-(3-hydroxyphenyl)methanesulfonamide and 0.172 g (0.529 mmol) of cesium carbonate were added. The mixture was stirred at 60° C. for 3 h before being poured onto 15 ml of a saturated NaCl aqueous solution. The aqueous phase was extracted with 2×20 ml of ethyl acetate. The combined organic phases were dried on Na$_2$SO$_4$ which was then removed by filtration. The obtained filtrate was concentrated in vacuo. The crude residue was purified by preparative HPLC and 0.028 g (yield=18%) of N-(3-((3-(phenylethynyl)imidazo[1,2-a]pyridin-2-yl)-methoxy)phenyl)methane sulfonamide were obtained as a white solid. LC-MS: m/z=418 (MH$^+$); UV purity at 254 nm=95%. $^1$H NMR (300 MHz, DMSO) δ 9.53 (s, 1H), 8.55 (d, J=6.8 Hz, 1H), 7.76-7.57 (m, 3H), 7.54-7.33 (m, 4H), 7.17-7.02 (m, 2H), 6.89 (dd, J=8.0, 1.1 Hz, 1H), 6.79 (t, J=2.1 Hz, 1H), 6.69-6.54 (m, 1H), 5.07 (s, 2H), 3.14 (s, 3H).

Example 24

Preparation of Derivative No. 111: ethyl 2-((6-chloro-3-((3-(trifluoromethyl)phenyl)ethynyl)imidazo[1,2-a]pyridin-2-yl)methylthio)acetate Step 1: Preparation of ethyl 2-((6-chloroimidazo[1,2-a]pyridin-2-yl)methylthio)acetate

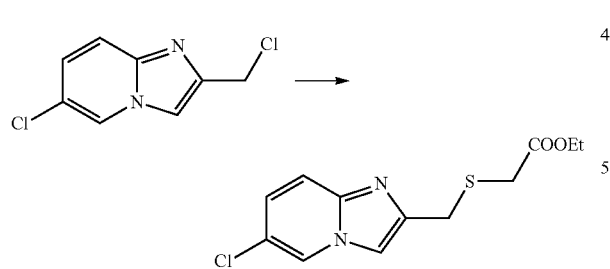

20 g (99 mmol) of 6-chloro-2-(chloromethyl)imidazo[1,2-a]pyridine, 0.746 g (4.97 mmol) of sodium iodide and 64.8 g (199 mmol) of cesium carbonate were loaded in 500 ml of acetonitrile. The solution was stirred at room temperature (r.t.) for 3 hours. The precipitated mineral was filtered and the solvent evaporated in vacuo. The obtained brown solid was dissolved in 300 ml of ethyl acetate, washed with 3×100 ml of water and directly purified on a silica cake, by eluting with ethyl acetate. 28.74 g (yield=100%) of ethyl 2-((6-chloroimidazo[1,2-a]pyridin-2-yl)methylthio)acetate were obtained as an orangey solid. LC-MS: m/z=285 (MH$^+$) UV purity at 254 nm=99%. $^1$H NMR (300 MHz, DMSO) δ 8.79 (dd, J=2.1, 0.8 Hz, 1H), 7.82 (s, 1H), 7.52 (d, J=9.6 Hz, 1H), 7.25 (dd, J=9.6, 2.1 Hz, 1H), 4.06 (q, J=7.1 Hz, 2H), 3.90 (s, 2H), 3.36 (s, 2H), 1.16 (t, J=7.1 Hz, 3H).

Step 2: Preparation of 3-iodo-2-(iodomethyl)imidazo[1,2-a]pyridine

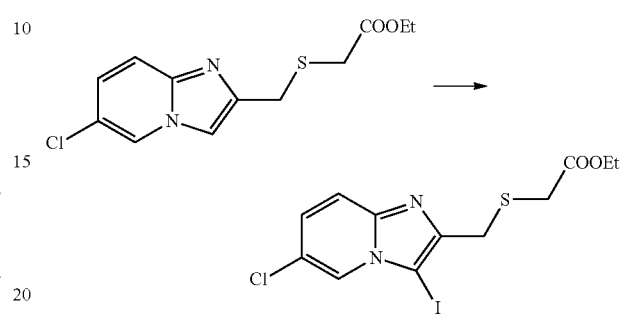

24.5 g (86 mmol) of ethyl 2-((6-chloroimidazo[1,2-a]pyridin-2-yl)methylthio) acetate were added to 400 ml of acetonitrile followed by the addition of 20.32 g (90 mmol) of N-iodosuccinimide. The solvent was stirred at r.t. for 1 h. The solvent was evaporated in vacuo, and the obtained residue was strongly stirred in 250 ml of water and 200 ml of diisopropyl ether. The precipitated solid was filtered and washed with 2×30 ml of water and 2×30 ml of diisopropyl ether. 33.93 g (yield=88%) of 3-iodo-2-(iodomethyl)imidazo[1,2-a]pyridine were obtained as a brown solid. LC-MS: m/z=411 (MH$^+$) UV purity at 254 nm=91.3%. $^1$H NMR 300 MHz, DMSO) δ 8.40 (dd, J=1.9, 0.7 Hz, 1H), 7.61 (dd, J=9.5, 0.6 Hz, 1H), 7.38 (dd, J=9.5, 2.0 Hz, 1H), 4.07 (q, J=7.1 Hz, 2H), 3.92 (s, 2H), 3.39 (s, 2H), 1.18 (t, J=7.1 Hz, 3H).

Step 3: Preparation of ethyl 2-((6-chloro-3-((3-(trifluoromethyl)phenyl)ethynyl)imidazo[1,2-a]pyridin-2-yl)methylthio)acetate

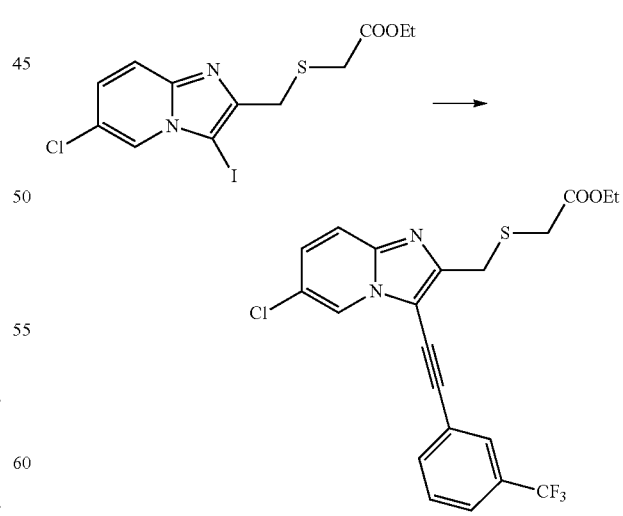

In an argon atmosphere, 27 g (59.8 mmol) of ethyl 2-((6-chloro-3-iodoimidazo[1,2-a]-pyridin-2-yl)methylthio)acetate, 9.51 ml (65.8 mmol) of 1-ethynyl-3-(trifluoromethyl)benzene, 1.139 g (5.98 mmol) of copper iodide and 125 ml (897 mmol) of triethylamine are loaded in 100 ml of DMF. Argon was bubbled in the solution for 10 min, and then 2.74 g (2.99 mmol) of $Pd_2(dba)_3$ were added. The mixture was stirred for 1 h at r.t. The catalyst was filtered on folded paper, the solution was poured onto 300 ml of water, extracted with 2×200 ml of ethyl acetate, the collected organic phases were washed with 3×150 ml of water and once with 150 ml of brine, dried on $Na_2SO_4$ which was then removed by filtration and the obtained filtrate was concentrated in vacuo. The residue was purified on a silica cake, and eluted with a heptane/ethyl acetate mixture. 23.21 g (yield=85%) of ethyl 2-((6-chloro-3-((3-(trifluoromethyl)phenyl)ethynyl)-imidazo[1,2-a]pyridin-2-yl)methylthio)acetate were obtained as a yellow solid. LC-MS: m/z=453 ($MH^+$) UV purity at 254 nm=99%. $^1$H NMR (300 MHz, DMSO) δ 8.91 (dd, J=1.9, 0.6 Hz, 1H), 8.14 (s, 1H), 8.01 (d, J=7.6 Hz, 1H), 7.71 (ddd, J=14.3, 9.4, 4.3 Hz, 3H), 7.47 (dd, J=9.5, 2.0 Hz, 1H), 4.18-3.93 (m, 4H), 3.46 (s, 2H), 1.11 (t, J=7.1 Hz, 3H).

Derivatives 108 to 110 and 112 to 114 were prepared according to the same procedure

| No. | Molecular weight g/mol | Aspect | LCMS purity UV at 254 nm | Mass spectrometry $MH^+$ $M-H^+$ | $^1$H NMR (300 MHz, DMSO) δ |
|---|---|---|---|---|---|
| 108 | 418.43 | brown solid | 99 | 419 | 8.72 (d, J = 6.7 Hz, 1H), 8.11 (s, 1H), 7.97 (d, J = 7.5 Hz, 1H), 7.86-7.60 (m, 3H), 7.52-7.37 (m, 1H), 7.13 (td, J = 6.8, 1.0 Hz, 1H), 4.09 (s, 2H), 4.03 (q, J = 7.1 Hz, 2H), 3.47 (s, 2H), 1.11 (t, J = 7.1 Hz, 3H). |
| 109 | 434.43 | brown oil | 99 | 435 | 8.68 (d, J = 6.7 Hz, 1H), 7.77-7.56 (m, 4H), 7.45 (d, J = 1.0 Hz, 2H), 7.13 (t, J = 6.6 Hz, 1H), 4.09-3.98 (m, 4H), 3.46 (s, 2H), 1.11 (t, J = 7.1 Hz, 3H). |
| 110 | 402.87 | orange solid | 92 | 403 | 8.82 (d, J = 1.2 Hz, 1H), 7.80 (dd, J = 8.6, 5.6 Hz, 2H), 7.69 (d, J = 9.5 Hz, 1H), 7.47 (dd, J = 9.5, 1.9 Hz, 1H), 7.34 (t, J = 8.9 Hz, 2H), 4.02 (dd, J = 12.9, 5.8 Hz, 4H), 3.45 (s, 2H), 1.11 (t, J = 7.1 Hz, 3H). |
| 112 | 468.88 | yellow solid | 99 | 469.1 | 8.93 (d, J = 1.3 Hz, 1H), 7.84 (s, 1H), 7.78 (d, J = 7.8 Hz, 1H), 7.72 (d, J = 9.5 Hz, 1H), 7.62 (t, J = 8.0 Hz, 1H), 7.49 (td, J = 9.5, 1.6 Hz, 2H), 4.09 (s, 2H), 4.04 (q, J = 7.1 Hz, 2H), 3.47 (s, 2H), 1.12 (t, J = 7.1 Hz, 3H) |
| 113 | 447.47 | brown oil | 96.2 | 448.1 | 8.74 (d, J = 6.7 Hz, 1H), 8.13 (s, 1H), 7.99 (d, J = 7.7 Hz, 1H), 7.79 (d, J = 8.0 Hz, 1H), 7.69 (dd, J = 15.5, 8.1 Hz, 2H), 7.49-7.41 (m, 1H), 7.14 (t, J = 6.8 Hz, 1H), 4.01 (p, J = 7.3 Hz, 4H), 3.61 (t, J = 6.3 Hz, 2H), 2.84 (t, J = 6.8 Hz, 2H), 1.19-0.98 (m, 5H). |
| 114 | 448.46 | beige solid | 99 | 449.1 | 8.32 (d, 1H), 8.11 (s, 1H), 7.98 (d, 1H), 7.77 (m, J = 21.6 Hz, 2H), 7.03 (t, 1H), 6.88 (d, 1H), 4.07 (s, 3H), 4.01 (q, J = 31.6 Hz, 2H), 3.96 (s, 2H), 3.46 (s, 2H), 1.11 (t, 3H). |

Example 25

Preparation of Derivative No. 118: 2-((6-chloro-3-((3-(trifluoromethyl)phenyl)ethynyl)imidazo[1,2-a]pyridin-2-yl)methylthio)acetic acid

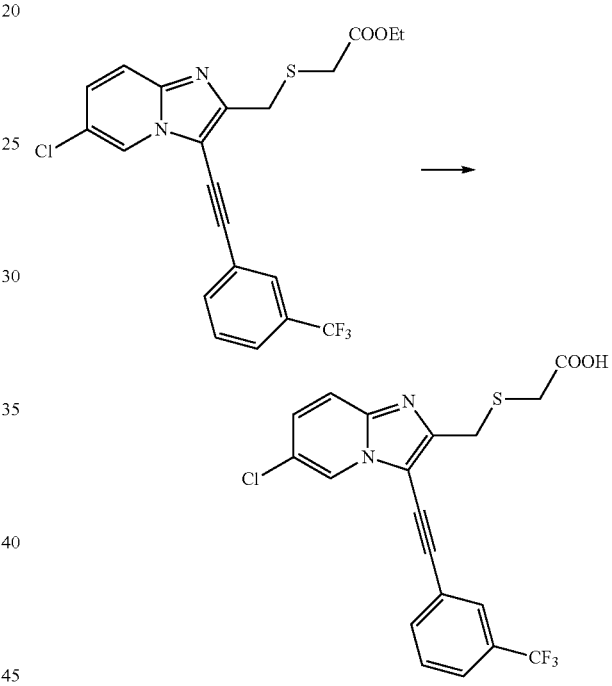

16 g (35.3 mmol) of ethyl 2-((6-chloro-3-((3-(trifluoromethyl)phenyl)ethynyl) imidazo[1,2-a]pyridin-2-yl)methylthio)acetate were added to 75 ml of ethanol and 75 ml of tetrahydrofurane before adding 4.24 ml (42.4 mmol) of a 32% sodium hydroxide aqueous solution. The mixture was stirred at r.t. for 2 h, and then 50 ml of water were added after 30 min for solubilising the precipitated solid. The solvent was evaporated in vacuo, the obtained residue was diluted in 250 ml of water and 50 ml of diisopropyl ether, and then the solution was brought to an acid pH by adding 2.53 ml (44.2 mmol) of acetic acid. The precipitated solid was filtered and then washed with water and diisopropyl ether. 12.45 g (yield=83%) of 2-((6-chloro-3-((3-(trifluoromethyl)phenyl)ethynyl)imidazo[1,2-a]pyridin-2-yl)methylthio)acetic acid was obtained as a yellow solid. LC-MS: m/z=425 ($MH^+$) UV purity at 254 nm=99%. $^1$H NMR (300 MHz, DMSO) δ 12.65 (s, 1H), 8.96 (s, 1H), 8.19 (s, 1H), 8.03 (d, J=7.6 Hz, 1H), 7.84-7.63 (m, 3H), 7.50 (dd, J=9.5, 1.8 Hz, 1H), 4.07 (s, 2H), 3.40 (s, 2H).

Derivatives 115 to 117, 119 and 120 were prepared according to the same procedure

| No. | Molecular weight g/mol | Aspect | LCMS purity UV at 254 nm | Mass spectrometry MH+ | M-H+ | 1H NMR (300 MHz, DMSO) δ |
|---|---|---|---|---|---|---|
| 115 | 390.38 | yellow solid | 99 | 391 | 389 | 8.73 (d, J = 6.7 Hz, 1H), 8.12 (s, 1H), 7.98 (d, J = 7.6 Hz, 1H), 7.85-7.59 (m, 3H), 7.52-7.40 (m, 1H), 7.13 (td, J = 6.8, 1.0 Hz, 1H), 4.20-3.98 (m, 2H), 3.40 (s, 2H). |
| 116 | 406.38 | Solid | 97 | 407 | 405 | 12.62 (s, 1H), 8.69 (d, J = 6.3 Hz, 1H), 7.86-7.52 (m, 4H), 7.45 (dd, J = 8.0, 7.0 Hz, 2H), 7.12 (dd, J = 14.8, 8.1 Hz, 1H), 4.07 (s, 2H), 3.40 (s, 2H). |
| 117 | 374.82 | orange solid | 99 | 375 | | 12.66 (s, 1H), 8.83 (s, 1H), 7.81 (dd, J = 7.6, 5.7 Hz, 2H), 7.70 (d, J = 9.5 Hz, 1H), 7.47 (d, J = 9.5 Hz, 1H), 7.33 (t, J = 8.6 Hz, 2H), 4.04 (s, 2H), 3.38 (s, 2H) |
| 119 | 440.82 | pale yellow solid | 97 | 441.1 | 439 | 12.64 (s, 1H), 8.92 (d, J = 1.2 Hz, 1H), 7.84 (s, 1H), 7.78 (d, J = 7.8 Hz, 1H), 7.71 (d, J = 9.5 Hz, 1H), 7.60 (t, J = 8.0 Hz, 1H), 7.54-7.37 (m, 2H), 4.07 (s, 2H), 3.39 (s, 2H) |
| 120 | 420.41 | Solid | 99 | 421.6 | 419.6 | 8.32 (d, 1H), 8.12 (s, 1H), 8.01 (d, 1H), 7.72 (m, 2H), 7.02 (t, 1H), 6.87 (d, 1H), 3.97 (s, 2H), 3.96 (s, 3H), 3.24 (s, 2H) |

Example 26

Preparation of Derivative No. 121: ethyl 2-((3-((3-(trifluoromethyl)phenyl)ethynyl)imidazo[1,2-a]pyridin-2-yl)methylsulfonyl)acetate

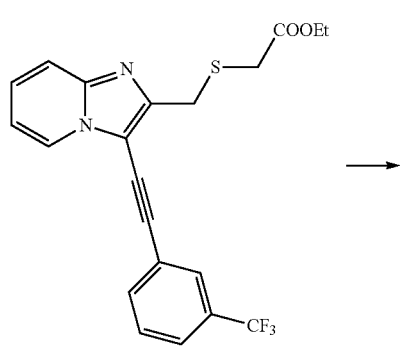

→

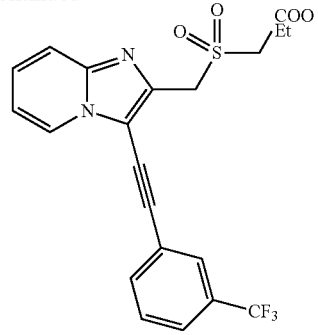

40 mg (0.096 mmol) of ethyl 2-((3-((3-(trifluoromethyl)phenyl)ethynyl)imidazo[1,2-a]-pyridin-2-yl)methylthio)acetate were solubilised in 1 ml of acetone followed by the addition of 8.03 mg (0.096 mmol) of sodium hydrogencarbonate. The solution was cooled to 0° C. before adding a solution of 118 mg (0.096 mmol) of oxone in 1 ml of water. The mixture was stirred at r.t. for 4 h. The solution was washed with 5 ml of water, and the obtained solid was filtered and washed with 5 ml of water and 2 ml of diisopropyl ether. 29 mg (yield=64%) of ethyl 2-((3-((3-(trifluoromethyl)phenyl)ethynyl) imidazo[1,2-a]pyridin-2-yl)methylsulfonyl)acetate were obtained as a pale yellow solid. LC-MS: m/z=451 (MH+) UV purity at 254 nm=94.6%. 1H NMR (300 MHz, DMSO) δ 8.80 (d, J=6.8 Hz, 1H), 8.17 (s, 1H), 8.03 (d, J=7.6 Hz, 1H), 7.76 (dt, J=13.6, 7.8 Hz, 3H), 7.62-7.45 (m, 1H), 7.21 (t, J=6.6 Hz, 1H), 4.98 (s, 2H), 4.62 (s, 2H), 4.19 (dd, J=14.1, 7.0 Hz, 2H), 1.21 (t, J=7.1 Hz, 3H).

The derivative 122 was prepared according to the same procedure

| No. | Molecular weight g/mol | Aspect | LCMS purity UV at 254 nm | Mass spectrometry MH+ | M-H+ | 1H NMR (300 MHz, DMSO) δ |
|---|---|---|---|---|---|---|
| 122 | 500.88 | grey solid | 99 | 501 | 499 | 9.01 (s, 1H), 7.82 (dd, J = 17.1, 9.6 Hz, 3H), 7.65-7.46 (m, 3H), 4.97 (s, 2H), 4.60 (s, 2H), 4.19 (q, J = 7.1 Hz, 2H), 1.21 (t, J = 7.1 Hz, 3H). |

Example 27

Preparation of Derivative No. 123: 2-((6-chloro-3-((3-(trifluoromethoxy)phenyl)ethynyl)imidazo[1,2-a]pyridin-2-yl)methylsulfonyl)acetic acid

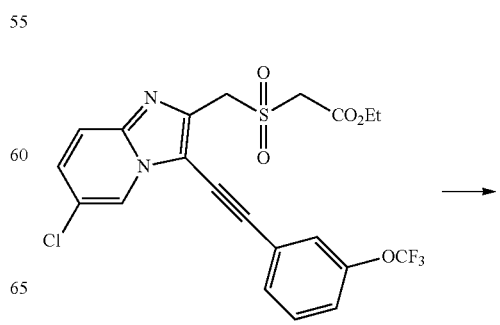

→

-continued

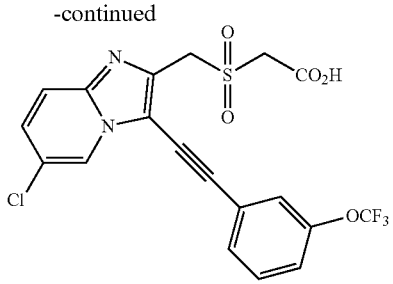

100 mg (0.200 mmol) of ethyl 2-((6-chloro-3-((3-(trifluoromethoxy)phenyl)-ethynyl)imidazo[1,2-a]pyridin-2-yl)methylsulfonyl)acetate were dissolved in 2 ml of ethanol before adding 0.060 ml (0.599 mmol) of a 32% sodium hydroxide aqueous solution. The mixture was stirred at r.t. for 16 h. The solution was poured into 10 ml of water, acidified to an acid pH with acetic acid, extracted with 2×5 ml of dichloromethane, the combined organic phases were dried on $Na_2SO_4$ which was then removed by filtration and the obtained filtrate was concentrated in vacuo. 76 mg (yield=80%) of 2-((6-chloro-3-((3-(trifluoromethoxy)phenyl)ethynyl)-imidazo[1,2-a]pyridin-2-yl)methylsulfonyl) acetic acid were obtained as a yellow solid. LC-MS: m/z=473 (MH$^+$) UV purity at 254 nm=99%. $^1$H NMR (300 MHz, DMSO) δ 14.72-12.20 (m, 1H), 9.00 (d, J=1.2 Hz, 1H), 7.88-7.76 (m, 3H), 7.62-7.45 (m, 3H), 4.96 (s, 2H), 4.42 (s, 2H).

Example 28

Preparation of Derivative No. 124: N-(pyridin-3-yl)-2-((3-((3-(trifluoromethyl)phenyl)ethynyl)imidazo[1,2-a]pyridin-2-yl)methylthio)acetamide

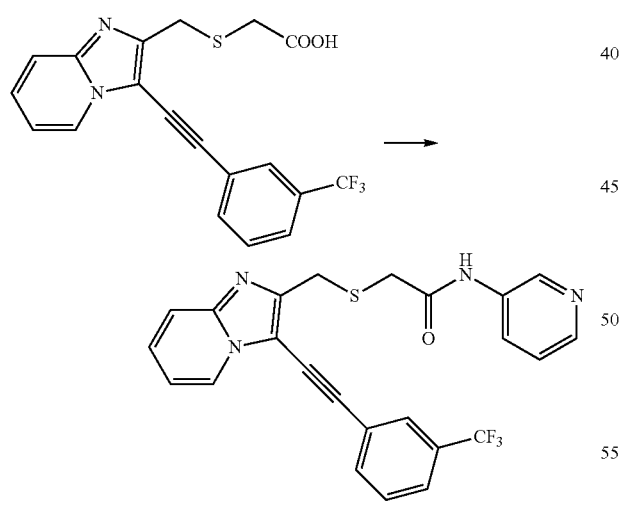

141 mg (0.358 mmol) of 2-((3-((3-(trifluoromethyl)phenyl)ethynyl)imidazo[1,2-a]-pyridin-2-yl)methylthio)acetic acid were dissolved in 5 ml of dichloromethane followed by the addition of 0.094 ml (1.073 mmol) of oxalyl chloride and a drop of DMF. The solvent was stirred at r.t. for 2 h and then the solvent was evaporated in vacuo. The obtained residue was taken up in 5 ml of tetrahydrofurane, 99 mg (0.715 mmol) of sodium carbonate were added followed by the addition of 40.4 mg (0.429 mmol) of 3-aminopyridine. The solution was stirred at r.t. for 16 h. The mixture was then poured onto 15 ml of water, extracted 3 times with 15 ml of ethyl acetate, the combined organic phases were washed with 20 ml of brine and then were dried on $Na_2SO_4$ which was then removed by filtration and the obtained filtrate was concentrated in vacuo. The crude residue was purified by flash chromatography on a silica gel cartridge (eluent: dichloromethane/methanol gradient, 100% to 90% of dichloromethane, v/v). 89 mg of N-(pyridin-3-yl)-2-((3-((3-(trifluoromethyl)-phenyl)-ethynyl)imidazo[1,2-a]pyridin-2-yl)methylthio) acetamide were obtained as a pale yellow solid. LC-MS: m/z=467 (MH$^+$) UV purity at 254 nm=95%. $^1$H NMR (300 MHz, DMSO) δ 10.13 (s, 1H), 8.76 (dd, J=16.4, 4.5 Hz, 2H), 8.24 (dd, J=4.7, 1.5 Hz, 1H), 8.07 (ddd, J=8.3, 2.5, 1.5 Hz, 1H), 7.79-7.60 (m, 3H), 7.60-7.35 (m, 3H), 7.30 (dd, J=8.3, 4.7 Hz, 1H), 7.16 (td, J=6.8, 1.1 Hz, 1H), 4.90 (s, 2H), 4.26 (s, 2H).

Derivatives 125 to 128 were prepared according to the same procedure

| No. | Molecular weight g/mol | Aspect | LCMS purity UV at 254 nm | Mass spectrometry MH$^+$ | M-H$^+$ | $^1$H NMR (300 MHz, DMSO) δ |
|---|---|---|---|---|---|---|
| 125 | 390.31 | pale yellow solid | 99 | 391 | 389 | 10.13 (s, 1H), 8.76 (dd, J = 16.4, 4.5 Hz, 2H), 8.24 (dd, J = 4.7, 1.5 Hz, 1H), 8.07 (ddd, J = 8.3, 2.5, 1.5 Hz, 1H), 7.79-7.60 (m, 3H), 7.60-7.35 (m, 3H), 7.30 (dd, J = 8.3, 4.7 Hz, 1H), 7.16 (td, J = 6.8, 1.1 Hz, 1H), 4.90 (s, 2H), 4.26 (s, 2H). |
| 126 | 482.48 | yellow solid | 99 | 483 | 481 | 10.30 (s, 1H), 8.73-8.59 (m, 2H), 8.22 (dd, J = 4.7, 1.4 Hz, 1H), 8.00 (ddd, J = 8.3, 2.5, 1.5 Hz, 1H), 7.72-7.59 (m, 3H), 7.56-7.37 (m, 3H), 7.26 (dd, J = 8.3, 4.7 Hz, 1H), 7.12 (td, J = 6.8, 1.1 Hz, 1H), 4.13 (s, 2H), 3.46 (s, 2H). |
| 127 | 451.89 | Solid | 98 | 452 | | 8.96 (s, 1H), 8.20 (s, 1H), 8.05 (d, J = 7.6 Hz, 1H), 7.97 (s, 1H), 7.79 (d, J = 7.8 Hz, 1H), 7.71 (d, J = 9.7 Hz, 2H), 7.50 (d, J = 11.4 Hz, 1H), 4.10 (s, 2H), 3.20 (s, 2H), 3.05 (dt, J = 14.2, 7.2 Hz, 2H), 0.96 (t, J = 7.2 Hz, 3H). |
| 128 | 467.89 | Solid | 97 | 468 | | 8.92 (s, 1H), 7.97 (s, 1H), 7.85 (s, 1H), 7.79 (d, J = 7.8 Hz, 1H), 7.71 (d, J = 9.5 Hz, 1H), 7.60 (t, J = 8.0 Hz, 1H), 7.54-7.40 (m, 2H), 4.09 (s, 2H), 3.20 (s, 2H), 3.11-2.99 (m, 2H), 0.96 (t, J = 7.2 Hz, 3H). |

Example 29

Preparation of Derivative No. 129: 4-hydroxy-3,3-dimethyl-2-((3-((3-(trifluoromethyl)phenyl)ethynyl)imidazo[1,2-a]pyridin-2-yl)methylthio)butanoic acid

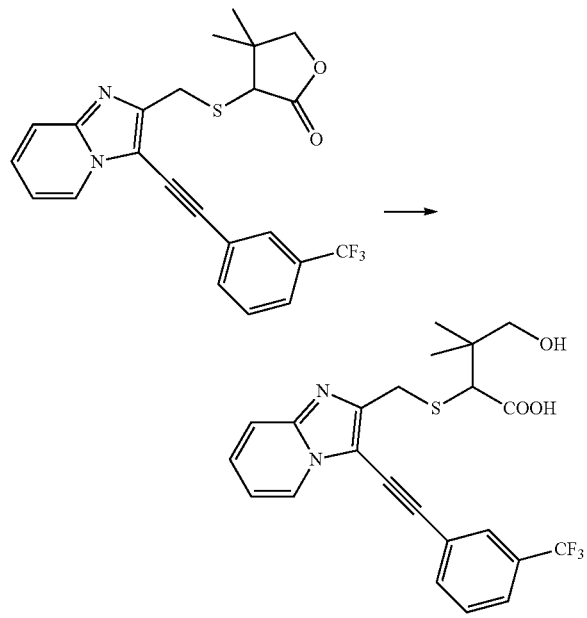

130 mg (0.303 mmol) of 4,4-dimethyl-3-((3-((3-(trifluoromethyl)phenyl)ethynyl) imidazo[1,2-a]pyridin-2-yl)methylthio)dihydrofuran-2(3H)-one were dissolved in 2 ml of methanol and 2 ml of tetrahydrofurane followed by the addition of 0.334 ml (0.334 mmol) of a 1N sodium hydroxide aqueous solution. The solution was stirred for 16 h. It was acidified down to an acid pH with acetic acid, and diluted with water until precipitation of a solid, which was then filtered and washed with water. 115 mg of 4-hydroxy-3,3-dimethyl-2-((3-((3-(trifluoromethyl)phenyl)-ethynyl)imidazo[1,2-a]pyridin-2-yl)methylthio) butanoic acid were obtained as a pale brown solid. LC-MS: m/z=447 (MH+) UV purity at 254 nm=99%. $^1$H NMR (300 MHz, DMSO) δ 12.69 (s, 1H), 8.77 (d, J=6.7 Hz, 1H), 8.11 (s, 1H), 7.97 (d, J=7.5 Hz, 1H), 7.79 (d, J=7.7 Hz, 1H), 7.70 (t, J=8.2 Hz, 2H), 7.54-7.41 (m, 1H), 7.16 (t, J=6.6 Hz, 1H), 4.81 (d, J=12.3 Hz, 1H), 4.70 (sl, 1H), 4.58 (d, J=12.3 Hz, 1H), 3.92 (s, 1H), 3.40 (s, 1H), 3.10 (d, J=10.4 Hz, 1H), 0.86 (s, 3H), 0.82 (s, 3H)

Example 30

Preparation of Derivative No. 130: 2-((3-((3-(trifluoromethyl)phenyl)ethynyl)imidazo[1,2-a]pyridin-2-yl)methylthio)ethanol

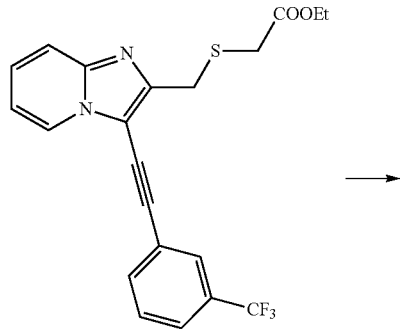

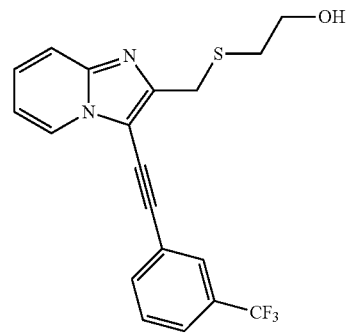

Under an argon atmosphere, 200 mg (0.446 mmol) of ethyl 2-((3-((3-(trifluoromethyl)phenyl)ethynyl)imidazo[1,2-a]pyridin-2-yl)methylthio)-acetate were dissolved in 4 ml of tetrahydrofurane and 33.9 mg (0.892 mmol) of LiAlH$_4$ were added. The solution was heated to 50° C. for 1 h. 0.030 ml of water were slowly added, followed by the addition of 0.030 ml of 6N sodium hydroxide and then with 0.1 ml of water. After 30 min of stirring, the precipitate was filtered, and washed with ethyl acetate. The collected organic phases were washed with brine and then dried on Na$_2$SO$_4$ which was then removed by filtration and the obtained filtrate was concentrated in vacuo. The obtained solid was triturated in ethyl acetate, filtered and then washed with ethyl acetate. 50 mg (yield=28%) of 2-((3-((3-(trifluoromethyl)phenyl)ethynyl) imidazo[1,2-a]pyridin-2-yl)-methylthio) ethanol were obtained as a white solid. LC-MS: m/z=407 (MH+) UV purity at 254 nm=89%. $^1$H NMR (300 MHz, DMSO) δ 8.30 (d, 1H), 8.12 (s, 1H), 7.99 (m, 1H), 7.75 (m, 2H), 7.03 (m, 1H), 6.88 (d, 1H), 4.84 (t, 1H), 3.96 (s, 5H), 3.60 (m, 2H), 2.67 (t, 2H).

The derivative 131 was prepared according to the same procedure:

| No. | Molecular weight g/mol | Aspect | LCMS purity UV at 254 nm | Mass spectrometry MH+ | M-H+ | $^1$H NMR (300 MHz, DMSO) δ |
|---|---|---|---|---|---|---|
| 131 | 410.84 | beige solid | 99 | 410.9 | | 8.95 (s, 1H), 8.18 (s, 1H), 8.04 (d, 1H), 7.76 (m, 3H), 7.50 (d, 1H), 4.84 (t, 1H), 3.98 (s, 1H), 3.59 (q, 2H), 2.67 (t, 2H). |

Example 31

Preparation of Derivative No. 132: N—(N-(tert-butoxycarbonyl)carbamimidoyl)-2-((3-((4-fluorophenyl)ethynyl) imidazo[1,2-a]pyridin-2-yl)methoxy)acetamide

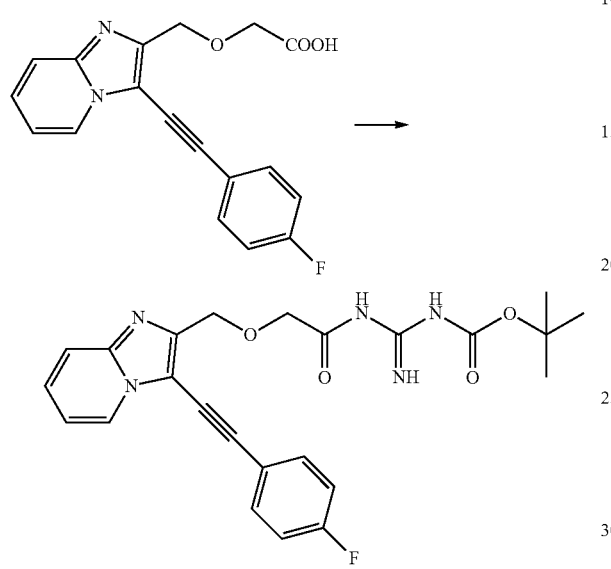

200 mg of 2-((3-((4-fluorophenyl)ethynyl)imidazo[1,2-a]pyridin-2-yl)methoxy)acetic acid, 200 mg (0.617 mmol) of PyBOP and 118 mg (0.740 mmol) of guanidine-BOC were loaded with 2 ml of DMF. 0.258 ml (1.850 mmol) of triethylamine was then poured and the reaction was stirred at r.t. for 4 h. The mixture was poured into 10 ml of water and 5 ml of heptane with stirring. The obtained solid was filtered and then washed with 2 ml of water and 1 ml of heptane. 220 mg (yield=77%) of N—(N-(tert-butoxycarbonyl)carbamimidoyl)-2-((3-((4-fluorophenyl)ethynyl)imidazo[1,2-a]pyridin-2-yl)methoxy)acetamide were obtained as a grey solid. LC-MS: m/z=466 (MH$^+$) UV purity at 254 nm=99%. $^1$H NMR (300 MHz, DMSO) δ 11.10 (s, 1H), 8.71 (t, J=37.0 Hz, 3H), 7.86-7.62 (m, 3H), 7.51-7.37 (m, 1H), 7.30 (t, J=8.9 Hz, 2H), 7.13 (dd, J=6.7, 6.0 Hz, 1H), 4.81 (s, 2H), 4.18 (s, 2H), 1.38 (s, 9H).

Derivative 133 was prepared according to the same procedure

| No. | Molecular weight g/mol | Aspect | LCMS purity UV at 254 nm | Mass spectrometry MH$^+$ M-H$^+$ | | $^1$H NMR (300 MHz, DMSO) δ |
|---|---|---|---|---|---|---|
| 133 | 531.55 | yellow solid | 99 | 532.2 | 530.2 | 10.98 (s, 1H), 8.78 (t, J = 25.6 Hz, 3H), 8.10 (s, 1H), 7.93 (d, J = 7.6 Hz, 1H), 7.71 (dt, J = 17.7, 8.3 Hz, 3H), 7.52-7.38 (m, 1H), 7.13 (td, J = 6.8, 1.0 Hz, 1H), 4.10 (s, 2H), 3.43 (s, 2H), 1.38 (s, 9H). |

Example 32

Preparation of Derivative No. 134: N-carbamimidoyl-2-((3-((4-fluorophenyl)ethynyl)imidazo[1,2-a]pyridin-2-yl)-methoxy)acetamide hydrochloride

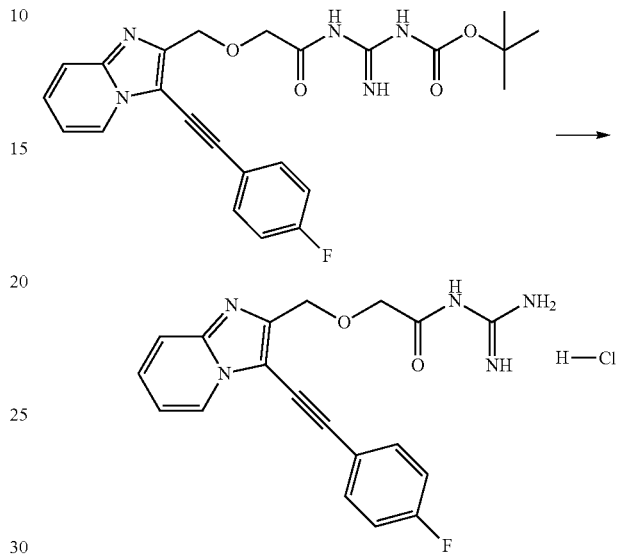

190 mg (0.408 mmol) of N—(N-(tert-butoxycarbonyl)carbamimidoyl)-2-((3-((4-fluorophenyl)ethynyl)imidazo[1,2-a]pyridin-2-yl)methoxy)acetamide were dissolved in 2 ml of ethanol before adding 1.020 ml (4.08 mmol) of a 4N hydrochloric acid solution in dioxane. The solution was heated to 60° C. for 2 h. The solvent was evaporated in vacuo. By cooling, the crystallised solid was filtered and washed with ethanol. 85 mg (yield=52%) of N-carbamimidoyl-2-((3-((4-fluorophenyl)ethynyl)imidazo[1,2-a]pyridin-2-yl) methoxy)acetamide hydrochloride were obtained as a yellow solid. LC-MS: m/z=366 (MH$^+$) UV purity at 254 nm=99%. $^1$H NMR (300 MHz, DMSO) δ 11.36 (s, 1H), 8.86 (d, J=6.7 Hz, 1H), 8.55 (d, J=28.4 Hz, 4H), 7.92-7.71 (m, 4H), 7.44-7.31 (m, 3H), 4.99 (s, 2H), 4.40 (s, 2H).

The derivative 135 was prepared according to the same procedure:

| No. | Molecular weight g/mol | Aspect | LCMS purity UV at 254 nm | Mass spectrometry MH$^+$ M-H$^+$ | | $^1$H NMR (300 MHz, DMSO) δ |
|---|---|---|---|---|---|---|
| 135 | 467.90 | Pale grey solid | 99 | 432.1 | | 11.80 (s, 1H), 8.81 (d, J = 6.7 Hz, 1H), 8.62-8.05 (m, 5H), 8.00 (d, J = 7.7 Hz, 1H), 7.81 (d, J = 7.9 Hz, 1H), 7.72 (dd, J = 12.8, 4.9 Hz, 2H), 7.63-7.52 (m, 1H), 7.24 (t, J = 6.5 Hz, 1H), 4.16 (s, 2H), 3.61 (s, 2H). |

Example 33

Preparation of Derivative No. 138: 2-((pyridin-2-ylthio)methyl)-3-((3-(trifluoromethyl)phenyl)ethynyl)imidazo[1,2-a]pyridine

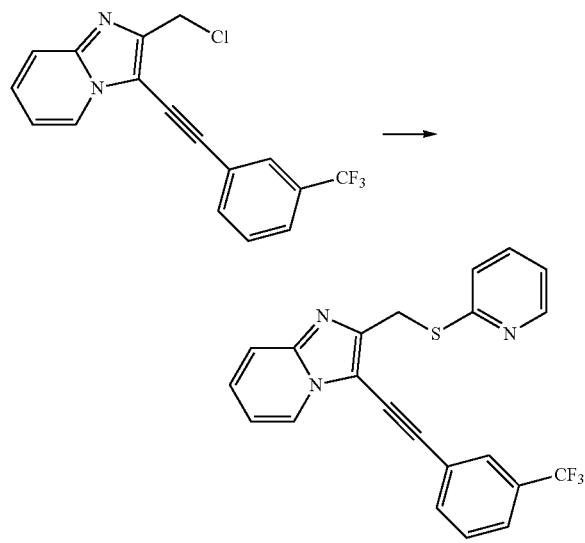

150 mg (0.421 mmol) of 2-(chloromethyl)-3-((3-(trifluoromethyl)phenyl)ethynyl)imidazo[1,2-a]pyridine were dissolved in 5 ml of acetonitrile followed by the addition of 96 mg (0.842 mmol) of pyridine-2-thiol and 274 mg (0.842 mmol) of cesium carbonate. The solvent was stirred at r.t. for 2 h 30 min. The mixture was then poured into 40 ml of water, and then extracted 3 times with 15 ml of ethyl acetate. The collected organic phases were washed with 30 ml of a saturated sodium hydrogencarbonate solution, with 30 ml of brine and then were dried on $Na_2SO_4$ which was then removed by filtration and the obtained filtrate was concentrated in vacuo. The crude residue was purified by flash chromatography on a silica gel cartridge (eluent: heptane/ethyl acetate gradient, 80% to 70% of heptane, v/v). 129 mg (yield=74%) of 2-((pyridin-2-ylthio)methyl)-3-((3-(trifluoromethyl)phenyl)ethynyl)imidazo-[1,2-a]pyridine were obtained as a beige solid. LC-MS: m/z=410 (MH$^+$) UV purity at 254 nm=99%. $^1$H NMR (300 MHz, DMSO) δ 8.70 (d, J=6.7 Hz, 1H), 8.52-8.37 (m, 1H), 8.02 (s, 1H), 7.91 (d, J=7.6 Hz, 1H), 7.71 (dd, J=41.7, 4.5 Hz, 4H), 7.43 (s, 2H), 7.13 (d, J=1.1 Hz, 2H), 4.73 (s, 2H).

Derivatives 136 and 137 were prepared according to the same procedure:

| No. | Molecular weight g/mol | Aspect | LCMS purity UV at 254 nm | Mass spectrometry m/z MH$^+$ | M-H$^+$ | $^1$H NMR (300 MHz, DMSO) δ |
|---|---|---|---|---|---|---|
| 136 | 417.47 | pale brown solid | 94 | 417.9 | | 8.72 (d, J = 6.8 Hz, 1H), 8.10 (s, 1H), 7.97 (d, J = 7.6 Hz, 1H), 7.80 (d, J = 7.9 Hz, 1H), 7.76-7.64 (m, 2H), 7.51-7.42 (m, 1H), 7.15 (td, J = 6.8, 1.1 Hz, 1H), 4.69 (s, 2H), 4.16 (t, J = 8.0 Hz, 2H), 3.46 (t, J = 8.0 Hz, 2H). |
| 137 | 412.43 | beige solid | 99 | 413.1 | | 8.77 (d, J = 6.7 Hz, 1H), 8.04 (s, 1H), 7.90 (d, J = 7.6 Hz, 1H), 7.73 (dt, J = 7.4, 6.3 Hz, 3H), 7.48 (dd, J = 13.5, 5.9 Hz, 2H), 7.21-7.07 (m, 2H), 6.99 (dd, J = 4.9, 3.5 Hz, 1H), 4.78 (d, J = 12.3 Hz, 4H). |

Stimulation Test of Insulin Secretion by INS-1 Cells

The different compounds were tested on an INS-1 beta-pancreatic line in order to evaluate their capability of potentializing the insulin secretion in response to glucose. Very briefly, the cells are cultivated in a culture medium, RPMI 1640 with 10 mM glucose containing 1 mM of sodium pyruvate, 50 µM of 2-mercaptoethanol, 2 mM of glutamine, 10 mM of HEPES, 100 IU/ml of penicillin, 100 µg/ml of streptomycin and 10% of inactivated fetal calf serum, as described by Asfari et al. [9]. For the insulin secretion test, the INS-1 cells are sown and cultivated in 96-well plates. After 3 days of cultivation at 37° C. in a humid atmosphere (95% air/5% $CO_2$), the medium is removed and the cells are incubated for 16 h in a medium containing 5 mM of glucose and 1% of inactivated fetal calf serum. On the day of the test, the cells are washed with a Krebs buffer (pH 7.4) containing 0.1% of bovine albumin and then pre-incubated for 30 min at 37° C. in this same buffer containing 2.8 mM of glucose. Finally, the cells are again washed with Krebs buffer and then incubated for 1 h in the buffer of the secretion test (Krebs, pH 7.4 containing 0.1% of bovine albumin and 3.5 mM of glucose and molecules to be evaluated). At the end of the test, the cell supernatant is recovered in order to measure therein the secreted insulin, by means of an ELISA kit using a rat anti-insulin antibody (ELISA Alpco Cat no. 80-INSRTH-E10). Each condition is tested in triplicate. The 3.5 mM glucose, the $10^{-7}$M GLP-1 and the Forskoline $10^{-7}$/IBMX $10^{-5}$M mixtures are used as positive controls of the test. A compound stimulates the secretion of insulin if this factor is greater than or equal to 130% of the control for a given glucose dose.

| No. of derivative | HGP % of ctrl @ 50 µM | HGP % of ctrl @ 10 µM |
|---|---|---|
| 1 | 211 | 121 |
| 2 | 333 | 127 |
| 3 | 472 | 130 |
| 5 | 195 | 180 |
| 9 | 175 | 116 |
| 12 | 204 | 123 |
| 14 | 242 | 100 |
| 25 | 226 | 134 |
| 26 | 246 | 138 |
| 39 | 137 | 121 |
| 54 | | 203 |
| 55 | 135 | 130 |
| 58 | 233 | 127 |
| 59 | 220 | 134 |
| 72 | 151 | 172 |
| 76 | 202 | 156 |
| 78 | 152 | 197 |

-continued

| No. of derivative | HGP % of ctrl @ 50 μM | HGP % of ctrl @ 10 μM |
|---|---|---|
| 79 | 152 | 128 |
| 81 | 134 | 142 |
| 87 | 167 | 182 |
| 88 | 263 | 138 |
| 92 | 211 | 135 |
| 101 | 111 | 163 |
| 102 | 107 | 176 |
| 110 | 140 | 162 |
| 111 | 173 | 136 |
| 112 | 256 | 150 |
| 113 | 112 | 136 |
| 117 | 137 | 130 |
| 129 | 146 | 109 |
| 130 | 114 | 150 |
| 131 |  | 131 |
| 135 |  | 131 |

The tested derivatives of formula I therefore have a significant effect on the potentialization of insulin secretion in response to glucose by the INS-1•pancreatic cells. The values are comprised between 131% and more than 450% of activation regardless of the relevant dose.

Study of the Effect on Hepatic Production of Glucose

Equipment and Method:

The hepatocytes are isolated from Wistar rat liver having fasted for 24 h after perfusion of collagenase in the portal vein. 1) The freshly isolated hepatocytes are sown in 6-well plates coated with collagen and containing an adhesion medium (Williams Medium). After adhesion, the medium is replaced with RPMI 1640 medium without any glucose, containing hydrocortisone ($7 \cdot 10^{-5}$M) for a duration from 16 to 18 h. The next day, the glucose hepatic production test is conducted in a Krebs medium for 3 h. The basal conditions are cells incubated with only Krebs, the stimulated conditions are the cells placed in Krebs+lactate+pyruvate, the produced conditions are the cells exposed to chemical compounds in a Krebs/lactate/pyruvate medium. In the case when the compounds are dissolved in DMSO, all the conditions of the tests are met in the presence of a final concentration of 0.1% DMSO. The positive control of the test is the mercaptopicolinate known for its inhibitory action on hepatic production of glucose via the phosphoenolpyruvate carboxykinase. For short term treatments, the compounds are incubated for 3 h. For long term treatments, the compounds are incubated for 20 h at the moment when the hepatocytes are cultivated in RPMI and then added during the hepatic production test for 3 h. At the end of the 3 hours of incubation, the supernatant is recovered for measurement of glucose with a colorimetric method using glucose oxidase. The cells are lysed with a 0.1% NaOH aqueous solution in order to measure the amount of protein with the Lowry method. The results are expressed in mmol of glucose per mg of protein. A compound inhibits hepatic production of glucose if this factor is less than or equal to 75% of the control.

3 h Incubation

| No. of derivative | HGP % of ctrl @ 100 μM | HGP % of ctrl @ 50 μM |
|---|---|---|
| 1 | 56 | 70 |
| 3 | 60 | 73 |
| 4 | 74 | 81 |
| 7 | 45 | 55 |
| 10 | 71 | 86 |
| 14 | 73 | 86 |
| 23 | 73 | 95 |
| 25 | 73 | 83 |
| 26 | 67 | 78 |
| 29 | 40 | 63 |
| 30 | 60 | 74 |
| 35 | 64 | 73 |
| 46 | 69 | 85 |
| 51 | 45 | 61 |
| 59 | 45 | 97 |
| 76 | 59 | 67 |
| 77 | 50 | 87 |
| 78 | 44 | 51 |
| 79 | 74 | 86 |
| 81 | 47 | 76 |
| 87 | 25 | 43 |
| 88 | 50 | 67 |
| 89 | 33 | 78 |
| 90 | 27 | 77 |
| 92 | 39 | 58 |
| 93 | 19 | 26 |
| 95 | 62 | 65 |
| 96 | 66 | 81 |
| 99 | 68 | 85 |
| 108 | 64 | 89 |
| 109 | 61 | 80 |
| 110 | 37 | 50 |
| 111 | 27 | 73 |
| 112 | 26 | 65 |
| 115 | 54 | 94 |
| 116 | 64 | 88 |
| 117 | 43 | 55 |
| 119 |  | 73 |
| 126 | 68 | 72 |

The tested derivatives of formula I have a significant effect on the inhibition of hepatic production of glucose. The strongest inhibitions are obtained with the derivatives 7, 78, 87, 92, 93, 110 and 117 with two doses and the derivatives 29, 51, 59, 76, 77, 81, 88, 89, 90, 111, 112 et 115 at the dose of 100 μM.

20 h Incubation

| No. of derivative | HGP % of ctrl @ 100 μM | HGP % of ctrl @ 50 μM |
|---|---|---|
| 12 | 54 | 89 |
| 46 | 52 | 93 |
| 54 | 44 | 64 |
| 58 | 17 | 32 |
| 118 |  | 57 |

The tested derivatives of formula I therefore have a significant effect on the inhibition of hepatic production of glucose. The strongest inhibitions are obtained with the doses of derivative 58.

Study of the Effect of the Compounds on the Secretion in Response to Glucose at Isolated Perfused Pancreases of N0STZ Diabetic Rats Equipment and Method:

The pancreas was taken on rats made to be diabetic by injection of Streptozotocin on the day of birth [10] and anaesthetized with Pentobarbital (Nembutal©: 45 mg/kg; intraperitoneal route). These rats have a specific deficiency of the insulin response to glucose [11], as observed in humans with diabetes of type II. The isolation and the perfusion of the pancreas were achieved according to a modification [12] of the procedure described by Sussman et al. [13]. The effect of the compounds or reference substances is tested for 35 minutes (from t=20 min to t=55 min) in Krebs buffer, and then 20 minutes (from t=55 min to t=75 min) in the presence of glucose 16.5 mM. The concentration of insulin secreted into the medium is measured by an Elisa assay (ELISA Alpco Cat no. 80-INSRTH-E10). The results are expressed as an average +/−SEM (Standard Error of the Mean) of several experiments.

Table of Results:

|  |  | Insulin secretion peak at G16.5 mM | |
| --- | --- | --- | --- |
| Derivative number | Tested concentration (µM) | Tested product (µU/min.) | Control group (µU/min.) |
| 44 | 10 | 1 724 | 560 ± 71 |
| 54 | 1 | 961 ± 130 | 560 ± 71 |
| 54 | 10 | 1 637 | 560 ± 71 |

The tested derivatives of formula I have a significant effect on restoring insulin secretion in response to glucose at isolated perfused pancreases of NOSTZ diabetic rats.

Study of the Antidiabetic Activity in GK (Goto-Kakisaki) Rats

The antidiabetic activity of compound 118 was evaluated in GK rats, a non-obese model of diabetes of type II. This model was obtained by cross-breeding of Wistar rats selected on the basis of a slight intolerance to glucose [14]. These rats have the majority of dysfunctions observed in diabetes of type II in humans [15]: hyperglycaemia, intolerance to glucose, insulin-resistance, and deteriorated insulin response to glucose. These animals were bred at Metabrain and were housed in an animal housing facility with a regulated temperature (22±2° C.) under constant humidity (50±20%) with a day/night cycle of 12 h (light from 7 h-19 h) and have access ad libitum to food and drink. The housing and experimentation conditions comply with the European directives relating to health and ethical treatment of laboratory animals (ETS123). In this study, the rats used are male 16-week old GK rats having fasted for 2 hours before beginning the study (postabsorptive condition). Monitoring of glycaemia is carried out on 2 groups of rats: One group treated with the compound 118 orally at the single dose of 50 mg/kg and a control group treated orally with the carrier. A blood sample was taken at T0 just before administration of the compound 118 or of the carrier and at times T1 h, T2 h, T4 h and T6 h after administration. The determination of glycaemia is achieved from a drop of blood taken from the tail measured with a glucometer Accu-Check Performa. The results shown below are expressed as a percentage of the decrease of glycaemia at T1 h, T2 h, T4 h and T6 h for the group treated with the compound 118 as compared with the control group

|  | Time after administration | | | |
| --- | --- | --- | --- | --- |
| Compound 118 | T1 h | T2 h | T4 h | T6 h |
| % of activity on glycemia | −14% | −15% | −10% | −8% |
| Statistical significance (Student t test) | p = 0.0242 * | p = 0.0171 * | p = 0.1468 NS | p = 0.2450 NS |

These results show that the compound 118 administered as a single dose at 50 mg/kg is capable of reducing hyperglycaemia of a diabetic rat of type II.

BIBLIOGRAPHY

[1] WO 2010089292;
[2] WO 2010070008;
[3] WO 2010034500;
[4] EP 2168965;
[5] WO 2009080291;
[6] WO 2009023179;
[7] Helvetica Chimica Acta (2007), 90(12), 2349-2367;
[8] Letters in Organic Chemistry (2005), 2(2), 184-187;
[9] Asfari et al., Endocrinology 130: 167-178, 1992;
[10] Portha et al., Diabetes, 23, (1974), 889-895;
[11] Giroix et al., Diabetes, 32, (1983), 445-451
[12] Assan et al., Nature, 239, (1972), 125-126;
[13] Sussman et al., Diabetes, 15, (1966), 466-472;
[14] Goto et al., Proc. Jpn. Acad. 51, 80-85, 1975;
[15] Portha et al., Mol. Cell. Endocrinol., 297: 73-85, 2009;

The invention claimed is:

1. An imidazopyridine derivative of the following general formula I:

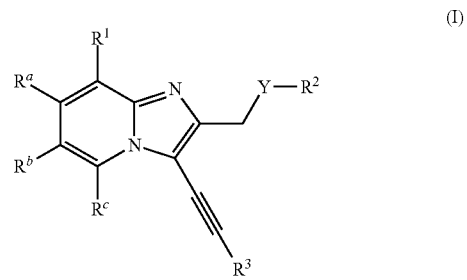

wherein:
Y represents an oxygen or sulfur atom, the group SO, $SO_2$ or —$NR^{19}$, wherein $R^{19}$ represents a hydrogen atom or a $C_1$-$C_6$ alkyl group;
$R^1$, $R^a$, $R^b$ and $R^c$ represent independently of each other a hydrogen atom; a halogen atom; a $C_1$-$C_6$ alkyl group optionally substituted with an —OH group; an —OH group; a —O($C_1$-$C_6$ alkyl) group; a —O($C_1$-$C_6$ alkyl)O ($C_1$-$C_6$ alkyl) group; a —CN group; a —$NR^4R^5$ group wherein $R^4$ and $R^5$ represent independently of each other a hydrogen atom or a $C_1$-$C_6$ alkyl group; or a —($C_1$-$C_6$ alkyl)$NR^6R^7$ group wherein $R^6$ and $R^7$ represent independently of each other a hydrogen atom or a $C_1$-$C_6$ alkyl group;
$R^2$ represents
 a hydrogen atom;
 a $C_1$-$C_6$ alkyl group substituted with an —OH group;
 a ($C_1$-$C_6$ alkyl)$COOR^8$ group wherein $R^8$ represents a hydrogen atom or a $C_1$-$C_6$ alkyl group, the alkyl group may be substituted with an —$NH_2$ or —OH group;
 a ($C_1$-$C_6$ alkyl)$CONHR^9$ group wherein $R^9$ represents an —OH group; a $C_1$-$C_6$ alkyl group; an —O($C_1$-$C_6$ alkyl) group; an aryl group; a heteroaryl group; a —(C=NH)NHCOO($C_1$-$C_6$ alkyl) group; a —(C=NH)$NH_2$ group or a —($C_1$-$C_6$ alkyl)$NR^{10}R^{11}$ group wherein $R^{10}$ and $R^{11}$ represent independently of each other a $C_1$-$C_6$ alkyl group;
 a ($C_1$-$C_6$ alkyl)CO morpholine group;
 a C(=O)$R^{12}$ group wherein $R^{12}$ represents an —O($C_1$-$C_6$ alkyl) group; a $C_1$-$C_6$ alkyl group optionally substituted with an —OH group; a morpholine group; an NH-aryl group wherein the aryl group is optionally substituted with a —COOH or —COO($C_1$-$C_6$ alkyl)

group; or a —NR$^{13}$R$^{14}$ group wherein R$^{13}$ and R$^{14}$ represent independently of each other a C$_1$-C$_6$ alkyl group;

a (C$_1$-C$_6$ alkyl)aryl group, wherein the aryl group is optionally substituted with a —CN, COOH or —COO(C$_1$-C$_6$ alkyl) group;

a (C$_1$-C$_6$ alkyl)heteroaryl group;

an aryl group, wherein the aryl group is optionally substituted with one or more groups selected from —COOH, —COO(C$_1$-C$_6$ alkyl), C$_1$-C$_6$ alkyl substituted with a —OH, —CN, —CONHOH, —NHSO$_2$ (C$_1$-C$_6$ alkyl) or —CONH—(C$_1$-C$_6$ alkyl)NR$^{15}$R$^{16}$ group wherein R$^{15}$ and R$^{16}$ represent independently of each other a C$_1$-C$_6$ alkyl group;

a heteroaryl group;

a heterocyclic group which may optionally include an unsaturation;

a lactone group with 3 to 6 members, optionally substituted with one or more C$_1$-C$_6$ alkyl groups;

or a —SO$_2$(C$_1$-C$_6$ alkyl) group;

R$^3$ represents an aryl group, or heteroaryl group, wherein the aryl group is optionally substituted with one or more groups selected from —C$_1$-C$_6$ alkyl wherein the alkyl group is optionally substituted with one or more halogen atoms, or with a —CN group; a halogen atom, —O(C$_1$-C$_6$ alkyl) wherein the alkyl group is optionally substituted with one or more halogen atoms; —CN; —OH; —NO$_2$; —COOH; NR$^{17}$R$^{18}$ wherein R$^{17}$ and R$^{18}$ represent independently of each other a C$_1$-C$_6$ alkyl group; or —NHCO—(C$_1$-C$_6$ alkyl);

or an enantiomer, diastereoisomer, hydrate, solvate, tautomer, racemic mixture or a pharmaceutically acceptable salt thereof.

2. The imidazopyridine derivative according to claim 1, wherein Y represents an oxygen or sulfur atom or an —NH or -NMe group.

3. The imidazopyridine derivative according to claim 1, wherein R$^1$ R$^a$, R$^b$ and R$^c$ represent a hydrogen atom.

4. The imidazopyridine derivative according to claim 1, wherein R$^2$ represents a (C$_1$-C$_6$ alkyl)COOR$^8$ group wherein R$^8$ represents a hydrogen atom or a C$_1$-C$_6$ alkyl group;

a (C$_1$-C$_6$ alkyl)CONHR$^9$ group wherein R$^9$ represents an —OH group; an —O(C$_1$-C$_6$ alkyl) group; or a —(C$_1$-C$_6$ alkyl)NR$^{10}$R$^{11}$ group wherein R$^{10}$ and R$^{11}$ represent independently of each other a C$_1$-C$_6$ alkyl group;

an aryl group, wherein the aryl group is optionally substituted with one or more groups selected from —COOH, —COO(C$_1$-C$_6$ alkyl), —CONHOH, or —CONH—(C$_1$-C$_6$ alkyl)NR$^{15}$R$^{16}$ wherein R$^{15}$ and R$^{16}$ represent independently of each other a C$_1$-C$_6$ alkyl group; or a —CONH aryl group optionally substituted with a —COOH or —COO(C$_1$-C$_6$ alkyl) group.

5. The imidazopyridine derivative according to claim 4, wherein R$^2$ represents a —(C$_1$-C$_6$ alkyl)COOH group.

6. The imidazopyridine derivative according to claim 1, wherein R$^3$ represents an aryl group, optionally substituted with one or more groups selected from —(C$_1$-C$_6$ alkyl) wherein the alkyl group is optionally substituted with one or more halogen atoms, a halogen atom, —O(C$_1$-C$_6$ alkyl) wherein the alkyl group is optionally substituted with one or more halogen atoms; —CN; or —NO$_2$.

7. The imidazopyridine derivative according to claim 6, wherein R$^3$ represents a phenyl group substituted with one or more groups selected from —(C$_1$-C$_6$ alkyl) substituted with one or more halogen atoms, a halogen atom, —O(C$_1$-C$_6$ alkyl) wherein the alkyl group is substituted with one or more halogen atoms; or —CN.

8. The imidazopyridine derivative according to claim 1, which is selected from the following compounds:

2-(((3-((3-(trifluoromethyl)phenyl)ethynyl)imidazo[1,2-a]pyridin-2-yl)methyl)amino) acetic acid (68);

2-((3-((2-fluorophenyl)ethynyl)imidazo[1,2-a]pyridin-2-yl)methoxy) acetic acid (42);

2-((3-((3-(difluoromethoxy)phenyl)ethynyl)imidazo[1,2-a]pyridin-2-yl)methoxy) acetic acid (35);

2-((3-((3-(trifluoromethoxy)phenyl)ethynyl)imidazo[1,2-a]pyridin-2-yl)methoxy) acetic acid (29);

2-((3-((3-(trifluoromethyl)phenyl)ethynyl)imidazo[1,2-a]pyridin-2-yl)methoxy) benzoic acid (89);

sodium 2-((3-((3-(trifluoromethyl)phenyl)ethynyl)imidazo[1,2-a]pyridin-2-yl)methoxy) acetate (51);

2-((3-((3,4-difluorophenyl)ethynyl)imidazo[1,2-a]pyridin-2-yl)methoxy) acetic acid (38);

2-((3-((3-cyanophenyl)ethynyl)imidazo[1,2-a]pyridin-2-yl)methoxy) acetic acid (27);

2-((3-((3-fluoro-4-(trifluoromethoxy)phenyl)ethynyl)imidazo[1,2-a]pyridin-2-yl)methoxy) acetic acid (39);

2-((3-((3-fluorophenyl)ethynyl)imidazo[1,2-a]pyridin-2-yl)methoxy) acetic acid (40);

2-((3-((3-methoxyphenyl)ethynyl)imidazo[1,2-a]pyridin-2-yl)methoxy) acetic acid (30);

2-((3-((4-(trifluoromethoxy)phenyl)ethynyl)imidazo[1,2-a]pyridin-2-yl)methoxy) acetic acid (32);

2-((3-((4-fluorophenyl)ethynyl)imidazo[1,2-a]pyridin-2-yl)methoxy) acetic acid (44);

2-((3-((4-fluorophenyl)ethynyl)imidazo[1,2-a]pyridin-2-yl)methoxy) benzoic acid (88);

2-((3-((4-fluorophenyl)ethynyl)imidazo[1,2-a]pyridin-2-yl)methoxy)-N-hydroxyacetamide (59);

2-((3-((4-fluorophenyl)ethynyl)imidazo[1,2-a]pyridin-2-yl)methoxy)-N-hydroxybenzamide (96);

sodium 2-((3-((4-nitrophenyl)ethynyl)imidazo[1,2-a]pyridin-2-yl)methoxy) acetate (48);

sodium 2-((3-(phenylethynyl)imidazo[1,2-a]pyridin-2-yl)methoxy) acetate (45);

sodium 2-((3-(phenylethynyl)imidazo[1,2-a]pyridin-2-yl)methoxy) benzoate (92);

sodium 2-((3-(p-tolylethynyl)imidazo[1,2-a]pyridin-2-yl)methoxy) acetate (47);

2-(methyl((3-((3-(trifluoromethyl)phenyl)ethynyl)imidazo[1,2-a]pyridin-2-yl)methyl)amino) acetic acid (73);

3-((3-(phenylethynyl)imidazo[1,2-a]pyridin-2-yl)methoxy) benzoic acid (93);

3-(3-((3-((3-(trifluoromethyl)phenyl)ethynyl)imidazo[1,2-a]pyridin-2-yl)methyl)ureido) benzoic acid (75);

4-((3-((3-(trifluoromethyl)phenyl)ethynyl)imidazo[1,2-a]pyridin-2-yl)methoxy) benzoic acid (90);

ethyl 2-(3-((2-(trifluoromethyl)phenyl)ethynyl)imidazo[1,2-a]pyridin-2-yl)methoxy) acetate (26);

ethyl 2-((3-((2-fluorophenyl)ethynyl)imidazo[1,2-a]pyridin-2-yl)methoxy) acetate (25);

ethyl 2-((3-((3-(difluoromethoxy)phenyl)ethynyl)imidazo[1,2-a]pyridin-2-yl)methoxy) acetate (20);

ethyl 2-((3-((3-(trifluoromethoxy)phenyl)ethynyl)imidazo[1,2-a]pyridin-2-yl)methoxy) acetate (18);

ethyl 2-((3-((3-(trifluoromethyl)phenyl)ethynyl)imidazo[1,2-a]pyridin-2-yl)methoxy) acetate (7);

ethyl 2-((3-((3,4-difluorophenyl)ethynyl)imidazo[1,2-a]pyridin-2-yl)methoxy) acetate (10);

ethyl 2-((3-((3-cyanophenyl)ethynyl)imidazo[1,2-a]pyridin-2-yl)methoxy) acetate (14);
ethyl 2-((3-((3-fluoro-4-(trifluoromethoxy)phenyl)ethynyl)imidazo[1,2-a]pyridin-2-yl)methoxy) acetate (11);
ethyl 2-((3-((3-fluorophenyl)ethynyl)imidazo[1,2-a]pyridin-2-yl)methoxy) acetate (23);
ethyl 2-((3-((3-methoxyphenyl)ethynyl)imidazo[1,2-a]pyridin-2-yl)methoxy) acetate (12);
ethyl 2-((3-((4-(trifluoromethoxy)phenyl)ethynyl)imidazo[1,2-a]pyridin-2-yl)methoxy) acetate (17);
ethyl 2-((3-((4-fluorophenyl)ethynyl)imidazo[1,2-a]pyridin-2-yl)methoxy) acetate (3);
ethyl 2-((3-((4-nitrophenyl)ethynyl)imidazo[1,2-a]pyridin-2-yl)methoxy) acetate (5);
ethyl 2-((3-(phenylethynyl)imidazo[1,2-a]pyridin-2-yl)methoxy) acetate (1);
ethyl 2-((3-(p-tolylethynyl)imidazo[1,2-a]pyridin-2-yl)methoxy) acetate (2);
isopropyl 2-((3-((4-fluorophenyl)ethynyl)imidazo[1,2-a]pyridin-2-yl)methoxy) acetate (54);
methyl 2-((3-((3-(trifluoromethyl)phenyl)ethynyl)imidazo[1,2-a]pyridin-2-yl)methoxy) benzoate (77);
methyl 2-((3-((3-cyanophenyl)ethynyl)imidazo[1,2-a]pyridin-2-yl)methoxy) benzoate (79);
methyl 2-((3-((4-fluorophenyl)ethynyl)imidazo[1,2-a]pyridin-2-yl)methoxy) benzoate (76);
methyl 2-((3-(phenylethynyl)imidazo[1,2-a]pyridin-2-yl)methoxy) benzoate (78);
ethyl 2-(methyl((3-((3-(trifluoromethyl)phenyl)ethynyl)imidazo[1,2-a]pyridin-2-yl)methyl)amino) acetate (72);
methyl 3-((3-((3-(trifluoromethyl)phenyl)ethynyl)imidazo[1,2-a]pyridin-2-yl)methoxy) benzoate (81);
methyl 3-((3-(phenylethynyl)imidazo[1,2-a]pyridin-2-yl)methoxy) benzoate (87);
methyl 3-(3-((3-(trifluoromethyl)phenyl)ethynyl)imidazo[1,2-a]pyridin-2-yl)methyl)ureido) benzoate (74);
methyl 4-(3-((3-(trifluoromethyl)phenyl)ethynyl)imidazo[1,2-a]pyridin-2-yl)methoxy) benzoate (83);
N-(2-(dimethylamino)ethyl)-2-((3-((3-(trifluoromethyl)phenyl)ethynyl)imidazo [1,2-a]pyridin-2-yl)methoxy) acetamide (55);
N-(2-(dimethylamino)ethyl)-2-((3-((4-fluorophenyl)ethynyl)imidazo[1,2-a]pyridin-2-yl)methoxy) acetamide (57);
N-(2-(dimethylamino)ethyl)-2-((3-((4-fluorophenyl)ethynyl)imidazo[1,2-a]pyridin-2-yl)methoxy)benzamide (95);
N-ethoxy-2-(3-((4-fluorophenyl)ethynyl)imidazo[1,2-a]pyridin-2-yl)methoxy) acetamide (58);
sodium 2-((3-((4-fluorophenyl)ethynyl)imidazo[1,2-a]pyridin-2-yl)methoxy) acetate (46);
ethyl 2-[methyl-[[3-[2-[3-(trifluoromethyl)phenyl]ethynyl]imidazo[1,2-a]pyridin-2-yl]methyl]amino]acetate hydrochloride (101);
ethyl 2-[[6-chloro-3-[2-[3-(trifluoromethyl)phenyl]ethynyl]imidazo[1,2-a]pyridin-2-yl]methyl-methyl-amino]acetate (102);
ethyl 2-(methyl((3-((3-(trifluoromethoxy)phenyl)ethynyl)imidazo[1,2-a]pyridin-2-yl)methyl)amino)acetate (103);
ethyl 2-(((6-chloro-3-((3-(trifluoromethoxy)phenyl)ethynyl)imidazo [1,2-a]pyridin-2-yl)methyl)(methyl)amino)acetate hydrochloride (104);
2-(((6-chloro-3-((3-(trifluoromethoxy)phenyl)ethynyl)imidazo[1,2-a]pyridin-2-yl)methyl)(methyl)amino) acetic acid (105);
2-(methyl((3-((3-(trifluoromethoxy)phenyl)ethynyl)imidazo[1,2-a]pyridin-2-yl)methyl)amino) acetic acid (106);
2-(((6-chloro-3-((3-(trifluoromethyl)phenyl)ethynyl)imidazo[1,2-a]pyridin-2-yl)methyl)(methyl)amino)acetic acid (107);
ethyl 2-[[3-[2-[3-(trifluoromethyl)phenyl]ethynyl]imidazo[1,2-a]pyridin-2-yl]methylsulfanyl]acetate (108);
ethyl 2-[[3-[2-[3-(trifluoromethoxy)phenyl]ethynyl]imidazo[1,2-a]pyridin-2-yl]methylsulfanyl]acetate (109);
ethyl 2-[[6-chloro-3-[2-[4-(fluoro)phenyl]ethynyl]imidazo[1,2-a]pyridin-2-yl]methylsulfanyl]acetate (110);
ethyl 2-[[6-chloro-3-[2-[3-(trifluoromethyl)phenyl]ethynyl]imidazo[1,2-a]pyridin-2-yl]methylsulfanyl]acetate (111);
ethyl 2-[[6-chloro-3-[2-[3-(trifluoromethoxy)phenyl]ethynyl]imidazo[1,2-a]pyridin-2-yl]methylsulfanyl]acetate (112);
ethyl (2R)-2-amino-3-[[3-[2-[3-(trifluoromethyl)phenyl]ethynyl]imidazo[1,2-a]pyridin-2-yl]methylsulfanyl] propanoate (113);
ethyl 2-[[8-methoxy-3-[2-[3-(trifluoromethyl)phenyl]ethynyl]imidazo[1,2-a]pyridin-2-yl]methylsulfanyl]acetate (114);
2-[[3-[2-[3-(trifluoromethyl)phenyl]ethynyl]imidazo[1,2-a]pyridin-2-yl]methylsulfanyl]acetic acid (115);
2-[[3-[2-[3-(trifluoromethoxy)phenyl]ethynyl]imidazo[1,2-a]pyridin-2-yl]methylsulfanyl]acetic acid (116);
2-[[6-chloro-3-[2-(4-fluorophenyl)ethynyl]imidazo[1,2-a]pyridin-2-yl]methylsulfanyl]acetic acid (117);
2-[[6-chloro-3-[2-[3-(trifluoromethyl)phenyl]ethynyl]imidazo[1,2-a]pyridin-2-yl]methylsulfanyl]acetic acid (118);
2-[[6-chloro-3-[2-[3-(trifluoromethoxy)phenyl]ethynyl]imidazo[1,2-a]pyridin-2-yl]methylsulfanyl]acetic acid (119);
2-[[8-methoxy-3-[2-[3-(trifluoromethyl)phenyl]ethynyl]imidazo[1,2-a]pyridin-2-yl]methylsulfanyl]acetic acid (120);
ethyl 2-[[3-[2-[3-(trifluoromethyl)phenyl]ethynyl]imidazo[1,2-a]pyridin-2-yl]methylsulfonyl]acetate (121);
ethyl 2-[[6-chloro-3-[2-[3-(trifluoromethoxy)phenyl]ethynyl]imidazo[1,2-a]pyridin-2-yl]methylsulfonyl]acetate (122);
2-[[6-chloro-3-[2-[3-(trifluoromethoxy)phenyl]ethynyl]imidazo[1,2-a]pyridin-2-yl]methylsulfonyl]acetic acid (123);
N-(3-pyridyl)-2-[[3-[2-[3-(trifluoromethyl)phenyl]ethynyl]imidazo[1,2-a]pyridin-2-yl]methylsulfanyl]acetamide (124);
N-(3-pyridyl)-2-[[3-[2-[3-(trifluoromethoxy)phenyl]ethynyl]imidazo[1,2-a]pyridin-2-yl]methoxy]acetamide (125);
N-(3-pyridyl)-2-[[3-[2-[3-(trifluoromethoxy)phenyl]ethynyl]imidazo[1,2-a]pyridin-2-yl]methylsulfanyl]acetamide (126);
4-hydroxy-3,3-dimethyl-2-[[3-[2-[3-(trifluoromethyl)phenyl]ethynyl]imidazo [1,2-a]pyridin-2-yl]methoxy] butanoic acid(129);
2-[[8-methoxy-3-[2-[3-(trifluoromethyl)phenyl]ethynyl]imidazo[1,2-a]pyridin-2-yl]methylsulfanyl]ethanol (130);
2-[[6-chloro-3-[2-[3-(trifluoromethyl)phenyl]ethynyl]imidazo[1,2-a]pyridin-2-yl]methylsulfanyl]ethanol (131);

N-carbamimidoyl-2-[[3-[2-[3-(trifluoromethyl)phenyl]ethynyl]imidazo[1,2-a]pyridin-2-yl]methylsulfanyl]acetamide hydrochloride (135).

9. A pharmaceutical composition comprising a derivative according to claim 1 and a pharmaceutically acceptable excipient.

10. The pharmaceutical composition according to claim 9 further comprising another antidiabetic agent.

11. A method for treating diabetes and/or hyperglycemia, for reducing hyperglycemia, for delaying the occurrence of diabetes, for inhibiting hepatic glucose production and/or for restoring insulin secretion in response to glucose and/or for treating the complications of diabetes and/or pathologies associated with diabetes selected from functional and quantitative abnormalities of endocrine pancreatic cells, insulin resistance, diabetic neuropathy, diabetic nephropathy, diabetic retinopathy, inflammation, obesity, hypertension, and wound healing problems, comprising the administration of an effective amount of a derivative according to claim 1 to a patient in need thereof.

12. The method according to claim 11, wherein diabetes is diabetes of type II.

13. The method according to claim 11, for treating and/or reducing hyperglycaemia.

14. The derivative according to claim 1, wherein the aryl group is a phenyl group.

15. The derivative according to claim 1, wherein the halogen atom is F.

16. The derivative according to claim 5, wherein $R_2$ represents $CH_2$ COOH.

17. The derivative according to claim 2, wherein Y represents an oxygen atom.

18. The pharmaceutical composition according to claim 10, wherein the other antidiabetic agent is metformin.

19. The method according to claim 11 for treating diabetes and/or for delaying the occurrence of diabetes.

20. A method for treating diabetes and/or hyperglycemia, for reducing hyperglycemia, for delaying the occurrence of diabetes, for inhibiting hepatic glucose production and/or for restoring insulin secretion in response to glucose and/or for treating the complications of diabetes and or pathologies associated with diabetes selected from functional and quantitative abnormalities of endocrine pancreatic cells, insulin resistance and obesity, comprising the administration of an effective amount of a derivative according to claim 1 to a patient in need thereof.

* * * * *